(12) United States Patent
Rothbard et al.

(10) Patent No.: US 7,169,814 B2
(45) Date of Patent: Jan. 30, 2007

(54) GUANIDINIUM TRANSPORT REAGENTS AND CONJUGATES

(75) Inventors: Jonathan B. Rothbard, Woodside, CA (US); Paul A. Wender, Menlo Park, CA (US); Kanaka Pattabiraman, Menlo Park, CA (US); Erin T. Pelkey, Phelps, NY (US); Theodore C. Jessop, Palo Alto, CA (US)

(73) Assignees: The Board of Trustees of the Leland Stanford Junior University, Stanford, CA (US); Cellgate, Inc., Sunnyvale, CA (US)

( * ) Notice: Subject to any disclaimer, the term of this patent is extended or adjusted under 35 U.S.C. 154(b) by 230 days.

(21) Appl. No.: 10/318,278

(22) Filed: Dec. 11, 2002

(65) Prior Publication Data

US 2004/0161405 A9    Aug. 19, 2004

Related U.S. Application Data

(60) Provisional application No. 60/339,696, filed on Dec. 11, 2001.

(51) Int. Cl.
*A61K 31/155* (2006.01)
(52) U.S. Cl. ............... 514/565; 554/53; 514/20; 514/631; 548/336.5; 530/327; 530/328
(58) Field of Classification Search ........... 514/12–17, 514/20, 565, 631; 530/324–329, 345; 554/53; 548/336.5
See application file for complete search history.

(56) References Cited

U.S. PATENT DOCUMENTS

| | | | | |
|---|---|---|---|---|
| 4,004,074 A | * | 1/1977 | Gerecht et al. | 526/305 |
| 5,053,326 A | * | 10/1991 | Renz | 435/6 |
| 5,723,496 A | * | 3/1998 | Nakada | 514/634 |
| 5,824,474 A | * | 10/1998 | Matsuhisa et al. | 435/6 |
| 6,251,433 B1 | * | 6/2001 | Zuckermann et al. | 424/486 |
| 6,464,971 B1 | * | 10/2002 | Matthews et al. | 424/78.17 |
| 6,534,639 B1 | * | 3/2003 | Manoharan et al. | 536/23.1 |
| 6,642,365 B1 | * | 11/2003 | Lapidot et al. | 536/13.7 |
| 6,669,951 B2 | * | 12/2003 | Rothbard et al. | 424/436 |
| 6,730,293 B1 | * | 5/2004 | Rothbard et al. | 424/78.05 |
| 2002/0127198 A1 | | 9/2002 | Rothbard et al. | |
| 2003/0032593 A1 | * | 2/2003 | Wender et al. | 514/12 |

FOREIGN PATENT DOCUMENTS

| | | |
|---|---|---|
| WO | WO 98/52614 | 11/1998 |
| WO | WO 01/13957 | 3/2001 |

OTHER PUBLICATIONS

Fuchs et al. (2001), "Effect of Guanidinium Display on the Translocation of Molecules through Membranes," *Abstracts of Papers American Chemical Society* 222(1-2), abstract only.
Rothbard et al. (2002), "Arginine-Rich Molecular Transporters for Drugs: The Roles of Backbone and Side Chain Variations on Cellular Uptake," Cell-Penetrating Peptides, Chapter 7, pp. 141-160.
Wender et al. (2000), "The Design, Synthesis, and Evaluation of Molecules that Enable or Enhance Cellular Uptake: Peptoid Molecule Transporters," *PNAS* 97(24):13003-13008.
Wender et al. (2002), "Oligocarbamate Molecular Transporters: Design, Synthesis, and Biological Evaluation of a New Class of Transporters for Drug Delivery," J. Am. Chem. Soc. 124(45):13382-13383.
Wright et al. (2003), "Guanidinium Rich Peptide Transporters and Drug Delivery," *Current Protein and Peptide Science* 4(2):105-124.

* cited by examiner

*Primary Examiner*—David Lukton
(74) *Attorney, Agent, or Firm*—Mintz, Levin, Cohn, Ferris Glovsky and Popeo, P.C.

(57) ABSTRACT

Transport reagents and conjugates of therapeutic agents linked to transport reagents are described. In particular, the transport reagents have a plurality of guanidinium moieties that are either contiguous or spaced along a backbone, but are sufficiently removed from the backbone via tethers, to allow their interaction with a cell or tissue surface, leading to uptake of the therapeutic agent.

32 Claims, 28 Drawing Sheets

Figure 1

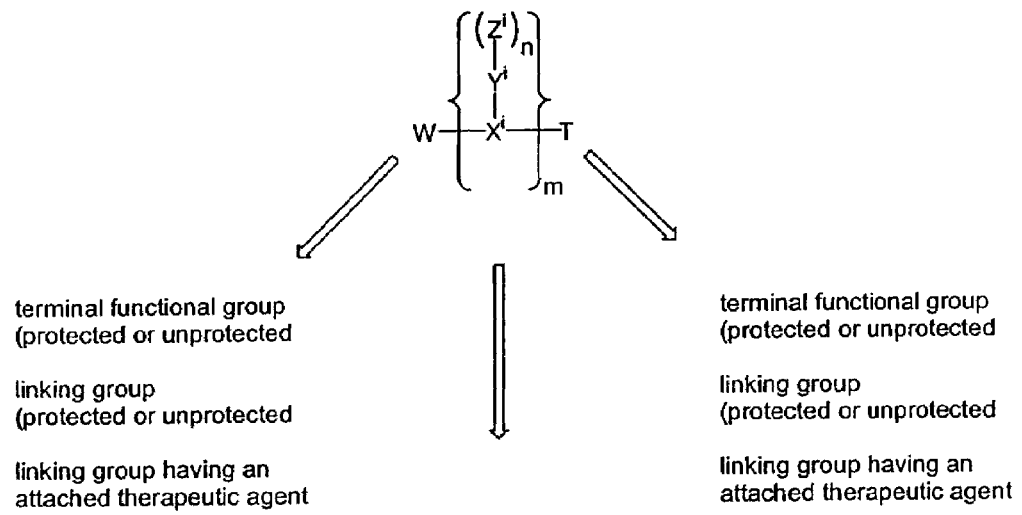

terminal functional group
(protected or unprotected linking group
(protected or unprotected linking group having an
attached therapeutic agent terminal functional group
(protected or unprotected linking group
(protected or unprotected linking group having an
attached therapeutic agent

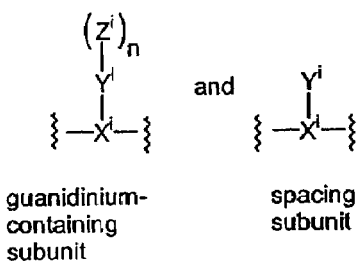

guanidinium-
containing
subunit spacing
subunit

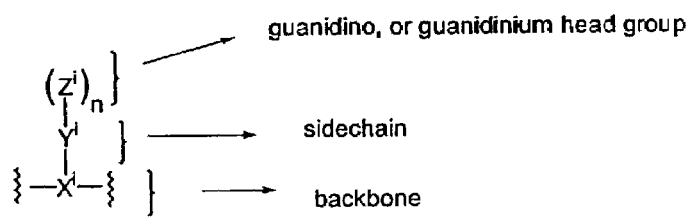

guanidino, or guanidinium head group sidechain backbone

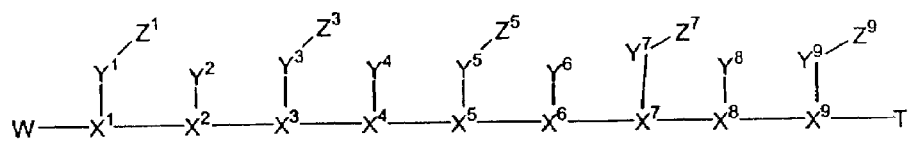

Spaced guanidinium transport reagent

Figure 4
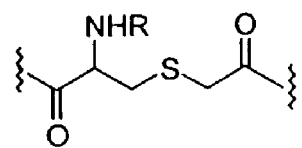
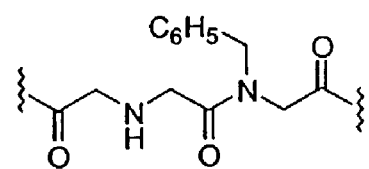
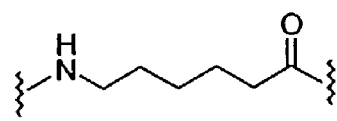
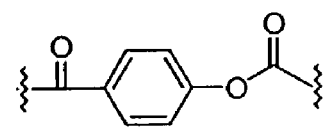
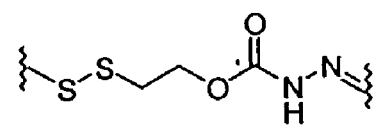
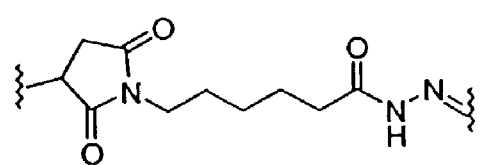

Figure 9A
Synthetic Schemes for FK 506 Conjugates
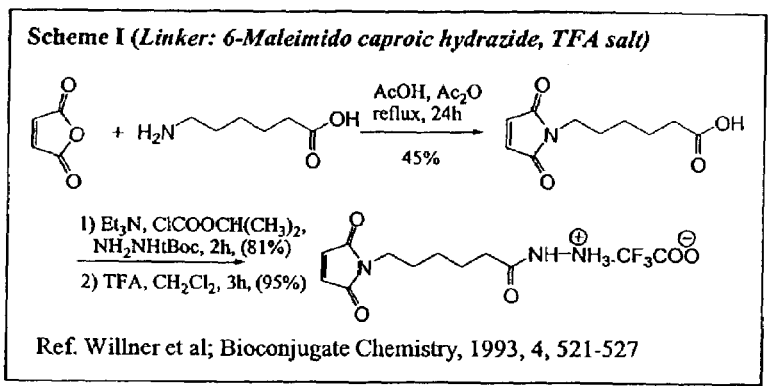
Scheme I (*Linker: 6-Maleimido caproic hydrazide, TFA salt*)
Ref. Willner et al; Bioconjugate Chemistry, 1993, 4, 521-527
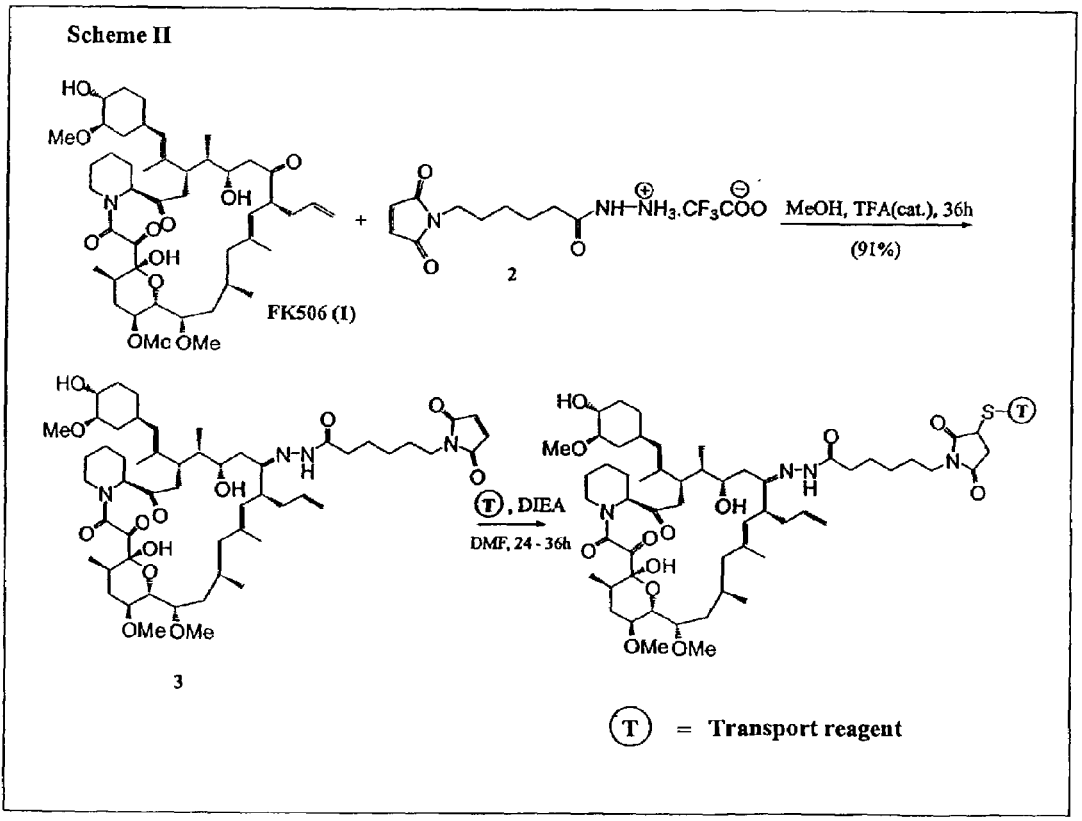
Scheme II
(T) = Transport reagent

Synthetic Schemes for FK 506 Conjugates (contd.)

Ref. Kaneko et al; Bioconjugate Chemistry, 1991, 2, 133

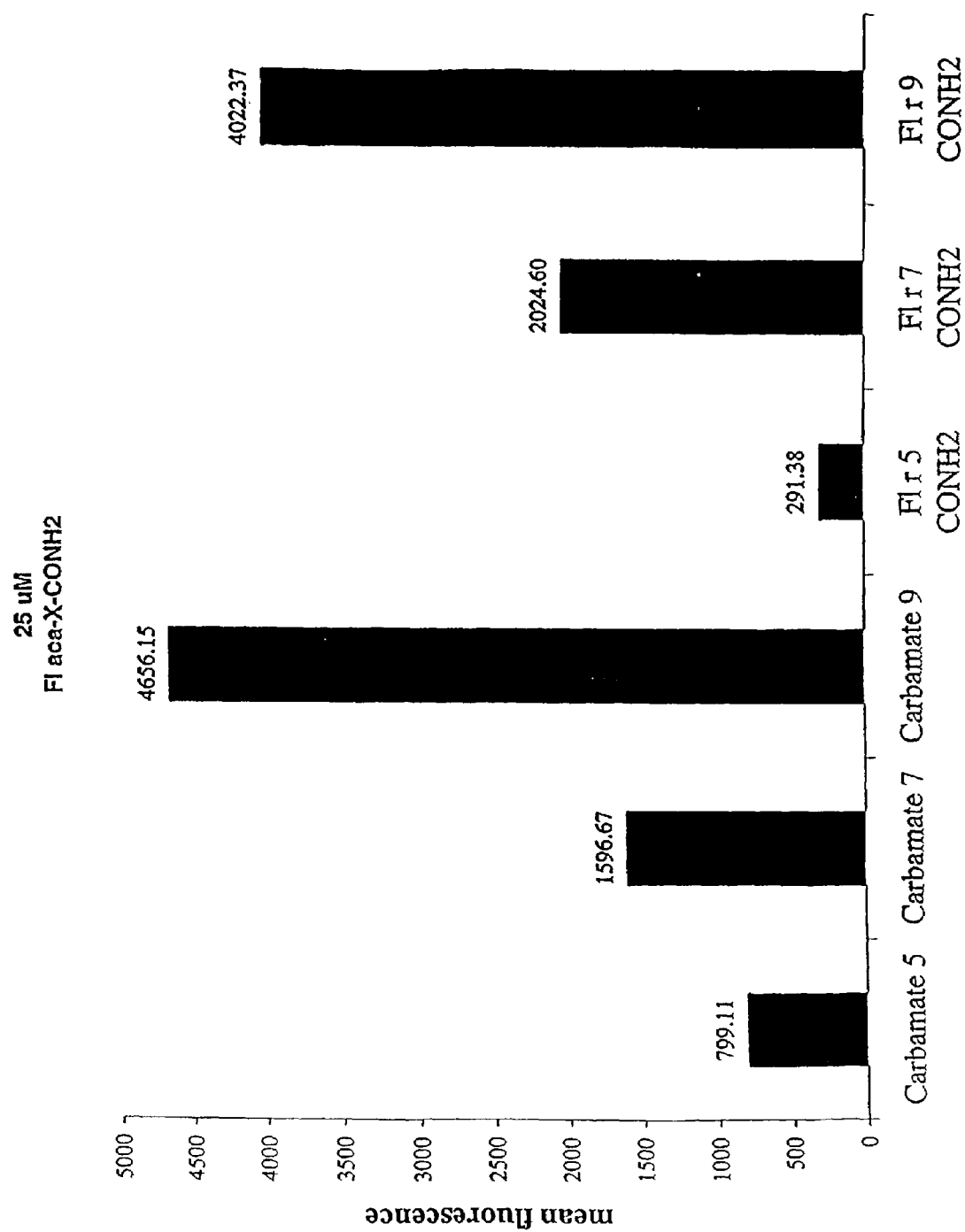

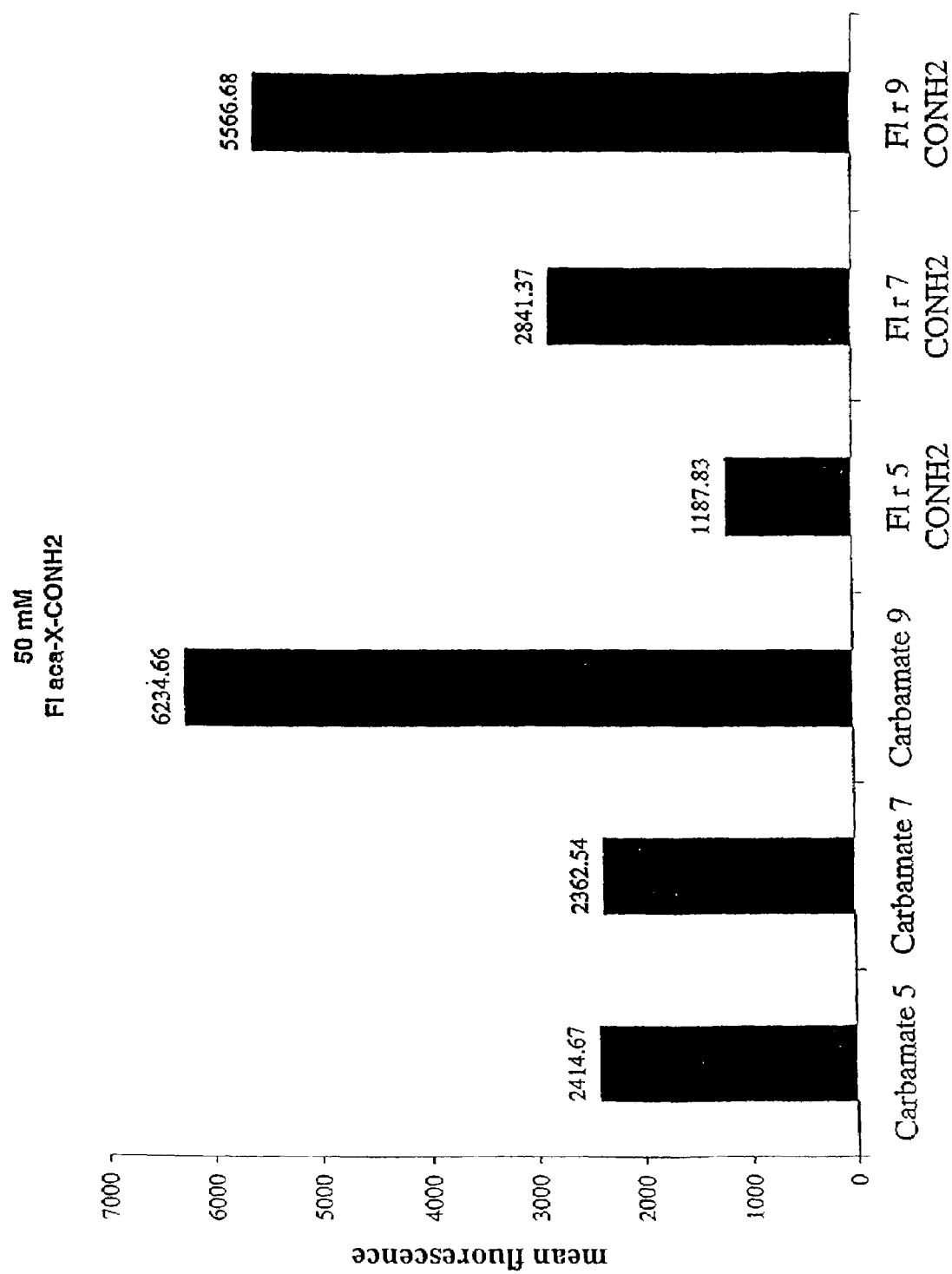

Figure 11
Scheme 1
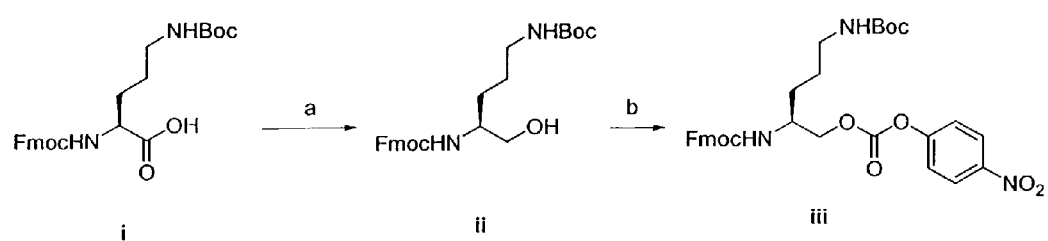
Scheme 2
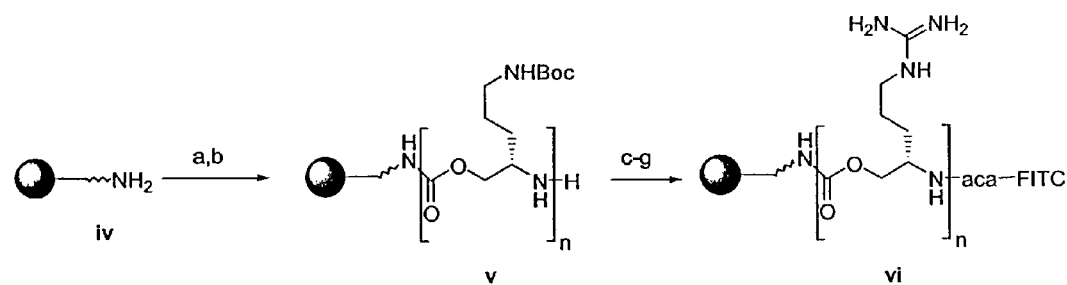

Figure 12
Scheme 3
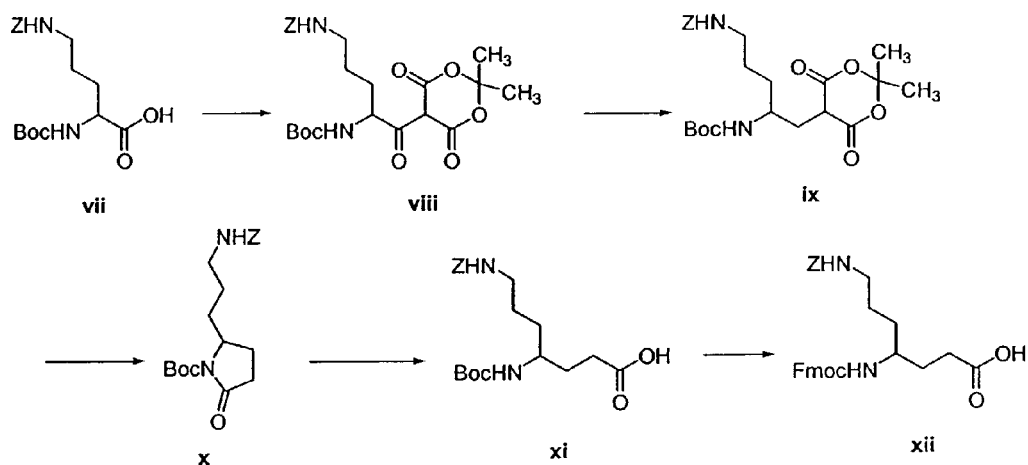
Scheme 4
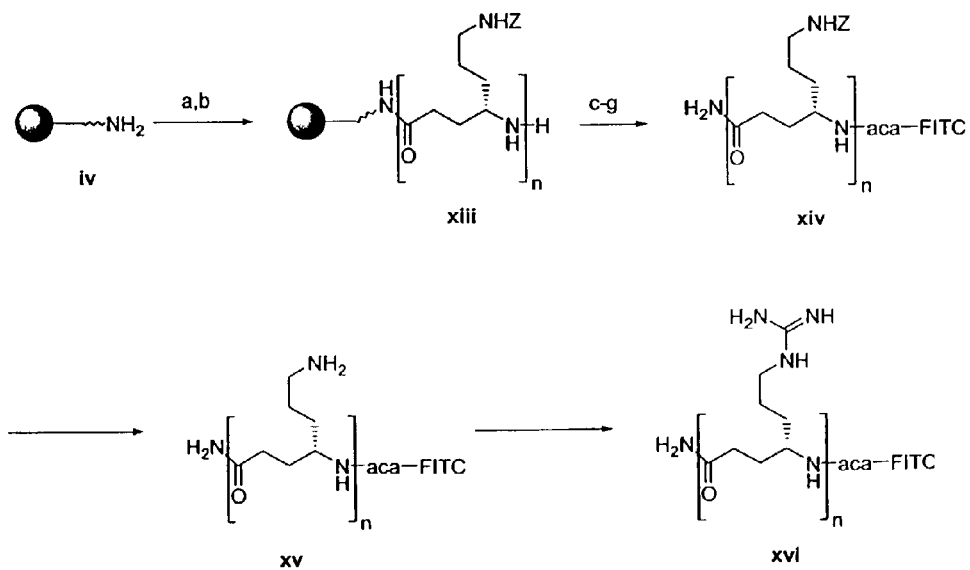

Scheme 6

Revised Common Route For Urea, Oxalamide, Succinate, Glutarate Mimics

Figure 16a
Scheme 8
8A. Amide linkage.
Target system.
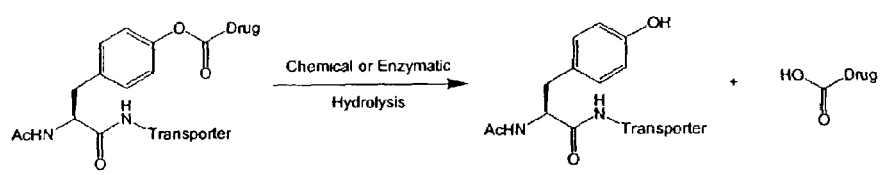
Model System.
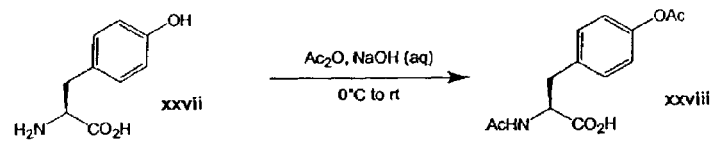
8B. Carbonate linkage.
Target system.
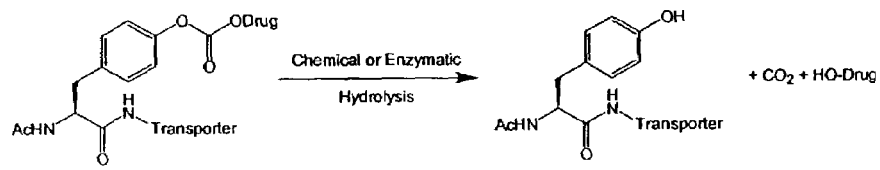
Model System.
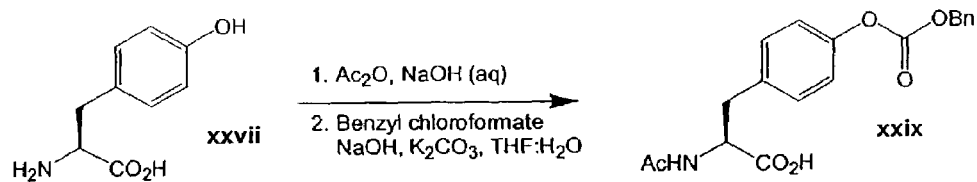

Figure 16b
Scheme 8 (cont'd)
8C. Carbamate Linkage.
Target system.
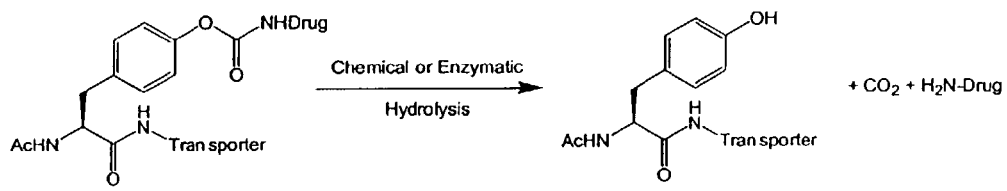
Model system.
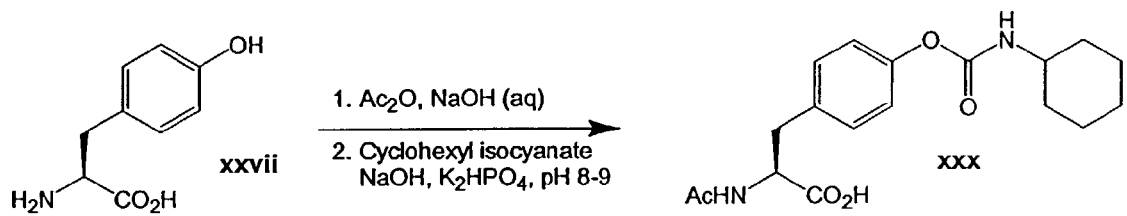

8D. Photolabile Linkage.

8E. Phosphatase Labile Linkage.

Scheme 9

Scheme 10

Scheme 11

Scheme 12 a) i) BnBr, DCM ii) NMM, Boc$_2$O 21% b) TsCl, NMM, DMAP, DCM, 80%
c) NaI, Acetone, reflux d) I$_2$, PPh$_3$, imid., DCM e) Allyl Bromide, NaH, DMF, 0°C, 74%

Figure 21

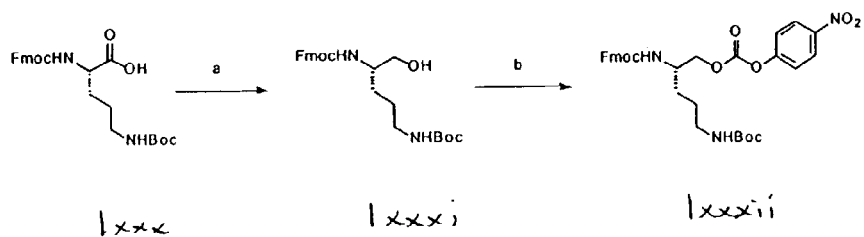

Scheme 13  Synthesis of Oligocarbamate monomer (a) (i) isobutyl chloroformate, DME, NMM, -15 °C  (ii)  NaBH$_4$, H$_2$O (85%).
(b) p-nitrophenyl chloroformate, THF, pyridine ( 92%)

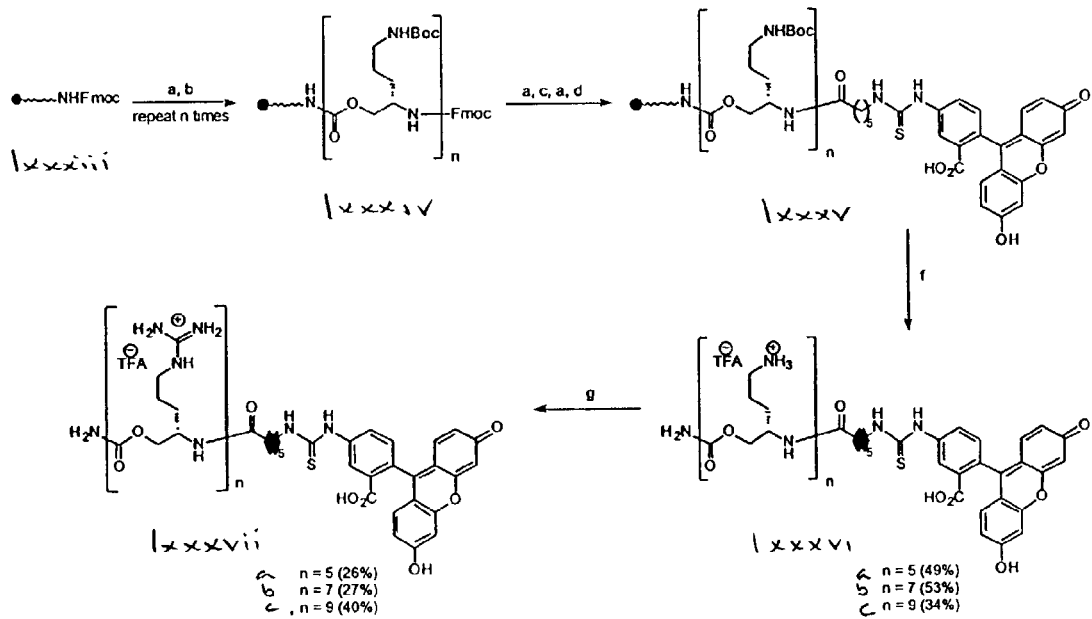

Scheme 14  Solid and solution phase synthesis of fluoresceine - transporter conjugates (a) 20% piperdine/DMF; (b)  3, HOBT, DIEA, DMF, (c) Fmoc-aca-OH, DIC, DMF, HOBT;
(d) FITC, DIEA, DMF, (f) 95.5 TFA/TIS, (g) pyrazole-1-carboxamidine hydrochloride,  K$_2$CO$_3$, H$_2$O

GUANIDINIUM TRANSPORT REAGENTS AND CONJUGATES

CROSS-REFERENCES TO RELATED APPLICATIONS

This application claims the benefit of U.S. Provisional Ser. No. 60/339,696, filed Dec. 11, 2001, the disclosure of which is incorporated hereinby reference.

STATEMENT AS TO RIGHTS TO INVENTIONS MADE UNDER FEDERALLY SPONSORED RESEARCH AND DEVELOPMENT

This invention was made with the support of NIH grant number CA 65237. Accordingly, the U.S. Government has certain rights in this invention.

BACKGROUND OF THE INVENTION

The present invention is directed to methods and compositions that are effective to enhance transport of biologically active agents, such as organic compounds, polypeptides, oligosaccharides, nucleic acids, and metal ions, across biological membranes.

The plasma membranes of cells present a barrier to passage of many useful therapeutic agents. In general, a drug must be freely soluble in both the aqueous compartments of the body and the lipid layers through which it must pass, in order to enter cells. Highly charged molecules in particular experience difficulty in passing across membranes. Many therapeutic macromolecules such as peptides and oligonucleotides are also particularly intractable to transmembrane transport. Thus, while biotechnology has made available a greater number of potentially valuable therapeutics, bioavailability considerations often hinder their medicinal utility. There is therefore a need for reliable means of transporting drugs, and particularly macromolecules, into cells.

The present invention is based in part on the applicants' discovery that conjugation of certain oligomers or polymers to small molecules or macromolecules is effective to significantly enhance transport of the attached molecule across biological membranes. The transport reagents contain highly basic subunits either interrupted by neutral subunits or having a longer backbone to provide suitable spacing between the basic groups (e.g., guanidino or amidino groups).

SUMMARY OF THE INVENTION

The present invention includes, in one aspect, a method for enhancing transport of a selected compound across a biological membrane. In the method, a biological membrane is contacted with a conjugate containing a biologically active agent that is covalently attached to at least one transport reagent. The conjugate is effective to promote transport of the agent across the biological membrane at a rate that is greater than the transmembrane transport rate of the biological agent in non-conjugated form.

Accordingly, the present invention provides in another aspect, a compound having the formula:

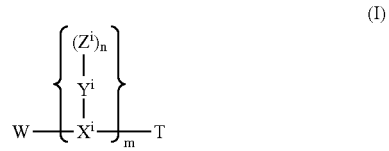

wherein the subscript m is an integer of from 6 to 50; T represents a protected or unprotected first terminal functional group, a protected or unprotected linking group, or a linking group having an attached biologically active agent; and W represents a protected or unprotected second terminal functional group, a protected or unprotected linking group, or a linking group having an attached therapeutic agent. In the subunit portion (enclosed by brackets), the subscript n can be 0, 1 or 2; each $X^i$ is a backbone subunit wherein the superscript i is an integer of from 1 to m and denotes the position downstream of W; each $Y^i$ is selected from H, an amino acid sidechain, aryl, and heteroaryl, when the subscript n is 0; or is selected from $(C_1-C_8)$alkylene, $(C_2-C_8)$alkenylene, $(C_2-C_8)$alkynylene, $(C_2-C_8)$heteroalkylene, $(C_3-C_8)$cycloalkylalkylene, $(C_2-C_8)$spirocycloalkylene, arylene, heteroarylene, and combinations thereof, when the subscript n is 1 or 2; each $Z^i$ is a guanidinium moiety, preferably selected from:

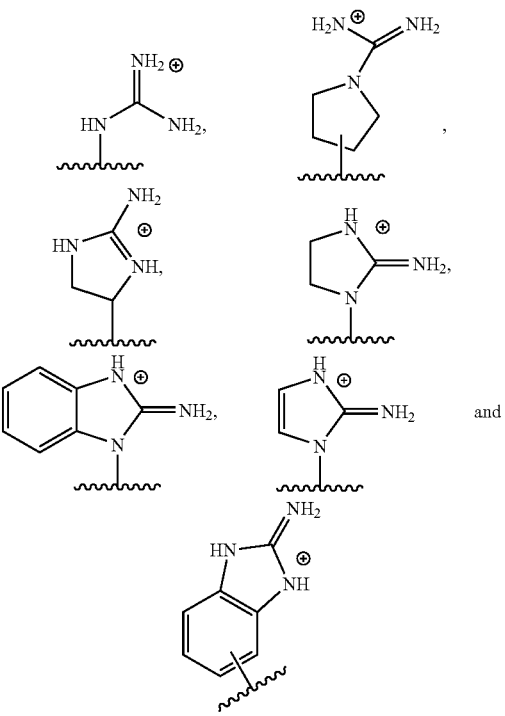

wherein the wavy line denotes the point of attachment to $Y^i$. Accordingly, for each of the subunits the subscript n indicates the absence or presence of one or two Z guanidinium moieties at each i position; with the proviso that the compound has at least 4 guanidinium moieties that can be the same or different.

More specifically, W and T can be functional groups such as hydroxy, thiol, carboxy, carboxamide, aldehyde, amino and the like, that can be in a protected or unprotected from. Suitable protecting groups for various functional groups are described in, for example, Greene and Wuts, PROTECTIVE GROUPS IN ORGANIC SYNTHESIS, 2nd Ed., John Wiley & Sons, New York, N.Y., 1991. Additionally, either or both of T and W can be a linking group which is either a vestige of the attachment chemistry used during synthesis of the transport reagent on a solid support, or a linking group used to attach a biologically active agent. For those embodiments in which either T or W is a linking group used to attach a biologically active agent, the linking group is preferably one that is cleavable in vivo and results in release of the therapeutic agent from the transport reagent.

The compounds, compositions and methods described herein can be used to enhance transport of selected therapeutic agents across any of a number of biological membranes including, but not limited to, eukaryotic cell membranes, prokaryotic cell membranes, and cell walls. Exemplary prokaryotic cell membranes include bacterial membranes. Exemplary eukaryotic cell membranes of interest include, but are not limited to membranes of dendritic cells, epithelial cells, endothelial cells, keratinocytes, muscle cells, fungal cells, plant cells, and the like.

Biologically active agents (which encompass therapeutic agents and drugs, as the terms are used interchangeably) include, but are not limited to metal ions, which are typically delivered as metal chelates; small organic molecules, such as anticancer (e.g., taxane) and antimicrobial molecules (e.g., against bacteria or fungi such as yeast); and macromolecules such as nucleic acids, peptides, proteins, and analogs thereof. In one preferred embodiment, the agent is a nucleic acid or nucleic acid analog, such as a ribozyme which optionally contains one or more 2'-deoxy nucleotide subunits for enhanced stability. Alternatively, the agent is a peptide nucleic acid (PNA). In another preferred embodiment, the agent is a polypeptide, such as a protein antigen, and the biological membrane is a cell membrane of an antigen-presenting cell (APC).

The agent may be linked to the transport reagent by a linking group, which may impart conformational flexibility within the conjugate and facilitate interactions between the agent and its biological target. In one embodiment, the linking group is a cleavable linker, e.g., containing a linker group that is cleavable by an enzyme or by solvent-mediated cleavage, such as an ester, amide, or disulfide group. In another embodiment, the cleavable linker contains a photocleavable group.

In a more specific embodiment, the cleavable linker contains a first cleavable group that is distal to the biologically active agent, and a second cleavable group that is proximal to the agent, such that cleavage of the first cleavable group yields a linker-agent conjugate containing a nucleophilic moiety capable of reacting intramolecularly to cleave the second cleavable group, thereby releasing the agent from the linker and transport reagent.

In another aspect, the invention provides a method to screen a plurality of conjugates for a selected biological activity, wherein the conjugates are formed from a plurality of candidate agents. The conjugates are contacted with a cell that exhibits a detectable signal upon uptake of the conjugate into the cell, such that the magnitude of the signal is indicative of the efficacy of the conjugate with respect to the selected biological activity. This method is particularly useful for testing the activities of agents that by themselves are unable, or poorly able, to enter cells to manifest biological activity. In one embodiment, the candidate agents are selected from a combinatorial library.

The invention also includes a conjugate library which is useful for screening in the above method.

In another aspect, the invention includes a pharmaceutical composition for delivering a biologically active agent across a biological membrane. The composition comprises a conjugate containing a biologically active agent covalently attached to at least one transport reagent as described above, and a pharmaceutically acceptable excipient. The transport reagent is effective to impart to the biologically active agent a rate of trans-membrane transport that is greater than the trans-membrane transport rate of the biologically active agent in non-conjugated form. The composition may additionally be packaged with instructions for using it.

In another aspect, the invention includes a therapeutic method for treating a mammalian subject, particularly a human subject, with a pharmaceutical composition as above.

These and other objects and features of the invention will become more fully apparent when the following detailed description of the invention is read in conjunction with the accompanying drawings.

BRIEF DESCRIPTION OF THE DRAWINGS

FIG. 1 illustrates the components of the guanidinium transport reagents provided in the invention. The guanidinium head groups, sidechains and backbone components are provided along with an illustration of a spaced guanidinium transport reagent (e.g., subunits with guanidinium headgroups linked to subunits without guanidinium headgroups).

FIG. 4 illustrates a number of linking groups that can be used to attach the guanidinium transport reagents to therapeutic agents to form conjugates.

FIG. 9A and FIG. 9B show synthetic schemes for preparing conjugates in which FK506 is attached to a transporter using alternative linking strategies.

FIGS. 10A, 10B and 10C provide histogram comparisons between carbamate transport reagents and polyArg transport reagents.

FIG. 11 provides Schemes 1 and 2 illustrating the preparation of transport reagents having a carbamate backbone. Synthesis can be accomplished on a solid support and aminocaproic acid (aca) is used as a linking group to the biological agent (FITC).

FIG. 12 provides Schemes 3 and 4 illustrating the preparation of transport reagents having a γ-peptide backbone. Synthesis can be accomplished on a solid support and aminocaproic acid (aca) is used as a linking group to the biological agent (FITC).

FIGS. 16A, 16B, 16C and 16D provide Scheme 8 which illustrates the use of amide linkages (8A), carbonate linkages (8B), carbamate linkages (8C), photolabile linkages (8D) and phosphatase-labile linkages (8E).

FIG. 21 provides Schemes 13 and 14 illustrating, respectively, the preparation of a protected monomeric unit for the synthesis of transport reagents having a carbamate backbone, and the solid-phase preparation of a transport reagent having a carbamate beginning with the protected monomeric unit in Scheme 13.

DESCRIPTION OF THE INVENTION

I. Definitions

Figure 2:
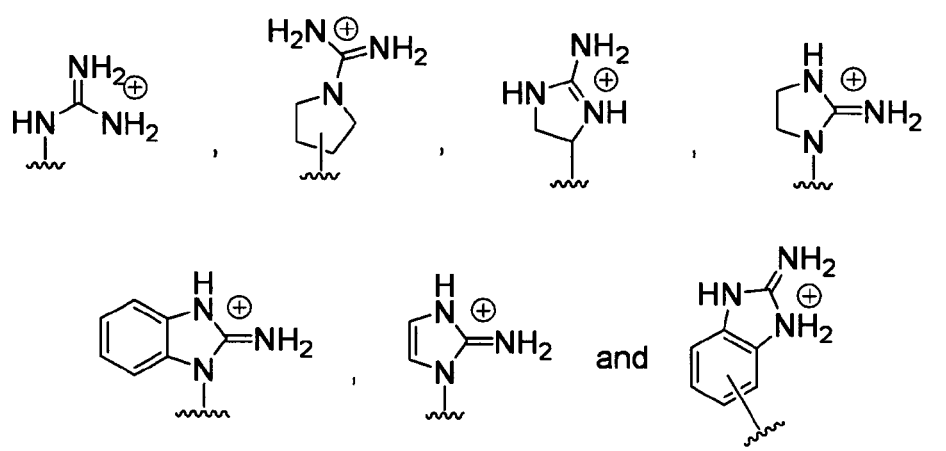
FIG. 2 illustrates a number of guanidinium headgroups that can be used in the present invention.

The term "biological membrane" as used herein refers to a lipid-containing barrier which separates cells or groups of cells from the extracellular space. Biological membranes include, but are not limited to, plasma membranes, cell walls, intracellular organelle membranes, such as the mitochondrial membrane, nuclear membranes, and the like.

The term "transmembrane concentration" refers to the concentration of a compound present on the side of a membrane that is opposite or "trans" to the side of the membrane to which a particular composition has been added. For example, when a compound is added to the extracellular fluid of a cell, the amount of the compound measured subsequently inside the cell is the transmembrane concentration of the compound.

"Biologically active agent" or "biologically active substance" or "biological agent" refers to a chemical substance, such as a small molecule, macromolecule, or metal ion, that causes an observable change in the structure, function, or composition of a cell upon uptake by the cell. Observable changes include increased or decreased expression of one or more mRNAs, increased or decreased expression of one or more proteins, phosphorylation of a protein or other cell component, inhibition or activation of an enzyme, inhibition or activation of binding between members of a binding pair, an increased or decreased rate of synthesis of a metabolite, increased or decreased cell proliferation, and the like.

The term "macromolecule" as used herein refers to large molecules (MW greater than 1000 daltons) exemplified by, but not limited to, peptides, proteins, oligonucleotides and polynucleotides of biological or synthetic origin.

"Small organic molecule" refers to a carbon-containing agent having a molecular weight (MW) of from about 100 to about 1000.

The terms "therapeutic agent", "therapeutic composition", and "therapeutic substance" refer, without limitation, to any composition that can be used to the benefit of a mammalian species. Such agents may take the form of ions, small organic molecules, peptides, proteins or polypeptides, oligonucleotides, and oligosaccharides, for example.

The terms "non-polypeptide agent" and "non-polypeptide therapeutic agent" refer to the portion of a transport conjugate that does not include the transport reagent, and that is a biologically active agent other than a polypeptide. An example of a non-polypeptide agent is an anti-sense oligonucleotide, which can be conjugated to a transport reagent to form a conjugate for enhanced delivery across biological membranes.

The term "polymer" refers to a linear chain of two or more identical or non-identical subunits joined by covalent bonds. A peptide is an example of a polymer that can be composed of identical or non-identical amino acid subunits that are joined by peptide linkages.

The term "peptide" as used herein refers to a compound made up of a single chain of D- or L-amino acids or a mixture of D- and L-amino acids joined by peptide bonds. Generally, peptides contain at least two amino acid residues and are less than about 50 amino acids in length.

The term "protein" as used herein refers to a compound that is composed of linearly arranged amino acids linked by peptide bonds, but in contrast to peptides, has a well-defined conformation. Proteins, as opposed to peptides, generally consist of chains of 50 or more amino acids.

"Polypeptide" as used herein refers to a polymer of at least two amino acid residues and which contains one or more peptide bonds. "Polypeptide" encompasses peptides and proteins, regardless of whether the polypeptide has a well-defined conformation.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$–$C_{10}$ means one to ten carbons). Examples of saturated hydrocarbon radicals include groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "alkylene" by itself or as part of another substituent means a divalent radical derived from an alkane, as exemplified by —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having six or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified by —$CH_2$—$CH_2$—S—$CH_2CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$–$C_4$)alkyl" is mean to include trifluoromethyl, 2,2,2-trifluoroethyl, 4-Chlorobutyl, 3-bromopropyl, and the like.

The term "aryl" means, unless otherwise stated, a polyunsaturated, typically aromatic, hydrocarbon substituent which can be a single ring or multiple rings (up to three rings) which are fused together or linked covalently. The term "heteroaryl" refers to aryl groups (or rings) that contain from zero to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups selected from: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —CN and —NO$_2$ in a number ranging from zero to (2m'+1), where m' is the total number of carbon atoms in such radical. R', R" and R'" each independently refer to hydrogen, unsubstituted ($C_1$–$C_8$)alkyl and heteroalkyl, unsubstituted aryl, aryl substituted with 1–3 halogens, unsubstituted alkyl, alkoxy or thioalkoxy groups, or aryl-($C_1$–$C_4$)alkyl groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl. From the above discussion of substituents, one of skill in the art will understand that the term "alkyl" is meant to include groups such as haloalkyl (e.g., —$CF_3$ and —$CH_2CF_3$) and acyl (e.g., —C(O)$CH_3$, —C(O)$CF_3$, —C(O)$CH_2OCH_3$, and the like). Preferably, the substituted alkyl and heteroalkyl groups have from 1 to 4 substituents, more preferably 1, 2 or 3 substituents. Exceptions are those perhalo alkyl groups (e.g., pentafluoroethyl and the like) which are also preferred and contemplated by the present invention.

Similarly, substituents for the aryl and heteroaryl groups are varied and are selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R'", —NH—C(NH$_2$)=NH, —NR'C(NH$_2$)=NH, —NH—C(NH$_2$)=NR', —S(O)R', —S(O)$_2$R', —S(O)$_2$NR"R", —N$_3$, —CH(Ph)$_2$, perfluoro(C$_1$–C$_4$)alkoxy, and perfluoro(C$_1$–C$_4$)alkyl, in a number ranging from zero to the total number of open valences on the aromatic ring system; and where R', R" and R'" are independently selected from hydrogen, (C$_1$–C$_8$)alkyl and heteroalkyl, unsubstituted aryl and heteroaryl, (unsubstituted aryl)-(C$_1$–C$_4$)alkyl, and (unsubstituted aryl)oxy-(C$_1$–C$_4$)alkyl.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted (C$_1$–C$_6$)alkyl.

As used herein, the term "heteroatom" is meant to include oxygen (O), nitrogen (N), sulfur (S) and silicon (Si).

The terms "guanidyl", "guanidinyl", and "guanidino" are used interchangeably to refer to a moiety having the formula —HN—C(=NH)NH$_2$ (in unprotonated form). As an example, arginine contains a guanidyl (guanidino) moiety, and is also referred to as 2-amino-5-guanidinovaleric acid or α-amino-δ-guanidinovaleric acid. "Guanidinium" refers to the positively charged conjugate acid form. In the present invention, guanidino and guanidinium groups are both useful and are often used interchangeably.

"Amidinyl" and "amidino" refer to a moiety having the formula —C(=NH)(NH$_2$). "Amidinium" refers to the positively charged conjugate acid form.

The term "poly-arginine" or "poly-Arg" refers to a polymeric sequence composed of contiguous arginine residues; poly-L-arginine refers to all L-arginines; poly-D-arginine refers to all D-arginines. Poly-L-arginine is also abbreviated by an upper case "R" followed by the number of L-arginines in the peptide (e.g., R$^8$ represents an 8-mer of contiguous L-arginine residues); poly-D-arginine is abbreviated by a lower case "r" followed by the number of D-arginines in the peptide (r8 represents an 8-mer of contiguous D-arginine residues).

Amino acid residues are referred to herein by their full names or by standard single-letter or three-letter notations: A, Ala, alanine; C, Cys, cysteine; D, Asp, aspartic acid; E, Glu, glutamic acid; F, Phe, phenylalanine; G, Gly, glycine; H, His, histidine; I, Ile, isoleucine; K, Lys, lysine; L, Leu, leucine; M, Met, methionine; N, Asn, asparagine; P, Pro, proline; Q, Gln, glutamine; R, Arg, arginine; S, Ser, serine; T, Thr, threonine; V, Val, valine; W, Trp, tryptophan; X, Hyp, hydroxyproline; Y, Tyr, tyrosine.

II. Guanidinium Transport Reagents and Conjugates

A. General

The present invention provides a variety of transport reagents that are useful in enhancing the delivery of a biologically active agent to a particular site (e.g., into cells or across and into tissues such a epithelial tissue). The transport reagents and conjugates of the present invention contain oligomers or short-length polymers of from 6 to up to 50 subunits, a portion of which have attached guanidinium groups. The transport reagent is effective to enhance the transport rate of the conjugate (transport reagent-linking group-biological agent) across the biological membrane relative to the transport rate of the non-conjugated biological agent alone. Although in certain embodiments, the transport reagents contain peptides and/or amino acids, the invention is not so limited as the transport reagents contain non-peptide backbones and/or subunits as discussed further below.

The transport reagents of the present invention are generally constructed to provide suitable spacing between the guanidinium head groups. Suitable spacing can be accomplished by inserting non-guanidino containing subunits into the transport reagent, or by constructing guanidino-containing subunits that have longer backbone chains, thereby increasing the distance between the guanidinium head groups (when protonated).

FIG. 1 illustrates the general concept of the present transport reagents. As can be seen in this figure, either or both of W and T can be functional groups (e.g., amino, hydroxy, carboxylic acid and the like) or protected functional groups, linking groups that bear protected or unprotected functional groups, or linking groups having attached therapeutic agents. The subunit portions are also depicted and illustrate both guanidinium-containing subunits and spacing subunits. The portions of the subunits are also illustrated to provide structure for the terms backbone, sidechain and head group. Finally, a spaced guanidinium transport reagent formula is provided as an illustration of those reagents having equivalent spacing, though the invention is not so limited.

In view of the above, certain transport reagents can be depicted as oligomers of the following formulae: poly G*, (G*S$^p$G*)$_n$G*, (G*S$^p$)$_n$G*, (G*S$^p$S$^p$)$_n$G* and (G*S$^p$S$^p$S$^p$)$_n$G*. "G*" in the formulae is a guanidino-containing subunit and "S$^p$" is a subunit (or spacer) that does not contain a guanidino or amidino moiety. The subscript "n" is an integer ranging from 2 to 25. Oligomers having the spacings described have the advantage of being easily prepared in a blockwise fashion, that is, synthesizing groups such as, for example, G*S$^p$S$^p$ and linking them together to form a completed transport reagent.

In the above transport moiety formulae, the letter "S$^p$" can represent a natural or non-natural amino acid, or any other subunit described below that is devoid of a guanidino or amidino group. For those embodiments in which S$^p$ is an amino acid, the amino acid can be essentially any compound having (prior to incorporation into the transport moiety) an amino group (NH$_2$ or NH-alkyl) and a carboxylic acid group (CO$_2$H) and not containing either a guanidyl or amidinyl moiety. Examples of such compounds include D and L-alanine, D and L-cysteine, D and L-aspartic acid, D and L-glutamic acid, D and L-phenylalanine, glycine, D and L-histidine, D and L-isoleucine, D and L-lysine, D and L-leucine, D and L-methionine, D and L-asparagine, D and L-proline, D and L-glutamine, D and L-serine, D and L-threonine, D and L-valine, D and L-tryptophan, D and L-hydroxyproline, D and L-tyrosine, sarcosine, β-alanine, γ-amino butyric acid and ε-amino caproic acid. In each of the above formulae, each $S^p$ will be independent of any other $S^p$ present in the transport moiety, though in some embodiments, all $S^p$ groups can be the same.

In one group of preferred embodiments, the transport moiety has the formula $(G*S^pG*)_nG*$, wherein each "$S^p$" is independently selected from glycine, β-alanine, γ-amino butyric acid and ε-amino caproic acid, "$G*$" is preferably a carbamate, ethylenediamine, aza-amino acid, or a γ-amino acid, and n is preferably an integer ranging from 2 to 5. More preferably, each "$S^p$" is glycine or ε-amino caproic acid and n is 3. Within this group of embodiments, the use of glycine is preferred for those compositions in which the transport reagent is covalently attached directly to a polypeptide biological agent. For those embodiments in which the transport moiety is to be assembled using, for example, solid phase methods, ε-amino caproic acid is preferred.

In another group of preferred embodiments, the transport reagent has the formula $(G*S^p)_nG*$, wherein each "$S^p$" is preferably selected from glycine, β-alanine, γ-amino butyric acid and ε-amino caproic acid, "$G*$" is preferably a carbamate, ethylenediamine, aza-amino acid, or a γ-amino acid, and n is preferably an integer ranging from 3 to 10. More preferably, each "$S^p$" is glycine or ε-amino caproic acid and n is 3, 4, 5, or 6. As with the above group of specific embodiments, the use of glycine is preferred for those compositions in which the transport moiety is fused or covalently attached directly to a polypeptide biological agent such that the entire composition can be prepared by recombinant methods. For solution or solid phase construction of the transport moiety, ε-amino caproic acid is preferred.

In yet another group of preferred embodiments, the transport moiety has the formula $(G*S^pS^p)_nG*$, wherein each "$S^p$" is preferably selected from glycine, β-alanine, γ-amino butyric acid and α-amino caproic acid, "$G*$" is preferably a carbamate, ethylenediamine, aza-amino acid, or a γ-amino acid, and n is preferably an integer ranging from 4 to 10. More preferably, each "$S^p$" is glycine or γ-amino caproic acid and n is 6.

In still another group of preferred embodiments, the transport moiety has the formula $(G*S^pS^pS^p)_nG*$, wherein each "$S^p$" is preferably selected from glycine, β-alanine, γ-amino butyric acid and ε-amino caproic acid, "$G*$" is preferably a carbamate, ethylenediamine, aza-amino acid, or a γ-amino acid, and n is preferably an integer ranging from 4 to 10. More preferably, "$S^p$" is glycine and n is 6.

Although the spacing between adjacent sidechain moieties will usually be consistent from subunit to subunit (illustrated by the repeating nature of the groups above), the transport reagents used in the invention can also include variable spacing between sidechain moieties along the backbone.

In other embodiments, each of the $S^p$ groups will be selected to enhance certain desired properties of the transport moiety. For example, when transport moeities having a more hydrophobic character are desired, each $S^p$ can be selected from those naturally occuring amino acids that are typically grouped together as hydrophobic amino acids (e.g., phenylalanine, phenylglycine, valine, leucine, isoleucine). Similarly, transport reagents having a more hydrophilic character can be prepared when some or all of the $S^p$ groups are hydrophilic amino acids (e.g., lysine, serine, threonine, glutamic acid, and the like).

One of skill in the art will appreciate that the transport reagent can be of the formula $(G*S^pS^p)_nG*$ yet have additional amino acids which flank this moiety (e.g., $X_m(G*S^pS^p)_nG*-X_p$ wherein the subscripts m and p represent integers of zero to about 10 and each X is independently a natural or non-natural amino acid).

Thus, the transport moiety can be viewed as having certain peptide character in the sense that it can have a carboxy terminus and an amino terminus. At least one of the termini is preferably either covalently attached to a biologically active agent or, alternatively, to a linking group that is part of a transport reagent-linking group-biological agent conjugate. In other embodiments, the biologically active agent can be attached to the transport reagent via a linking group that is in turn attached to a sidechain functional group (e.g., the hydroxy group of a serine residue, the amino group of a lysine residue, the carboxylic acid group of a glutamic acid residue, and the like).

In an important aspect of the invention, the conjugates of the invention are particularly useful for transporting biologically active agents across cell or organelle membranes, when the agents are of the type that require trans-membrane transport to exhibit their biological effects, and that do not exhibit their biological effects primarily by binding to a surface receptor, i.e., such that entry of the agent does not occur. Further, the conjugates are particularly useful for transporting biologically active agents of the type that require trans-membrane transport to exhibit their biological effects, and that by themselves (without conjugation to a transport reagent or some other modification), are unable, or only poorly able, to enter cells to manifest biological activity.

As a general matter, the transport reagent used in the present conjugates preferably includes a linear backbone of subunits. The backbone will usually comprise atoms selected from carbon, nitrogen, oxygen, sulfur, and phosphorus, with the majority of backbone chain atoms usually being carbon. The subunits will optionally contain a sidechain moiety that includes a terminal guanidino or amidino group, although some subunits will not contain a guanidino or amidino group and are inserted into the backbone to provide spacing between the guanidino or amidino containing subunits that serves to facilitate uptake into a cell or across a tissue.

The sidechain moieties extend away from the backbone such that the central guanidino or amidino carbon atom (to which the $NH_2$ groups are attached) is linked to the backbone by a sidechain linker that preferably contains at least 2 linker chain atoms, more preferably from 2 to 7 chain atoms, such that the central carbon atom is the third to eighth chain atom away from the backbone. The chain atoms are preferably provided as methylene carbon atoms, although one or more other atoms such as oxygen, sulfur, or nitrogen can also be present. Preferably, the sidechain linker between the backbone and the central carbon atom of the guanidino or amidino group is 4, 5 or 6 chain atoms long, as exemplified by an arginine side chain (or homoarginine side chain, etc).

As noted above, the transport reagent of the invention can be flanked by one or more non-guanidino/non-amidino subunits (e.g., glycine, alanine or cysteine), or a linker such as an aminocaproic acid group, which does not significantly affect the rate of membrane transport of the corresponding transport reagent-linking group-biological agent conjugate. Also, any free amino terminal group can be capped with a blocking group or protecting group, such as an acetyl or benzyl group, to prevent ubiquitination in vivo.

The biological agent to be transported can be linked to the transport reagent according to a number of embodiments. In one preferred embodiment, the agent is linked to a single transport reagent, either via linkage to a terminal functional group on one end of the transport reagent or to an internal subunit within the polymer via a suitable linking group.

In a second embodiment, the agent is attached to more than one polymer, in the same manner as above. This embodiment is somewhat less preferred, since it can lead to crosslinking of adjacent cells.

In a third embodiment, the conjugate contains two agent moieties attached to each terminal end of the polymer. For this embodiment, it is preferred that the agent has a molecular weight of less than 10 kDa.

With regard to the first and third embodiments just mentioned, the agent is generally not attached to any one of the guanidino or amidino sidechains so that they are free to interact with the target membrane.

The conjugates of the invention can be prepared by straightforward synthetic schemes. Furthermore, the conjugate products are usually substantially homogeneous in length and composition, so that they provide greater consistency and reproducibility in their effects than heterogenous mixtures.

According to an important aspect of the present invention, it has been found by the applicants that attachment of a single transport reagent to any of a variety of types of biologically active agents is sufficient to substantially enhance the rate of uptake of an agent across biological membranes, even without requiring the presence of a large hydrophobic moiety in the conjugate. In fact, attaching a large hydrophobic moiety can significantly impede or prevent cross-membrane transport due to adhesion of the hydrophobic moiety to the lipid bilayer. Accordingly, the present invention includes conjugates that do not contain large hydrophobic moieties, such as lipid and fatty acid molecules.

B. Structural Features of the Transport Reagents and Conjugates

In view of the above discussion, the present invention provides in one group of embodiments, compounds having the formula:

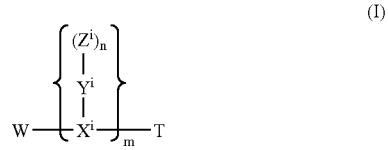

(I)

wherein the subscript m is an integer of from 6 to 50; T represents a protected or unprotected first terminal functional group, a protected or unprotected linking group, or a linking group having an attached biologically active agent; and W represents a protected or unprotected second terminal functional group, a protected or unprotected linking group, or a linking group having an attached therapeutic agent. In the subunit portion (enclosed by brackets), the subscript n can be 0, 1 or 2; each $X^i$ is a backbone subunit wherein the superscript i is an integer of from 1 to m and denotes the position downstream of W; each $Y^i$ is selected from H, an amino acid sidechain, aryl, and heteroaryl, when the subscript n is 0; or is selected from $(C_1–C_8)$alkylene, $(C_2–C_8)$alkenylene, $(C_2–C_8)$alkynylene, $(C_2–C_8)$heteroalkylene, $(C_3–C_8)$cycloalkylalkylene, $(C_2–C_8)$spirocycloalkylene, arylene, heteroarylene, and combinations thereof, when the subscript n is 1; each $Z^i$ is a guanidinium moiety, preferably selected from:

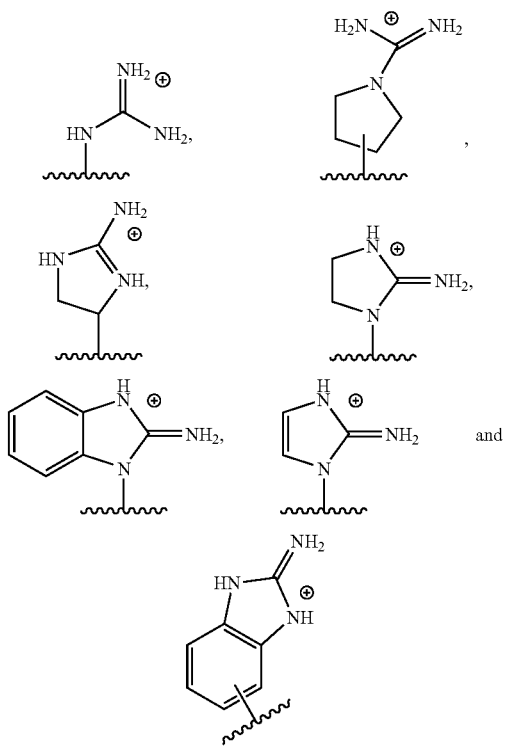

wherein the wavy line denotes the point of attachment to $Y^i$; and the subscript n is 0, 1 or 2, indicating the absence or presence of a Z guanidinium moiety at each i position; with the proviso that the compound has at least 6 guanidinium moieties that can be the same or different, and further include those moieties illustrated that have additional non-interfering substituents (e.g., alkyl, heteroalkyl and the like).

More particularly, W and T can be functional groups such as hydroxy, thiol, carboxy, carboxamide, aldehyde, amino and the like, that can be in a protected or unprotected form. Suitable protecting groups for various functional groups are described in, for example, Greene and Wuts, PROTECTIVE GROUPS IN ORGANIC SYNTHESIS, 2nd Ed., John Wiley & Sons, New York, N.Y., 1991. Additionally, either or both of T and W can be a linking group which is either a vestige of the attachment chemistry used during synthesis of the transport reagent on a solid support, or a linking group used to attach a therapeutic agent. For those embodiments in which either T or W is a linking group, or a linking group attached to a biologically active agent, the linking group is preferably one that is cleavable in vivo and results in release of the therapeutic agent from the transport reagent.

For biologically active agents that are inactive until the attached transport reagent is released, the linker is preferably a readily cleavable linker, meaning that it is susceptible to enzymatic or solvent-mediated cleavage in vivo. For this purpose, linkers containing carboxylic acid esters and disulfide bonds are preferred, where the former groups are hydrolyzed enzymatically or chemically, and the latter are severed by disulfide exchange, e.g., in the presence of glutathione.

In one preferred embodiment, the cleavable linker contains a first cleavable group that is distal to the agent, and a second cleavable group that is proximal to the agent, such that cleavage of the first cleavable group yields a linker-agent conjugate containing a nucleophilic moiety capable of reacting intramolecularly to cleave the second cleavable group, thereby releasing the agent from the linker and polymer. This embodiment is further illustrated by the various small molecule conjugates discussed below.

A more complete discussion of the components of this aspect of the invention is presented below.

C. Transport Reagent Components

Figure 3:
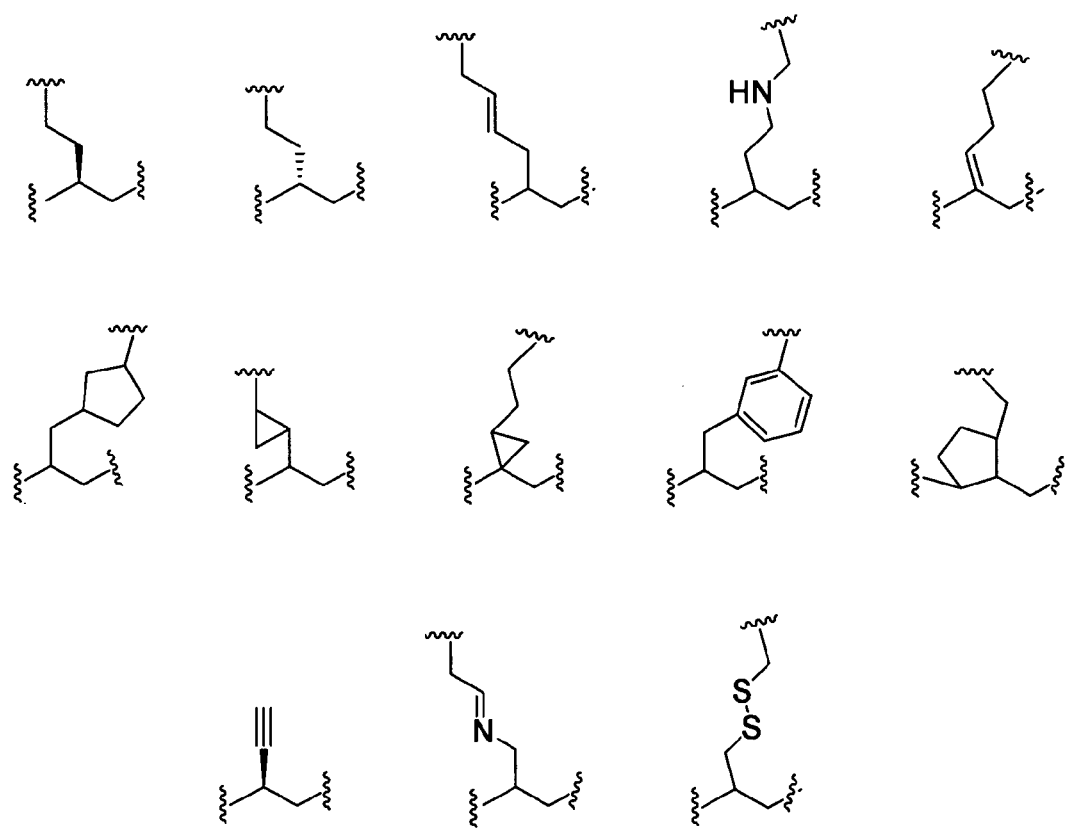
FIG. 3 illustrates a number of sidechain moieties having stereochemistry, sites of unsaturation, heteroatoms, and cyclic forms (including aromatic groups).
Figure 5A:
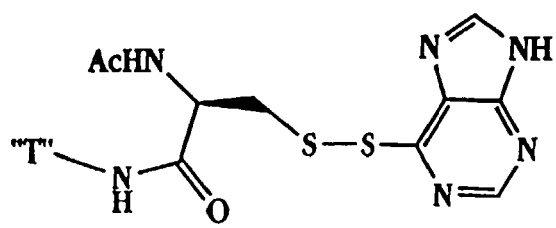
FIGS. 5A, 5B, 5C and 5D illustrate conjugates employing different types of linking groups.
Figure 5B:
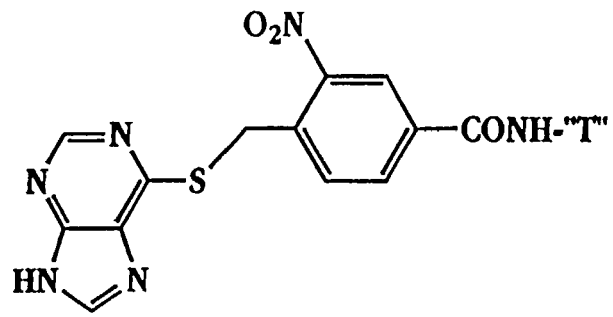
Figure 5C:
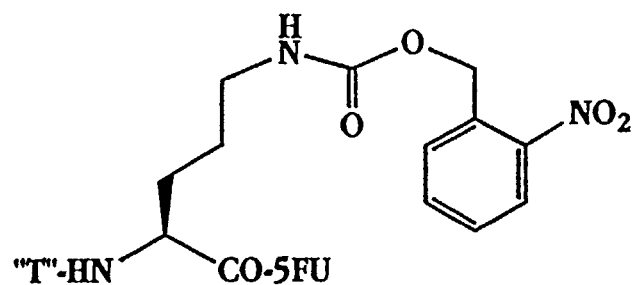
Figure 5D:
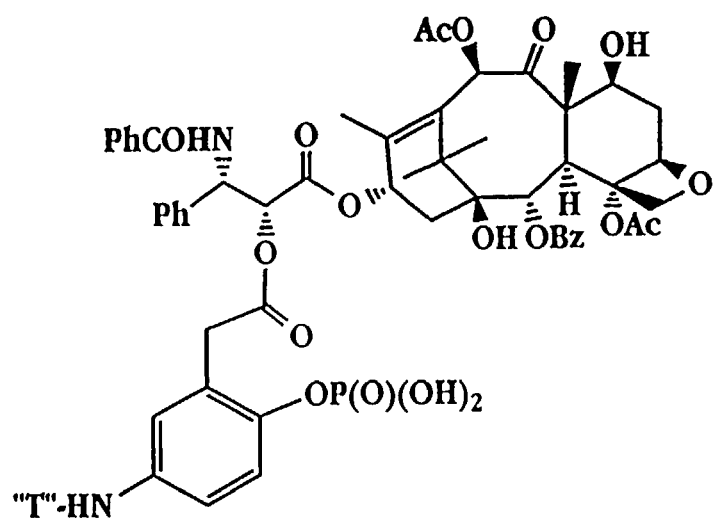

The transport reagents of the present invention (e.g., compounds of formula I wherein W and T are protected or unprotected terminal functional groups) can contain a number of different subunits, including amino acids. In general, however, the reagents and conjugates are not prepared entirely from naturally-occurring amino acids. Additionally, the transport reagents include a backbone component, a guandinium head group component (see FIG. 2) and a sidechain component that links that backbone and headgroup (see FIG. 3).

Amino acids. In one embodiment, the transport reagent includes D or L amino acid residues (e.g, some of —$X^i$(—$Y^i$—$(Z^i)_n$) are amino acids). Use of naturally occurring L-amino acid residues in the transport reagents has the advantage that break-down products should be relatively non-toxic to the cell or organism. Preferred amino acid subunits are arginine α-amino-δ-guanidinovaleric acid) and α-amino-ϵ-amidino-hexanoic acid (isosteric amidino analog). The guanidinium group in arginine has a pKa of about 12.5.

More generally, it is preferred that each polymer subunit contains a highly basic sidechain moiety which (i) has a pKa of greater than 11, more preferably 12.5 or greater, and (ii) contains, in its protonated state, at least two geminal amino groups ($NH_2$) which share a resonance-stabilized positive charge, which gives the moiety a bidentate character.

Other amino acids, such as α-amino-β-guanidino-propionic acid, α-amino-γ-guanidino-butyric acid, or α-amino-ϵ-guanidino-caproic acid can also be used (containing 2, 3 or 5 linker atoms, respectively, between the backbone chain and the central guanidinium carbon).

D-amino acids may also be used in the transport reagents. Compositions containing exclusively D-amino acids have the advantage of decreased enzymatic degradation. However, they may also remain largely intact within the target cell. Such stability is generally not problematic if the agent is biologically active when the polymer is still attached. For agents that are inactive in conjugate form, a linker that is cleavable at the site of action (e.g., by enzyme- or solvent-mediated cleavage within a cell) should be included within the conjugate to promote release of the agent in cells or organelles.

Other Subunits. Subunits other than amino acids may also be selected for use in forming transport reagents. Such subunits may include, but are not limited to hydroxy amino acids, N-methyl-amino acids, amino aldehydes, and the like, which result in polymers with reduced peptide bonds. Still other subunit types can be used, depending on the nature of the selected backbone, as discussed in the next section.

i. Backbone Type

A variety of backbone subunits and types (e.g., $X^i$ components) can be used to order and position the sidechain guanidino and/or amidino moieties. The term "backbone subunit" is generally meant to include any 2 to 8 atom linear linkage that is optionally substituted and/or has heteroatoms as members of the 2 to 8 atom chain. For example, backbone subunits include, alkylene backbone moieties joined by thioethers or sulfonyl groups, hydroxy acid esters (equivalent to replacing amide linkages with ester linkages), replacing the α-carbon of an α-amino acid with nitrogen to form an aza analog, alkylene backbone moieties joined by carbamate groups, polyethyleneimines (PEIs), and amino aldehydes, which result in polymers composed of secondary amines.

A more detailed backbone list includes N-substituted amide (CONR replaces CONH linkages), esters ($CO_2$), ketomethylene ($COCH_2$) reduced or methyleneamino ($CH_2NH$), thioamide (CSNH), phosphinate ($PO_2RCH_2$), phosphonamidate and phosphonamidate ester ($PO_2RNH$), retropeptide (NHCO), trans-alkene (CR=CH), fluoroalkene (CF=CH), dimethylene ($CH_2CH_2$), thioether ($CH_2S$), hydroxyethylene ($CH(OH)CH_2$), methyleneoxy ($CH_2O$), tetrazole ($CN_4$), retrothioamide (NHCS), retroreduced ($NHCH_2$), sulfonamido ($SO_2NH$), methylenesulfonamido ($CHRSO_2NH$), retrosulfonamide ($NHSO_2$), and peptoids (N-substituted glycines), and backbones with malonate and/or gem-diaminoalkyl subunits, for example, as reviewed by Fletcher et al. (1998) and detailed by references cited therein. Peptoid backbones (N-substituted glycines) can also be used (e.g., Kessler, 1993; Zuckermann et al., 1992; and Simon et al., 1992). Many of the foregoing substitutions result in approximately isosteric polymer backbones relative to backbones formed from α-amino acids.

Returning to formula I, in each of the structures below, $Z^i$ represents a guanidino or guanidinium group ($Z^i$ in formula I) and $Y^i$ indicates a sidechain linking group (i.e., the linkage between $Z^i$ and $X^i$ in formula I). The scope of each of $Y^i$ and $Z^i$ is described in more detail below.

Structure I shows a portion of a peptide transport reagent in which amino acid subunits having attached guanidino groups (e.g., arginine, homoarginine) are separated by amino acids that do not contain guanidino groups (e.g., glycine). See, also co-pending application Ser. No. 10/078, 247, filed Feb. 14, 2002, published as Pub. No. 2003/0032593A1 on Feb. 13, 2003, and incorporated herein by reference. In structure II, a transport reagent comprising glycine subunits and N-functionalized glycine subunits is illustrated. As a result, structure II is a composite of a peptide/peptoid oligomer.

In a similar fashion, structure III is shown as a composite of glycine (non-guanidino containing) subunits and an aza-amino acid subunit having attached guanidino groups.

Structure IV illustrates an oligomer of hydroxamic acid subunits in which subunits bearing a guanidino group are separated from each other by non-guanidino containing hydroxamic acid subunits.

Structure V illustrates the use of an oligosaccharide backbone wherein a single guanidino group is attached to each of the sugar subunits.

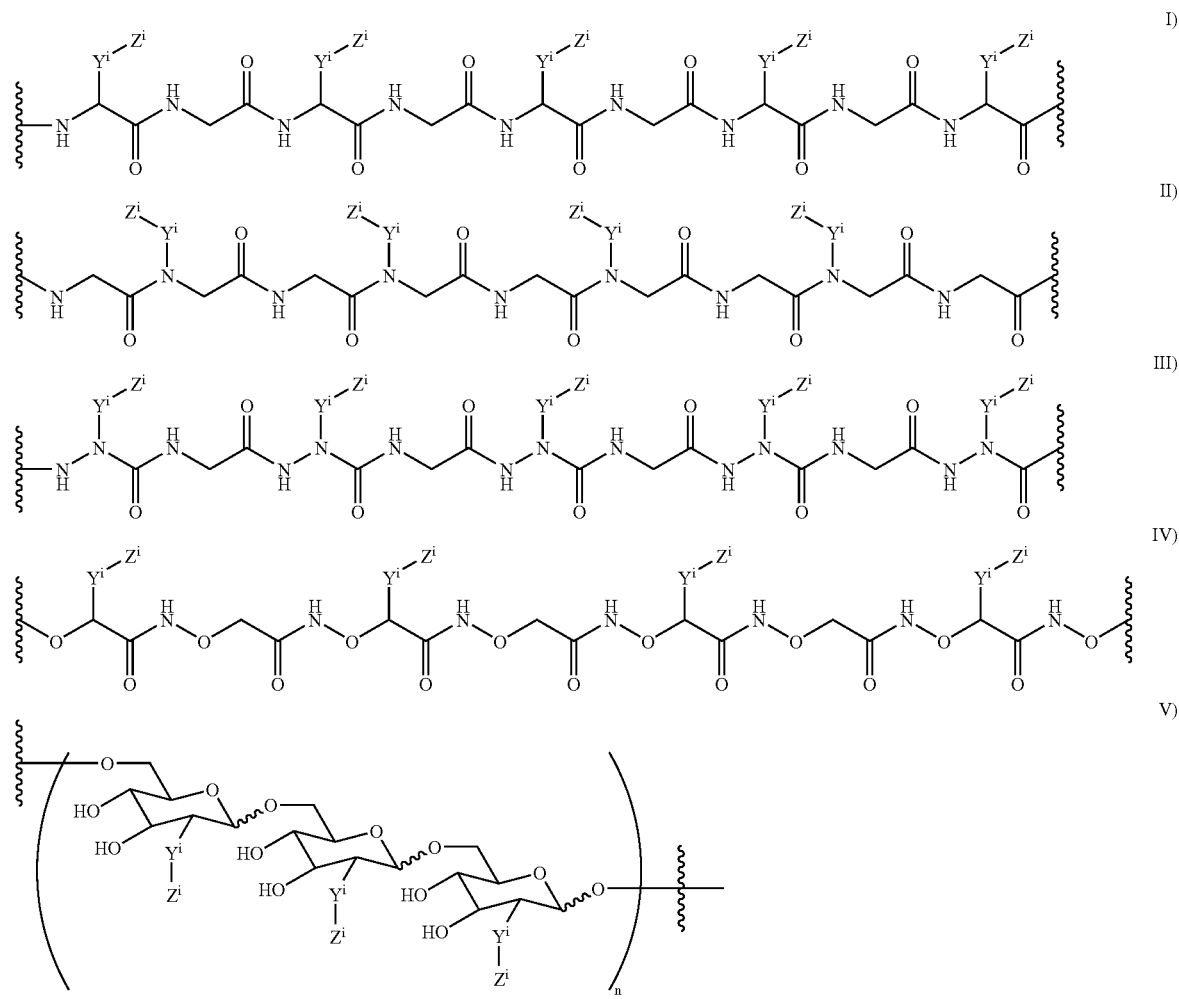

Structure VI illustrates an oligocarbamate transport reagent in which a guanidino group is attached to each of the monomeric subunits. In this group of embodiments, the separation between the guanidino groups is sufficient without the use of additional spacing groups. However, the invention contemplates those embodiments as well, wherein non-guanidino containing subunits (e.g., amino acids, protected aminoethyl carbonates, and the like) are incorporated.

Structure VII illustrates a polyamine transport reagent (the construction of which is shown below).

Structure VIII illustrates a transport reagent prepared from γ-amino acids. As with the carbamate transport reagents (see structure VI), each subunit is shown with an attached guanidino group, but additional amino acids (e.g., glycine, β-alanine, γ-aminobutryic acid, ε-aminocaproic acid, and the like) can be used to provide even greater spacing between the guanidino groups along the backbone.

Structure IX illustrates a "glutaramide" transport reagent in which the backbone consists of ethylene diamine units linked together by glutaric acid units. Preparation of these transport reagents is described below, along with the related "oxalamide" and "urea" linkages.

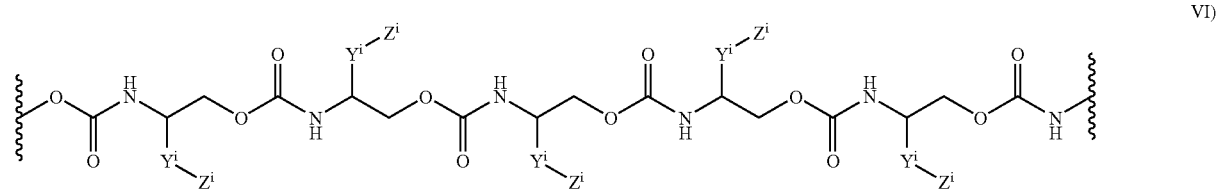

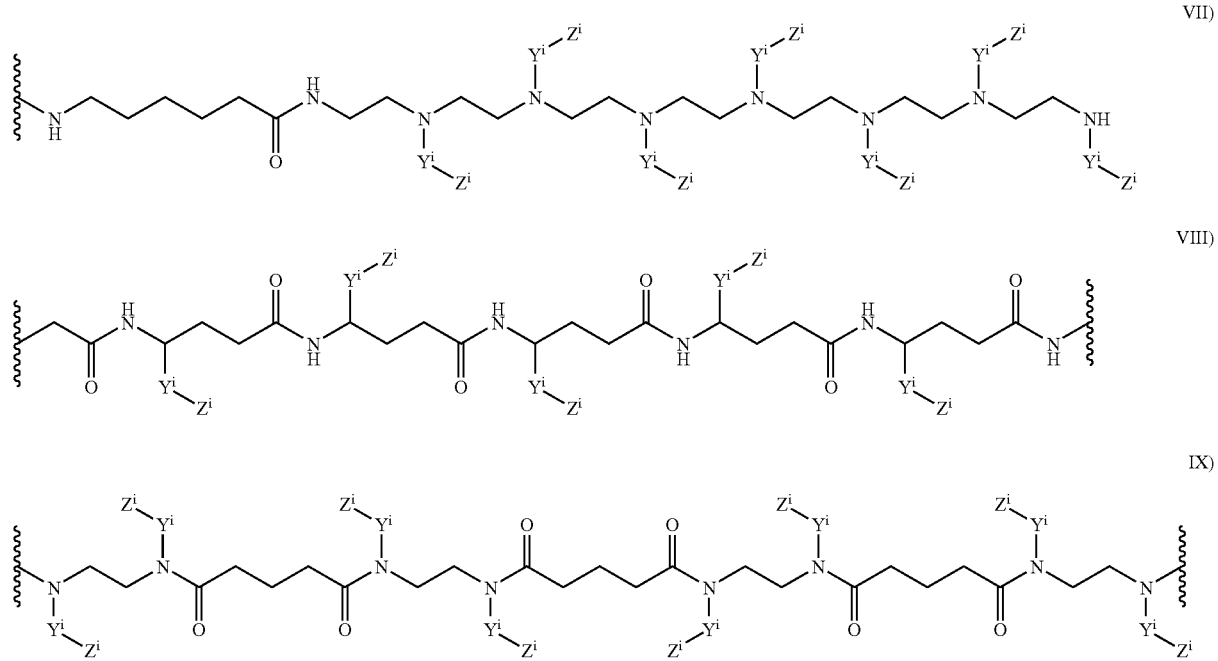

Studies carried out in support of the present invention have utilized both polypeptides (e.g., peptide backbones) and other backbones (e.g., carbamate transport reagents) and demonstrated that alternative backbones can provide enhanced delivery across a biological membrane and may also provide resistance to enzymatic degradation in vivo.

ii. Sidechain Linkages ($Y^i$)

In each of the above formulae, the group $Y^i$ indicates a linkage between the backbone and the guanidino or guanidinium head group ($Z^i$). A variety of linkages are contemplated by the present invention including ($C_1$–$C_8$)alkylene, ($C_2$–$C_8$)alkenylene, ($C_2$–$C_8$)alkynylene, ($C_2$–$C_8$)heteroalkylene, ($C_3$–$C_8$)cycloalkylalkylene, ($C_2$–$C_8$)spirocycloalkylene, arylene, heteroarylene, and combinations thereof. Members of these groups are illustrated below, using a guanidinium head group and a peptide backbone as a common feature to illustrate the various sidechain linkages.

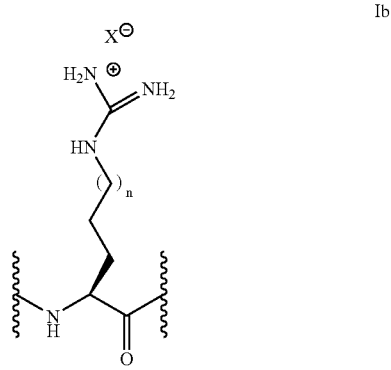

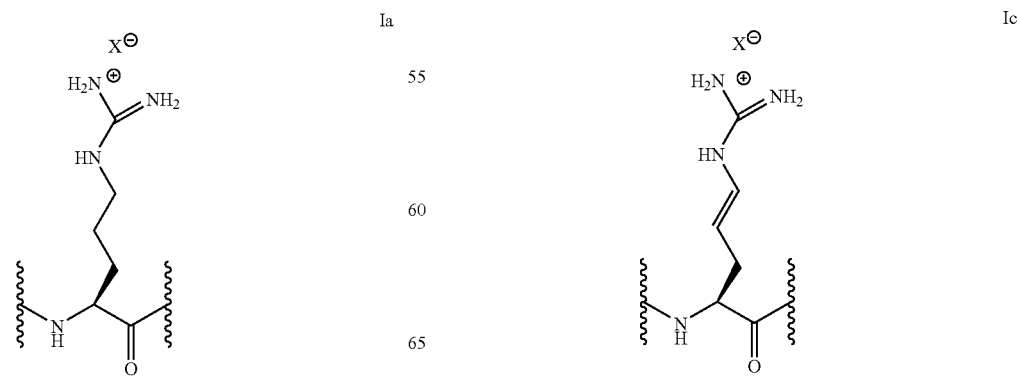

-continued
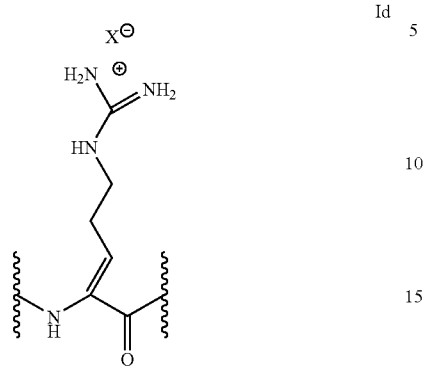
Id
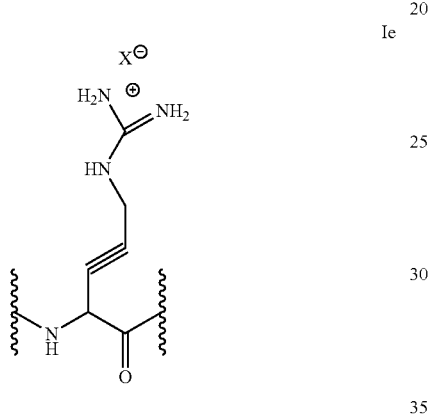
Ie
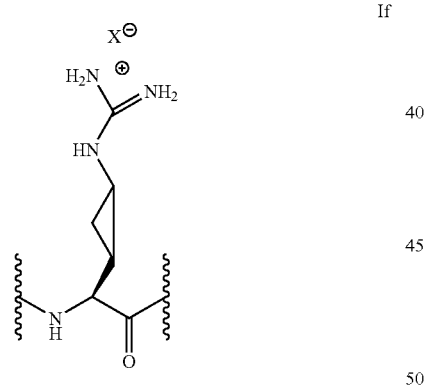
If
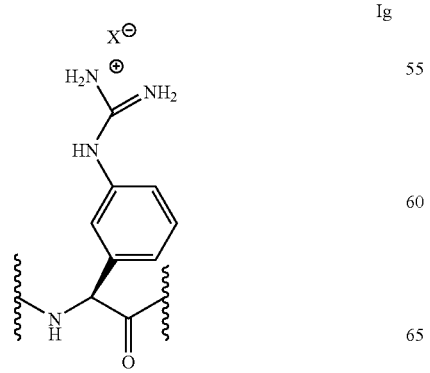
Ig
-continued
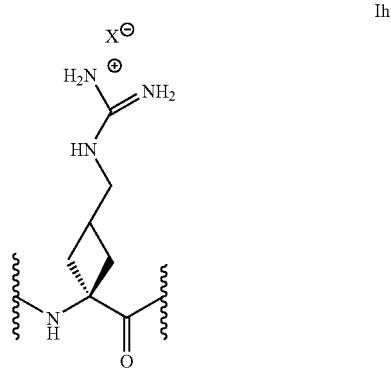
Ih
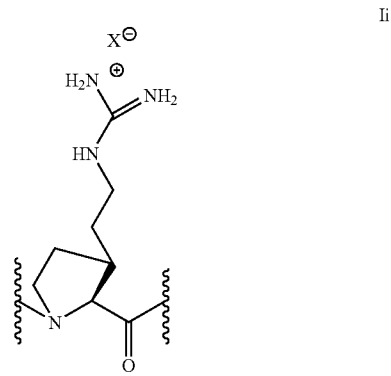
Ii
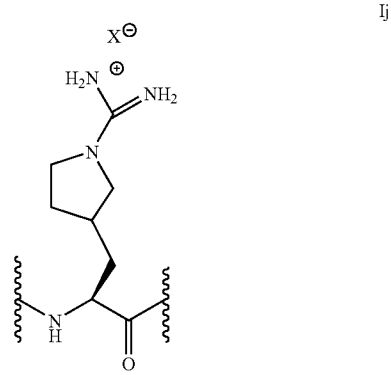
Ij
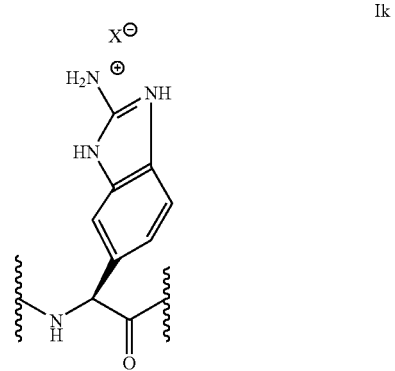
Ik As seen above, monomer Ia is a L-arginine subunit and the sidechain linking group is —CH$_2$CH$_2$CH$_2$—. Monomer Ib shows a subunit in which the sidechain linking group can be shorter (n=0) or longer (for example, n=2, 3, 4) than the sidechain linking group in arginine. Monomers Ic, Id and Ie illustrate sidechain linking groups that have sites of unsaturation. For those subunits in which the sidechain contains an alkene group, either orientation (E or Z, trans or cis) is contemplated by the present invention. The remaining monomers all show some portion of a cyclic structure as part of the sidechain linking group. In monomer If, a cyclopropane ring forms a linkage between the backbone and a guanidinium head group, providing a restriction on the conformational flexibility of the sidechain linking group. In monomer Ig, a phenyl ring is shown as the linking group between the backbone and the guanidino group. Related embodiments include those wherein other aryl groups or heteroaryl groups form the sidechain linking group (e.g., pyridine, pyridazine, naphthalene, biphenyl, and the like). Additionally, the linkage can be in a 1,3-(or meta) orientation as shown, or a 1,4-(or para) or 1,2-(or ortho) orientation, or any other orientation that serves to place the guanidino group in a position away from the steric encumbrance of the backbone. Additionally, the arylene or heteroarylene group sidechain linkages can have substituents that are selected to provide more or less electronic character to the guanidinium head group. For example, a nitro group substituent on a phenylene linking group can reduce the electronic character of the guanidinium head group, while an electron donating substituent (e.g., methoxy) can increase the electronic character of the guanidinium head group. Monomer Ih illustrates a linking group having a spirocyclic ring portion. A four-membered ring is shown in Ih, but other rings (3-, 5-, 6- and 7-membered carbocyclic and heterocyclic rings) are also within the scope of the invention. Monomer Ii illustrates a sidechain linking group in which a portion of the linking group forms a ring structure with a portion of the backbone to restrict the conformational freedom of the linking group and also the guanidinium head group. Monomer Ij illustrates a sidechain linking group having a five-membered ring in common with one nitrogen atom of the guanidinium head group, while monomer Ik illustrates the combination of a sidechain linking group and a guanidinium head group into a single 2-aminobenzimidazole moiety.

One of skill in the art will appreciate that additional embodiments are contemplated in which the sidechain linking groups contain heteroatoms as replacements for some of the carbon atoms shown, or where features of two or more of the monomers illustrated above are combined in a single sidechain linking group.

iii. Guanidinium Head Groups or Guanidino Groups ($Z^i$)

As with the sidechain linking groups described above, the present invention is directed to compositions wherein $Z^i$ represents a guanidino or guanidinium head group. Preferably, each $Z^i$ in the transport reagent is independently selected from

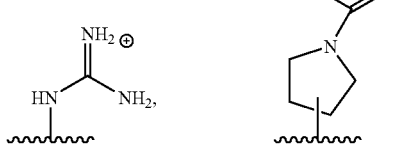

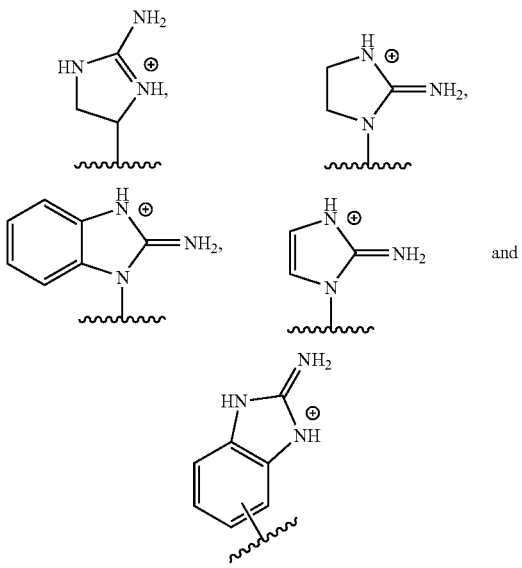

wherein the wavy line denotes the point of attachment to $Y^i$.

Still other useful $Z^i$ groups are

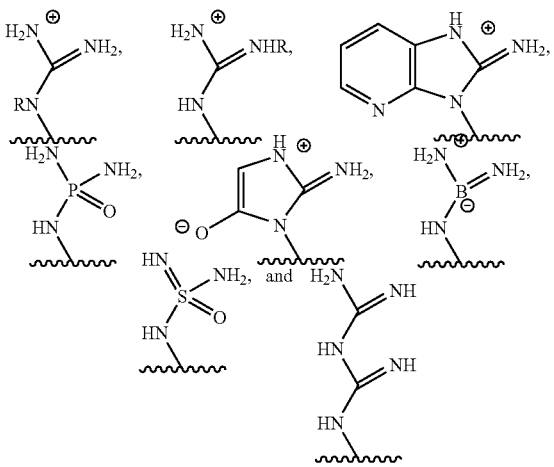

Monomers incorporating certain $Z^i$ groups from above are provided below. For example, suitable monomers in an amino acid backbone format include:

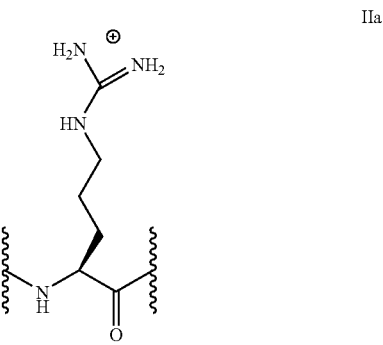

IIa

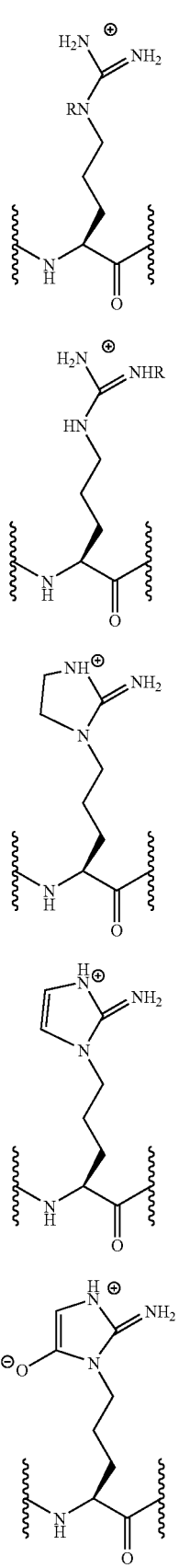
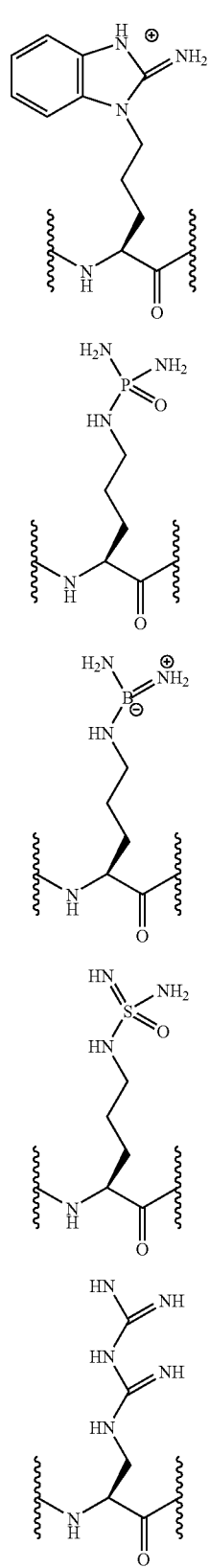
For reference to other monomers above, IIa is an arginine residue (shown in a positively charged form). Monomers IIb and IIc illustrate guanidino or guanidinium head groups that are substituted with R groups (R can be, for example, alkyl groups or arylalkyl groups). Monomers IId, IIe, IIf and IIg illustrate guanidino or guanidinium head groups in which the guanidinium moiety is part of a heterocyclic ring (optionally fused to a second ring, see IIg). Monomers IIh, IIi and IIj illustrate heteroatom analogs of guanidino head groups wherein the central carbon atom of the guanidino moiety is replaced by a heteroatom such as phosphorus, boron or sulfur (e.g., IIh, IIi and IIj, respectively). Monomer IIk illustrates a combined amidino/guanidinium head group, so that the monomer has electronic and steric characteristics similar to an arginine residue.

iv. Preferred Embodiments

Returning to formula I above, a number of embodiments are preferred for the transport reagents and their conjugates with biologically active agents.

In one group of preferred embodiments, each $X^i$ is independently selected from:

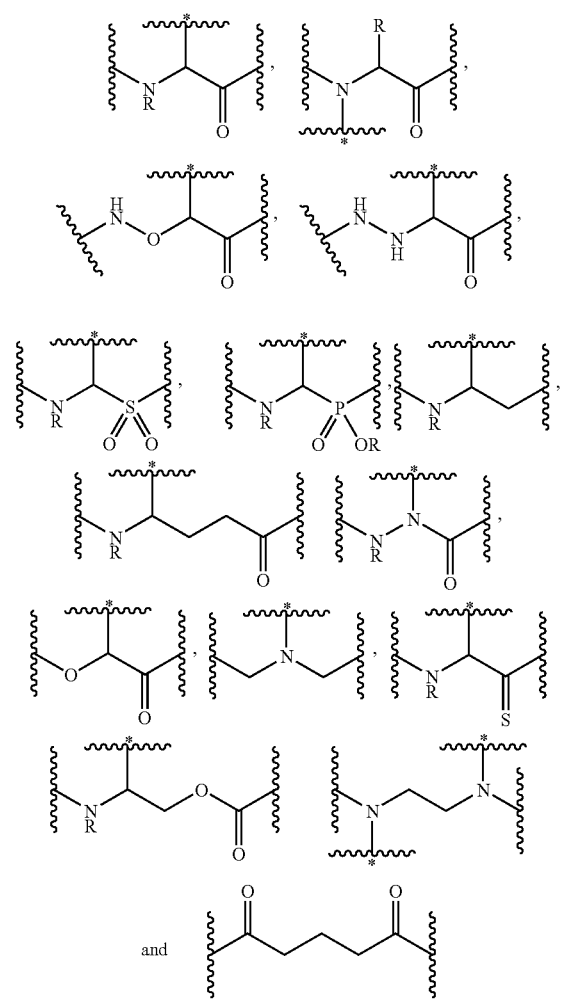

wherein each R is selected from H and an amino acid side chain (other than a side chain having an attached guanidino or amidino group, e.g., an arginine side chain); the starred wavy line indicates the point of attachment to $Y^i$ and the remaining wavy lines indicate the point of attachment along the backbone.

More preferably, $X^i$ is selected from:

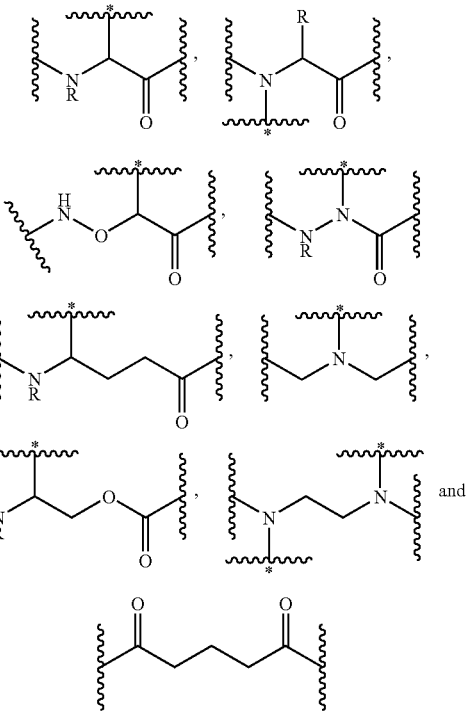

Still more preferably, the transport reagent comprises a non-peptide backbone wherein each $X^i$ is selected from:

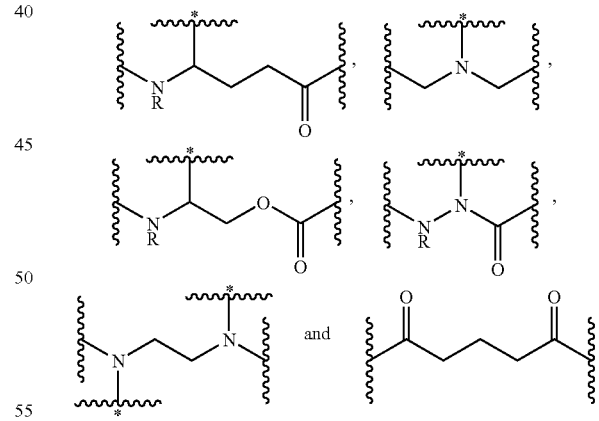

Returning to formula I, in one group of preferred embodiments, each $Y^i$ that is attached to a $Z^i$ is selected from $(C_1-C_8)$alkylene, $(C_2-C_8)$alkenylene, $(C_2-C_8)$heteroalkylene, $(C_3-C_8)$cycloalkylalkylene, arylene and combinations thereof. More preferably, each $Y^i$ that is attached to a $Z^i$ is an unbranched $(C_3-C_7)$alkylene.

Certain $Z^i$ groups are also preferred in the present invention. In one group of preferred embodiments, each $Z^i$ is selected from:

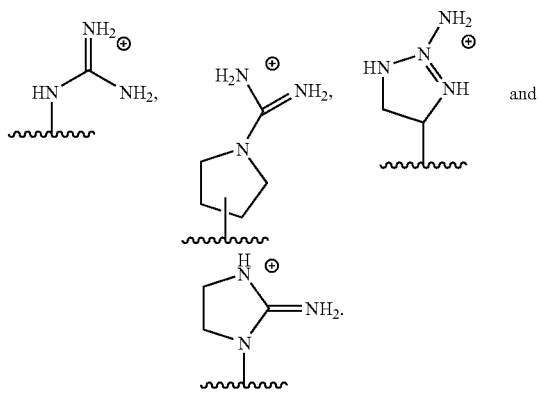

In still other preferred embodiments, each $Y^i$ that is attached to a $Z^1$ is an unbranched $(C_4-C_6)$alkylene and each $Z^i$ is —NH—C(=NH)—NH$_2$.

In yet another group of preferred embodiments, for each odd integer i in formula I, n is 0; and for each even integer i, n is 1.

In another group of preferred embodiments, m is an integer of from 12 to 25, and the compound has from 6 to 8 guanidinium moieties that can be the same or different.

In still other preferred embodiments, the transport reagent comprises the structures I–IX, provided above.

D. Biologically Active Agents

In some embodiments, the transport reagents are linked to a biologically active agent. A variety of biologically active agents are useful in this invention, including, but not limited to, small organic molecules (e.g., therapeutic agents), metal ions (typically conjugated as their chelates), macromolecules, peptides, diagnostic or imaging agents, and boron reagents.

i. Small Organic Molecules

Small organic molecule therapeutic agents (those agents having a molecular weight of from about 100 to about 1000) may be advantageously attached to linear polymeric compositions as described herein, to facilitate or enhance transport across biological membranes. For example, delivery of highly charged agents, such as levodopa (L-3,4-dihydroxyphenylalanine; L-DOPA) may benefit by linkage to polymeric transport molecules as described herein. Peptoid and peptidomimetic agents are also contemplated (e.g., Langston, 1997; Giannis et al., 1997). Also, the invention is advantageous for delivering small organic molecules that have poor solubilities in aqueous liquids, such as serum and aqueous saline. Thus, compounds whose therapeutic efficacies are limited by their low solubilities can be administered in greater dosages according to the present invention, and can be more efficacious on a molar basis in conjugate form, relative to the non-conjugate form, due to higher uptake levels by cells.

Still other therapeutic agents that can be attached to the transport reagent can be selected from known antibacterial agents, antifungal agents, antiviral agents, antiproliferative agents, immunosuppressive agents, vitamins, analgesics, hormones and the like.

Antibacterial agents useful in the present compositions and methods include in general the β-lactam antibiotics and the quinolone antibiotics. More particularly, the agents can be nafcillin, oxacillin, penicillin, amoxacillin, ampicillin, cefotaxime, ceftriaxone, rifampin, minocycline, ciprofloxacin, norfloxacin, erythromycin, vancomycin, or an analog thereof.

Antimicrobial agents useful in the present compositions and methods include in general sulfanilamide, sulfamethoxazole, sulfacetamide, sulfisoxazole, sulfadiazine, penicillins (e.g., penecillins G and V, methicillin, oxacillin, naficillin, ampicillin amoxacillin, carbenicillin, ticarcillin, mezlocillin and piperacillin), cephalosporins (e.g., cephalothin, cefaxolin, cephalexin, cefadroxil, cefamandole, cefoxitin, cefaclor, cefuroxine, loracarbef, cefonicid, cefotetan, ceforamide,cefotaxime, cefpodoxime proxetil, ceftizoxime, cefoperazone, ceftazidime and cefepime), aminoglycosides (e.g., gentamycin, tobramycin, amikacin, netilmicin, neomycin, kanamycin, streptomycin, and the like), tetracyclines (e.g., chlortetracycline, oxytetracycline, demeclocycline, methacycline, doxycycline and minocycline), and macrolides (e.g., erythromycin, clarithromycin, azithromycin).

Antifungal agents useful in the present compositions and methods include in general amphotericin, itraconazole, ketoconazole, miconazole, nystatin, clotrimazole, fluconazole, ciclopirox, econazole, naftifine, terbinafine and griseofulvin.

Antiviral agents useful in the present compositions and methods include in general acyclovir, famciclovir, ganciclovir, foscamet, idoxuridine, sorivudine, trifluridine, valacyclovir, cidofovir, didanosine, stavudine, zalcitabine, zidovudine, ribavirin and rimantatine.

Antiproliferative and immunosuppressive agents which are useful in the present compositions and methods include methotrexate, azathioprine, fluorouracil, hydroxyurea, 6-thioguanine, chclophosphamide, mechloroethamine hydrochloride, carmustine, cyclosporine, taxol, tacrolimus, vinblastine, dapsone and sulfasalazine.

Histamine receptor agonists and antagonists are another class of agents useful in the present invention. Examples of suitable agents include, 2-methylhistamine, 2-pyridylethylamine, 2-thiazolylethylamine, (R)-α-methylhistamine, impromidine, dimaprit, 4(5)methylhistamine, diphenhydramine, pyrilamine, promethazine, chlorpheniramine, chlorcyclizine, terfenadine, and the like.

Another class of agents useful in the present invention are compounds used in treating asthma. Examples of such agents include the corticosteroids (e.g., beclomethasone, budesonide and prednisone), cromolyn, nedocromil, albuterol, bitolterol mesylate, pirbuterol, salmeterol, terbutyline and theophylline.

Yet another class of biologically active agents which are useful in the present compositions and methods are the vitamins (see GOODMAN & GILMAN's THE PHARMACOLOGICAL BASIS OF THERAPEUTICS, Ninth Ed. Hardman, et al., eds. McGraw-Hill, p. 1547–1590 (1996)).

A variety of analgesic agents are useful in the present invention including, for example, lidocaine, bupivacaine, novocaine, procaine, tetracaine, benzocaine, cocaine, mepivacaine, etidocaine, proparacaine ropivacaine, prilocaine and the like.

Antineoplastic agents useful in the present compositions and methods include in general pentostatin, 6-mercaptopurine, 6-thioguanine, methotrexate, bleomycins, etoposide, teniposide, dactinomycin, daunorubicin, doxorubicin, mitoxantrone, hydroxyurea, 5-fluorouracil, cytarabine, fludarabine, mitomycin, cisplatin, procarbazine, dacarbazine, paclitaxel, colchicine, the vinca alkaloids, and the like.

ii. Metals

Metals can be transported into eukaryotic and prokaryotic cells using chelating agents such as texaphyrin or diethylene triamine pentacetic acid (DTPA), conjugated to a transporter of the invention. These conjugates are useful for delivering metal ions for imaging or therapy. Exemplary metal ions include Eu, Lu, Pr, Gd, $^{99m}$Tc, $^{67}$Ga, $^{111}$In, $^{90}$Y, $^{67}$Cu, and $^{57}$Co. Preliminary membrane-transport studies with conjugate candidates can be performed using cell-based assays. For example, using europium ions, cellular uptake can be monitored by time-resolved fluorescence measurements. For metal ions that are cytotoxic, uptake can be monitored by cytotoxicity.

iii. Macromolecules

The enhanced transport method of the invention is particularly suited for enhancing transport across biological membranes for a number of macromolecules, including, but not limited to proteins, nucleic acids, polysaccharides, and analogs thereof. Examplary nucleic acids include oligonucleotides and polynucleotides formed of DNA and RNA, and analogs thereof, which have selected sequences designed for hybridization to complementary targets (e.g., antisense sequences for single- or double-stranded targets), or for expressing nucleic acid transcripts or proteins encoded by the sequences. Analogs include charged and preferably uncharged backbone analogs, such as phosphonates (preferably methyl phosphonates), phosphoramidates (N3' or N5'), thiophosphates, uncharged morpholino-based polymers, and protein nucleic acids (PNAs). Such molecules can be used in a variety of therapeutic regimens, including enzyme replacement therapy, gene therapy, and anti-sense therapy, for example.

By way of example, protein nucleic acids (PNA) are analogs of DNA in which the backbone is structurally similar to a deoxyribose backbone. The backbone consists of N-(2-aminoethyl)glycine units to which the nucleobases are attached. PNAs containing all four natural nucleobases hybridize to complementary oligonucleotides obeying Watson-Crick base-pairing rules, and are true DNA mimics in terms of base pair recognition (Egholm et al., 1993). The backbone of a PNA is formed by peptide bonds rather than phosphate esters, making it well-suited for anti-sense applications. Since the backbone is uncharged, PNA/DNA or PNA/RNA duplexes that form exhibit greater than normal thermal stability. PNAs have the additional advantage that they are not recognized by nucleases or proteases. In addition, PNAs can be synthesized on an automated peptides synthesizer using standard t-Boc chemistry. The PNA is then readily linked to a transport reagent of the invention.

Examples of anti-sense oligonucleotides whose transport into cells may be enhanced using the methods of the invention are described, for example, in U.S. Pat. No. 5,594,122. Such oligonucleotides are targeted to treat human immunodeficiency virus (HIV). Conjugation of a transport reagent to an anti-sense oligonucleotide can be effected, for example, by forming an amide linkage between the peptide and the 5'-terminus of the oligonucleotide through a succinate linker, according to well-established methods.

Another class of macromolecules that can be transported across biological membranes is exemplified by proteins, and in particular, enzymes. Therapeutic proteins include, but are not limited to replacement enzymes. Therapeutic enzymes include, but are not limited to, alglucerase, for use in treating lysozomal glucocerebrosidase deficiency (Gaucher's disease), alpha-L-iduronidase, for use in treating mucopolysaccharidosis I, alpha-N-acetylglucosamidase, for use in treating sanfilippo B syndrome, lipase, for use in treating pancreatic insufficiency, adenosine deaminase, for use in treating severe combined immunodeficiency syndrome, and triose phosphate isomerase, for use in treating neuro-muscular dysfunction associated with triose phosphate isomerase deficiency.

In addition, and according to an important aspect of the invention, protein antigens may be delivered to the cytosolic compartment of antigen-presenting cells (APCs), where they are degraded into peptides. The peptides are then transported into the endoplasmic reticulum, where they associate with nascent HLA class I molecules and are displayed on the cell surface. Such "activated" APCs can serve as inducers of class I restricted antigen-specific cytotoxic T-lymphocytes (CTLs), which then proceed to recognize and destroy cells displaying the particular antigen. APCs that are able to carry out this process include, but are not limited to, certain macrophages, B cells and dendritic cells. In one embodiment, the protein antigen is a tumor antigen for eliciting or promoting an immune response against tumor cells.

The transport of isolated or soluble proteins into the cytosol of APC with subsequent activation of CTL is exceptional, since, with few exceptions, injection of isolated or soluble proteins does not result either in activation of APC or induction of CTLs. Thus, antigens that are conjugated to the transport enhancing compositions of the present invention may serve to stimulate a cellular immune response in vitro or in vivo.

In another embodiment, the invention is useful for delivering immunospecific antibodies or antibody fragments to the cytosol to interfere with deleterious biological processes such as microbial infection. Recent experiments have shown that intracellular antibodies can be effective antiviral agents in plant and mammalian cells (e.g., Tavladoraki et al., 1993; and Shaheen et al., 1996). These methods have typically used single-chain variable region fragments (scFv), in which the antibody heavy and light chains are synthesized as a single polypeptide. The variable heavy and light chains are usually separated by a flexible linker peptide (e.g., of 15 amino acids) to yield a 28 kDa molecule that retains the high affinity ligand binding site. The principal obstacle to wide application of this technology has been efficiency of uptake into infected cells. But by attaching transport reagents to scFv fragments, the degree of cellular uptake can be increased, allowing the immunospecific fragments to bind and disable important microbial components, such as HIV Rev, HIV reverse transcriptase, and integrase proteins.

iv. Peptides

Peptides to be delivered by the enhanced transport methods described herein include, but should not be limited to, effector polypeptides, receptor fragments, and the like. Examples include peptides having phosphorylation sites used by proteins mediating intra-cellular signals. Examples of such proteins include, but are not limited to, protein kinase C, RAF-1, p21Ras, NF-κB, C-JUN, and cytoplasmic tails of membrane, receptors such as IL-4 receptor, CD28, CTLA-4, V7, and MHC Class I and Class II antigens.

When the transport enhancing molecule is also a peptide, synthesis can be achieved either using an automated peptide synthesizer or by recombinant methods in which a polynucleotide encoding a fusion peptide is produced, as mentioned above.

v. Diagnostic Imaging and Contrast Agents

The compositions of the present invention are also useful for delivery of diagnostic imaging and contrast agents into and across one or more layers of an epithelial and/or endothelial tissue. Examples of diagnostic agents include substances that are labeled with radioactivity, such as $^{99m}$Tc glucoheptonate, or substances used in magnetic resonance imaging (MRI) procedures such as gadolinium doped chelation agents (e.g. Gd-DTPA). Other examples of diagnostic agents include marker genes that encode proteins that are readily detectable when expressed in a cell, including but not limited to, β-galactosidase, green fluorescent protein, luciferase, and the like. A wide variety of labels may be employed, such as radionuclides, fluors, enzymes, enzyme substrates, enzyme cofactors, enzyme inhibitors, ligands (particularly haptens), and the like.

vi. Boron Reagents

The compositions and methods of the present invention are also useful for delivery of boron reagents such as those used in Boron Neutron Capture therapy. In this embodiment, the boron species can be incorporated into the delivery enhancing transport reagent itself or can be combined with the transport reagent to more efficiently transfer the boron into a target cell or tissue. Reviews on Boron Neutron Capture can be found as follows: Barth, et al., *Mol. Chem. Neuropathol.* 21:139–154 (1994); Barth, et al., *Cancer Inv.* 14:534–550 (1996); Coderre, et al., *Radiat. Res.* 151:1–18 (1999); Gahbauer, et al., *Recent Results Cancer Res.* 150: 183–209 (1998); Hawthorne, *Angew. Chem., Int. Ed. Engl.* 32:950–984 (1993); Hawthorne, *Mol. Med. Today* 4:174–181 (1998); Soloway, et al., *J. Neuro-Oncol.* 33:9–18 (1997); Soloway, et al., *Chem. Rev.* 98:1515–1562 (1998). For a review on methods to prepare and incorporate boron in amino acids and peptides, see Spielvogel, et al., *Phosphorus, Sulfur, Silicon Relat. Elem.* 87:267–276 (1994). See also, Cai, et al., *J. Med. Chem.* 40:3887–3896 (1997).

E. Linking Groups for Attaching Biologically Active Agents to Transport Reagents The agent to be transported can be linked to the transport reagent according to a number of embodiments. In one embodiment, the agent is linked to a single transport reagent, either via linkage to a terminal end of the transport reagent or to an internal subunit within the reagent via a suitable linking group.

In a second embodiment, the agent is attached to more than one transport reagent, in the same manner as above. This embodiment is somewhat less preferred, since it can lead to crosslinking of adjacent cells.

In a third embodiment, the conjugate contains two biologically active agents (either the same or different) attached to each terminal end of the transport reagent. For this embodiment, it is presently preferred that the agent has a molecular weight of less than 10 kDa, more preferably, less than about 1 kDa.

With regard to the first and third embodiments just mentioned, the biologically active agent is generally not attached to one any of the guanidino or amidino sidechains so that they are free to interact with the target membrane. A variety of linking groups can be used to covalently attach the biologically active agent to the transport moiety, including essentially any of the commerically available bifunctional linking groups, preferably, heterobifunctional linking groups (see Pierce Catalog). When the linking groups have the same functional groups on either end, the groups will preferably be orthogonally protected so that each protecting group can be removed, while leaving the remaining protecting group intact. FIG. 5 illustrates a few linking groups that are useful in the present invention.

The conjugates of the invention can be prepared by straightforward synthetic schemes. Furthermore, the conjugate products are preferably substantially homogeneous in length and composition, so that they provide greater consistency and reproducibility in their effects than heterogeneous mixtures. More preferably, the compositions are at least 90% homogeneous (in transport conjugates), and most preferably at least about 99% homogeneous.

Transport reagents of the invention can be attached covalently to biologically active agents by chemical or recombinant methods. Chemical methods are preferred.

i. Chemical Linkages

Biologically active agents such as small organic molecules and macromolecules can be linked to transport reagents of the invention via a number of methods known in the art (see, for example, Wong, S. S., Ed., *Chemistry of Protein Conjugation and Cross-Linking*, CRC Press, Inc., Boca Raton, Fla. (1991), either directly (e.g., with a carbodiimide) or via a linking moiety. In particular, carbamate, ester, thioether, disulfide, and hydrazone linkages are generally easy to form and suitable for most applications. Ester and disulfide linkages are preferred if the linkage is to be readily degraded in the cytosol, after transport of the biologically active agent across a cell membrane.

Various functional groups (hydroxyl, amino, halogen, etc.) can be used to attach the biologically active agent to the transport reagent. Groups which are not known to be part of an active site of the biologically active agent are preferred, particularly if the transport reagent or any portion thereof is to remain attached to the biologically active agent after delivery.

A number of transport reagents can be prepared on a solid support and are conveniently produced with an amino terminal group and a protecting group, such as FMOC. For biologically active agents which can survive the conditions used to cleave the reagent from the synthesis resin and deprotect the sidechains, the FMOC may be cleaved from the N-terminus of the completed resin-bound reagent so that the biologically active agent can be linked to the free N-terminal amine. In such cases, the agent to be attached is typically activated by methods well known in the art to produce an active ester or active carbonate moiety effective to form an amide or carbamate linkage, respectively, with the transport reagent's amino group. Of course, other linking chemistries can also be used.

To help minimize side-reactions, guanidino and amidino moieties can be blocked using conventional protecting groups, such as carbobenzyloxy groups (CBZ), di-t-BOC, PMC, Pbf, N—$NO_2$, and the like.

Coupling reactions are performed by known coupling methods in any of an array of solvents, such as N,N-dimethyl formamide (DMF), N-methylpyrrolidinone, dichloromethane, water, and the like. Exemplary coupling reagents include, for example, O-benzotriazolyloxy tetramethyluronium hexafluorophosphate (HATU), dicyclohexyl carbodiimide, bromo-tris(pyrrolidino) phosphonium bromide (PyBroP), etc. Other reagents can be included, such as N,N-dimethylamino pyridine (DMAP), 4-pyrrolidino pyridine, N-hydroxy succinimide, N-hydroxy benzotriazole, and the like.

ii. Releasable Linkers

The biologically active agents are, in presently preferred embodiments, attached to the transport reagent using a linkage that is specifically cleavable or releasable. The use of such linkages is particularly important for biologically active agents that are inactive until the attached transport reagent is released. In some cases, such conjugates that consist of a drug molecule that is attached to a transport reagent can be referred to as prodrugs, in that the release of the transport reagent from the drug results in conversion of the drug from an inactive to an active form. As used herein, "cleaved" or "cleavage" of a conjugate or linker refers to release of a biological agent from a transport reagent molecule, thereby releasing an active biological agent. "Specifically cleavable" or "specifically releasable" refers to the linkage between the transport reagent and the agent being cleaved, rather than the transport reagent being degraded (e.g., by proteolytic degradation).

In some embodiments, the linkage is a readily cleavable linkage, meaning that it is susceptible to cleavage under conditions found in vivo. Thus, upon passing into and through one or more layers of an epithelial and/or endothelial tissue, the agent is released from the transport reagent. Readily cleavable linkages can be, for example, linkages that are cleaved by an enzyme having a specific activity (e.g., an esterase, protease, phosphatase, peptidase, and the like) or by hydrolysis. For this purpose, linkers containing carboxylic acid esters and disulfide bonds are sometimes preferred, where the former groups are hydrolyzed enzymatically or chemically, and the latter are severed by disulfide exchange, e.g., in the presence of glutathione. The linkage can be selected so it is cleavable by an enzymatic activity that is known to be present in one or more layers of an epithelial or endothelial tissue. For example, the stratum granulosum of skin has a relatively high concentration of N-peptidase activity.

A specifically cleavable linker can be engineered onto a transport reagent molecule. For example, amino acids that constitute a protease recognition site, or other such specifically recognized enzymatic cleavage site, can be used to link the transport reagent to the agent. Alternatively, chemical or other types of linkers that are cleavable by, for example, exposure to light or other stimulus can be used to link the transport reagent to the agent of interest.

A conjugate in which an agent to be delivered and a transport reagent are linked by a specifically cleavable or specifically releasable linker will have a half-life. The term "half-life" in this context refers to the amount of time required after applying the conjugate to an epithelial or endothelial membrane for one half of the amount of conjugate to become dissociated to release the free agent. The half-life for some embodiments is typically between 5 minutes and 24 hours, and more preferably is between 30 minutes and 2 hours. The half-life of a conjugate can be "tuned" or modified, according to the invention, as described below.

In some embodiments, the cleavage rate of the linkers is pH dependent. For example, a linker can form a stable linkage between an agent and a transport reagent at an acidic pH (e.g., pH 6.5 or less, more preferably about 6 or less, and still more preferably about 5.5 or less). However, when the conjugate is placed at physiological pH (e.g., pH 7 or greater, preferably about pH 7.4), the linker will undergo cleavage to release the agent. Such pH sensitivity can be obtained by, for example, including a functional group that, when protonated (i.e., at an acidic pH), does not act as a nucleophile. At a higher (e.g., physiological) pH, the functional group is no longer protonated and thus can act as a nucleophile. Examples of suitable functional groups include, for example, N and S. One can use such functional groups to fine-tune the pH at which self-cleavage occurs.

In another embodiment, the linking moiety is cleaved through self-immolation. Such linking moieties in a transport moiety-biologically active compound conjugate contain a nucleophile (e.g., oxygen, nitrogen and sulfur) distal to the biologically active compound and a cleavable group (e.g., ester, carbonate, carbamate and thiocarbamate) proximal to the biologically active compound. Intramolecular attack of the nucleophile on the cleavable group results in the scission of a covalent bond, thereby releasing the linking moiety from the biologically active compound.

FIG. 5 provides an illustration of several therapeutic agents that are attached via different linking groups to transport moieties of the present invention. In FIG. 5A, mercaptopurine is attached via a disulfide linkage to a N-acetyl cysteine which serves as a linkage to the transport moiety. In FIGS. 5B and 5C, photolabile linkages are illustrated that upon activation from a suitable light source, release mercaptopurine and 5-fluorouracil (5FU), respectively. In FIG. 5D, a linkage that is cleaved in vivo to release a taxane compound (e.g., Taxol) is illustrated.

Examples of conjugates containing self-immolating linking moieties (e.g., biologically active agent-L-transport moiety conjugates) are represented by structures 1, 2 and 3:

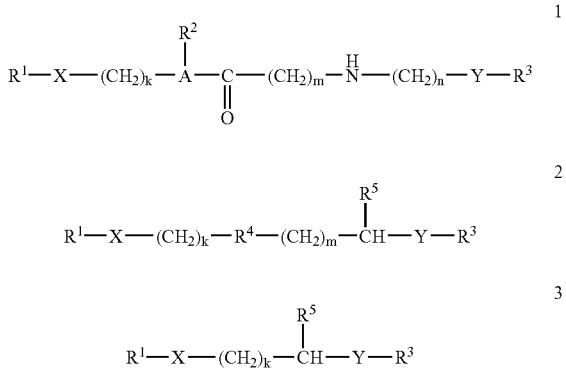

wherein: $R^1$ is the biologically active compound; X is a linkage formed between a functional group on the biologically active compound and a terminal functional group on the linking moiety; Y is a linkage formed from a functional group on the transport moiety and a functional group on the linking moiety; A is N or CH; $R^2$ is hydrogen, alkyl, aryl, arylalkyl, acyl or allyl; $R^3$ is the transport moiety; $R^4$ is S, O, $NR^6$ or $CR^7R^8$; $R^5$ is H, OH, SH or $NHR^6$; $R^6$ is hydrogen, alkyl, aryl, acyl or allyl; $R^7$ and $R^8$ are independently hydrogen or alkyl; k and m are independently either 1 or 2; and n is an integer ranging from 1 to 10. Non-limiting examples of the X and Y linkages are (in either orientation): —C(O)O—, —C(O)NH—, —OC(O)NH—, —S—S—, —C(S)O—, —C(S)NH—, —NHC(O)NH—, —SO$_2$NH—, —SONH—, phosphate, phosphonate and phosphinate. One of skill in the art will appreciate that when the biological agent has a hydroxy functional group, then X will preferably be —OC(O)— or —OC(O)NH—. Similarly, when the linking group is attached to an amino terminus of the transport moiety, Y will preferably be —C(O)NH—, —NHC(O)NH—, —SO$_2$NH—, —SONH— or —OC(O)NH— and the like. In each of the groups provided above, NH is shown for brevity, but each of the linkages (X and Y) can contain substituted (e.g., N-alkyl or N-acyl) linkages as well.

Turning first to linking groups illustrated by structure 1, an example and preferred embodiment is illustrated for formula 1a:

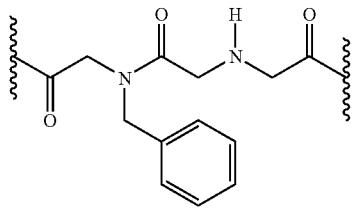

1a wherein the wavy lines indicate points of attachment to the transport moiety and to the biologically active compound. Conjugates containing this linking group can be prepared in a maimer similar to that provided for the transport reagents described in co-pending applications Ser. No. 10/078,247, filed Feb. 14, 2002, published as Pub. No. 2003/0032593A1 on Feb. 13, 2003, and in Ser. No. 09/792,480, filed Feb. 23, 2001 and incorporated herein by reference. One of skill in the art will appreciate that the N-benzyl group can be replaced in formula 1a, with other groups (e.g., alkyl, aryl, allyl and the like) or that methylene groups can be replaced with, for example, ethylene, propylene and the like. Preferably, the methylene groups are retained as shown in 1a, to provide an appropriate steric or spatial orientation that allows the linkage to be cleaved in vivo.

Accordingly, for structure 1, the following substituents are preferred: A is N; $R^2$ is benzyl; k, m and n are 1; X is —OC(O)— and Y is —C(O)NH—.

Linkages of structure 2, are exemplified by formula 2a:

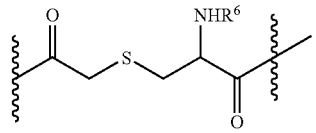

Figure 6:
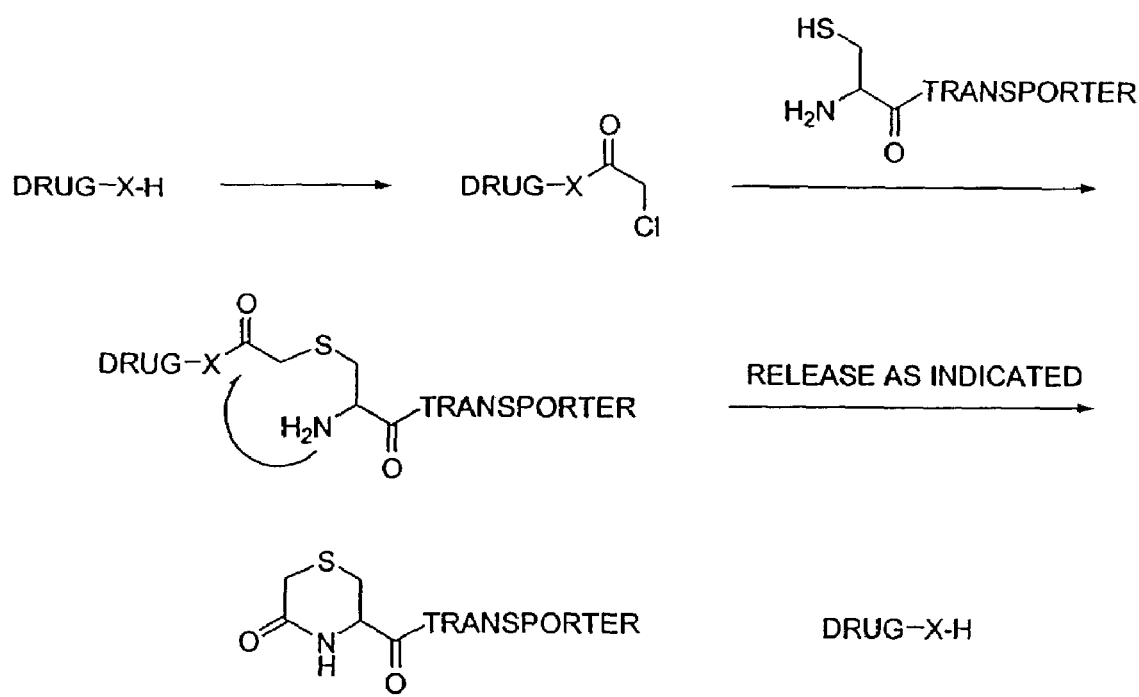
FIG. 6 illustrates a general procedure for the use of a releasable linker in preparing one type of drug-transporter conjugate. Here, a functional group on the therapeutic agent (e.g., —OH or —NH$_2$) is converted to a chloroacetate derivative and treated with a cysteine-modified transporter. Release takes place in vivo due to intramolecular cyclization as indicated.
Figure 7:
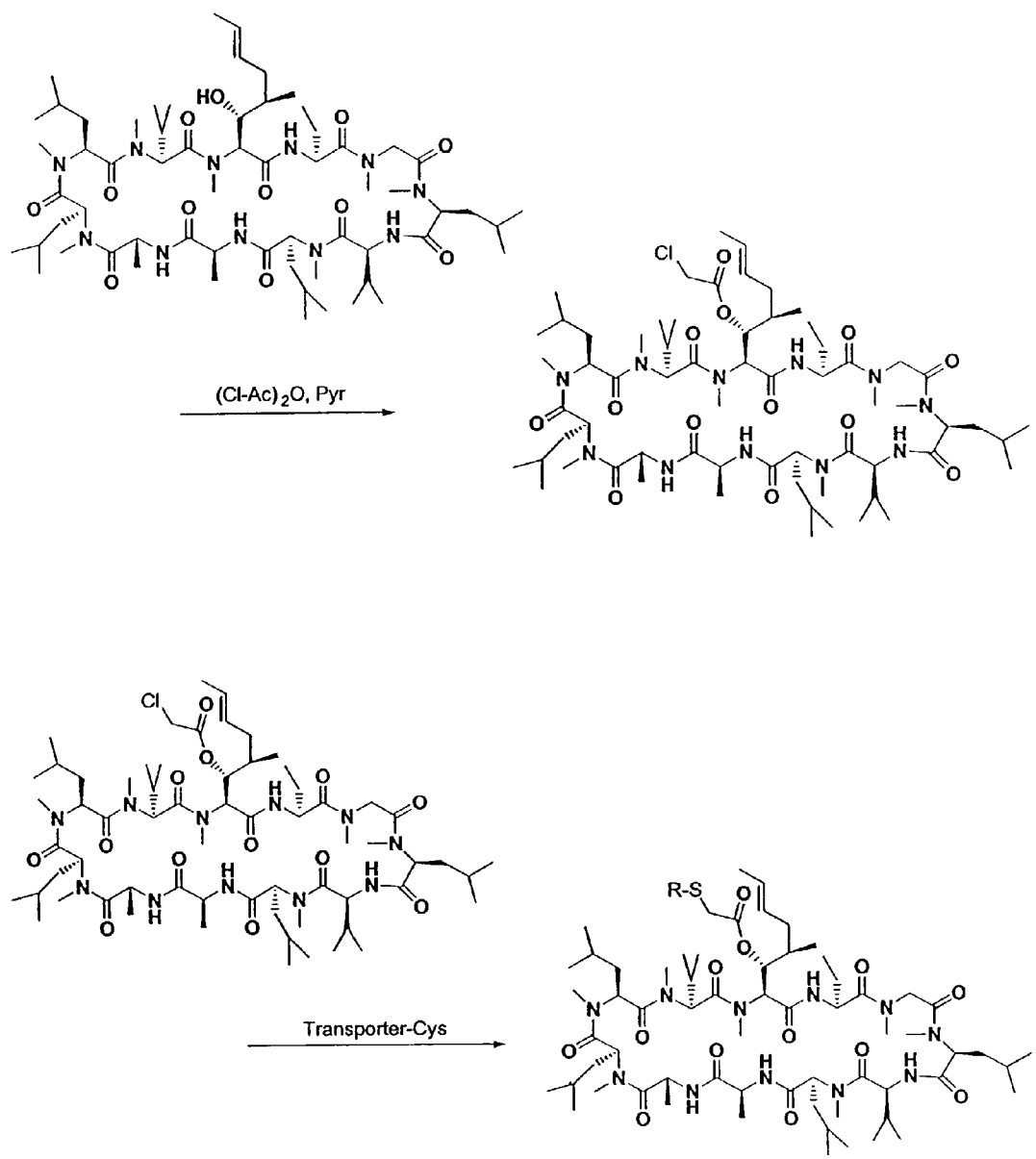
FIG. 7 displays a synthetic scheme for a chemical conjugation between a cyclosporin A and a transport moiety using the methodology outlined in FIG. 6. Here, cyclosporin A is treated with chloroacetic anhydride to produce the corresponding chloroacetate ester, then converted to the transport conjugate with a transport reagent having a cysteine to operate as an additional linking group component.

2a wherein, as above, the wavy lines indicate the point of attachment to each of the transport moiety and the biologically active agent. The preparation of a drug conjugate having a linking group of formula 2a is shown in FIG. 6 (see also FIG. 7, illustrating the attachment of a linkage of this type to cyclosporin A). As seen in FIG. 6, a drug is acylated with α-chloroacetic anhydride to form an α-chloroacetate ester, that is treated with a transport moiety having an attached cysteine residue to provide the target compound in which the linkage has the form:

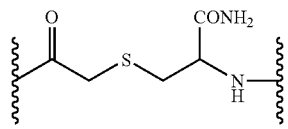

Accordingly, in one group of preferred embodiments, the conjugate is represented by formula 2, in which X is —OC(O)—; Y is —C(O)NH—; $R^4$ is S; $R^5$ is $NHR^6$; and the subscripts k and m are each 1. In another group of preferred embodiments, the conjugate is represented by formula 2, in which X is —OC(O)—; Y is —NHC(O)—; $R^4$ is S; $R^5$ is $CONH_2$; and the subscripts k and m are each 1. Particularly preferred conjugates are those in which $R^6$ is hydrogen, methyl, allyl, butyl or phenyl.

Linking groups represented by the conjugates shown in formula 3 are generally of the heterobifunctional type (e.g, ε-aminocaproic acid, serine, homoserine, γ-aminobutyric acid, and the like), although suitably protected dicarboxylic acids or diamines are also useful with certain biological agents.

For structure 3, the following substituents are preferred: $R^5$ is $NHR^6$, wherein $R^6$ is hydrogen, methyl, allyl, butyl or phenyl; k is 2; X is —C(O)O—; and Y is —C(O)NH—.

Self-immolating linkers typically undergo intramolecular cleavage with a half-life between about 10 minutes and about 24 hours in water at 37° C. at a pH of approximately 7.4. Preferably, the cleavage half-life is between about 20 minutes and about 4 hours in water at 37° C. at a pH of approximately 7.4. More preferably, the cleavage half-life is between about 30 minutes and about 2 hours in water at 37° C. at a pH of approximately 7.4.

Returning now to conjugates represented by structure 1, one of skill in the art will appreciate that the cleavage half-life, that is the separation of biological agent from the transporter, can be adjusted by varying the $R^2$ substituent. By using an $R^2$ of increased or decreased size, one can obtain a conjugate having a longer or shorter half-life respectively. $R^2$ in structure 1 is preferably methyl, ethyl, propyl, butyl, allyl, benzyl or phenyl.

Where there is a basic or acidic group in a self-immolating linker, one can oftentimes adjust cleavage half-life according to the pH of the conjugate solution. For instance, the backbone amine group of structure 1 is protonated at acidic pH (e.g., pH 5.5). The amine cannot serve as a nucleophile inducing intramolecular cleavage when it is protonated. Upon introduction of the conjugate into a medium at physiological pH (7.4), however, the amine is unprotonated a significant portion of the time. The cleavage half-life is correspondingly reduced.

In one embodiment, cleavage of a self-immolating linker occurs in two steps: intramolecular reaction of a nucleophilic group resulting in the cleavage of a portion of the linking moiety; and, elimination of the remaining portion of the linking moiety. The first step of the cleavage is rate-limiting and can be fine-tuned for pH sensitivity and half-life.

Structure 4 is an example of a two-step, self-immolating moiety that is incorporated into a transport moiety-biologically active compound conjugate:

4 wherein: $R^1$ is the biologically active compound; X represents a linkage between a functional group on the biologically active compound and a functional group on the linking moiety; Ar is a substituted or unsubstituted aryl group, wherein the methylene substituent and phenolic oxygen atom are either ortho or para to one another; $R^3$ is the transport moiety; $R^4$ is S, O, $NR^6$ or $CR^7R^8$; $R^5$ is H, OH, SH or $NHR^6$; $R^6$ is hydrogen, alkyl, aryl, arylalkyl, acyl or allyl; $R^7$ and $R^8$ are independently hydrogen or alkyl; and, k and m are independently either 1 or 2.

A particularly preferred linking group has the formula 4a:

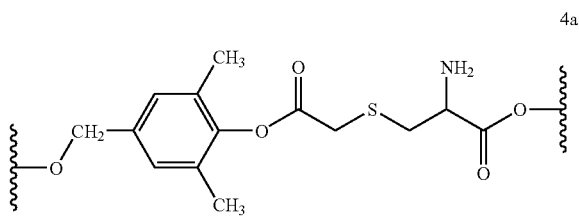

Accordingly, the linking groups used in the conjugates of formula 4, are preferably those in which Ar is an substituted or unsubstituted phenylene group; $R^4$ is S; R is $NHR^6$, wherein $R^6$ is hydrogen, methyl, allyl, butyl, acetyl or phenyl; k and m are 1; X is —C(O)O—; and Y is —C(O)O— or —C(O)NH—. More preferably, $R^6$ is hydrogen or acetyl.

Still other useful linking groups for use in the present invention have been described in copending PCT applications. See, for example PCT applications US98/10571 (Publication No. WO 98/52614) and US00/23440 (Publication No. WO 01/13957) which describe linking groups for similar compositions, e.g., conjugates of biologically active agents and transport oligomers. The linking technology described therein can be used in the present compositions in a similar manner.

III. Synthesis of Transport Reagents and Conjugates

The reagents described herein are constructed by any method known in the art. Exemplary polyamides can be produced synthetically, preferably using a peptide synthesizer adapted for the use of suitable subunits (Applied Biosystems Model 433).

N-methyl and hydroxy-amino acids can be substituted for conventional amino acids in solid phase peptide synthesis. However, production of reagents with reduced peptide bonds requires synthesis of the dimer of amino acids containing the reduced peptide bond. Such dimers are incorporated into polymers using standard solid phase synthesis procedures. Other synthesis procedures are well known and can be found, for example, in Fletcher et al. (1998), Simon et al. (1992), and references cited therein.

A. Carbamate Transport Reagents

Carbamate transport reagents can be prepared as illustrated in Schemes 1 and 2 (see FIG. 11).

With reference to Scheme 1, the monomeric units used in construction of some versions of the carbamate transport reagents can be prepared from suitably protected forms of ornithine. Accordingly, treatment of $N^\alpha$-Fmoc $N^\delta$-Boc L-ornithine (i) with isobutyryl chloroformate followed by sodium borohydride provides the alcohol (ii) which can be converted to the protected monomer (iii) upon treatment with 4-nitrophenyl chloroformate and pyridine. One of skill in the art will appreciate that substitution of the protected ornithine (i) with related acids (e.g., protected forms of D- or L-lysine) can provide other protected monomer intermediates having longer or shorter side chain linkages.

As shown in Scheme 2, treatment of an amine resin (iv) with monomer (iii) in the presence of HOBt, DIEA and DMF, followed by piperidine in DMF provides a support bound monomer of formula (v, subscript n is 1). Repeating the steps of monomer addition and Fmoc-removal provides a support bound oligomer of formula v (subscript n is 4–12). Once an oligomer of appropriate length has been constructed, a linking group to a suitable therapeutic or diagnostic agent can be attached. Thus, treatment of v with Fmoc-amino caproic acid in the presence of DIC, HOBt and DMF, followed by piperidine and DMF provides the amino caproic acid conjugate that can be combined with FITC in the presence of DIEA and DMF to provide the linked FITC conjugate. The Boc protecting groups can then be removed, the intermediate can be removed from the resin, and the primary amino groups can be perguanylated with, for example, Im-C(=NH)$NH_2$ in the presence of sodium carbonate to provide a target compound.

Scheme 2 shows the preparation of a tranport polymer having subunits attached via carbamate linkages. One of skill in the art will understand that the synthesis can include amino acid monomers (e.g., glycine, α-aminocaproic acid, γ-aminobutyric acid, and the like) to provide suitable spacing between the guanidino-containing monomeric units.

B. γ-Peptide Transport Reagents

In another group of embodiments, the transport reagent can be constructed from γ-amino acid monomers (prepared as illustrated in Scheme 3, see FIG. 12).

As shown in Scheme 3, a suitably protected ornithine vii can be converted to its two carbon homolog in a multistep process. Treatment of vii with Meldrum's acid in the presence of DCC, DMAP and dichloromethane provides viii. Reduction of the ketone carbonyl can be accomplished using acetic acid, sodium borohydride in dichloromethane to provide ix. Heating ix in toluene at reflux produces x, which can by hydrolyzed (NaOH in acetone) to provide xi. Removal of the Boc protecting group and reprotection of the resultant amine functional group with Fmoc-OSu in DMF provides the monomer xii.

Scheme 4 (see FIG. 12) illustrates the use of monomer xii in the preparation of a transport conjugate. As shown above, an amino resin (iv) is treated with xii in the presence of DIEA, HOBt, HBTU and NMP, and deprotected (piperidine) to provide xiii (wherein the subscript n is 1). Additional monomeric groups can be added either sequentially as shown in Scheme 4, or interrupted by non-guanidino containing subunits. For simplicity, Scheme 4 illustrates the preparation of an oligomer in which all the subunits have a side chain that will be converted to a guanidino group. Thus, xiii (n=1) can be subjected to n steps of monomeric coupling and deprotection to provide, for example xiii wherein n=5. Subsequent steps to couple amino caproic acid (aca) and FITC proceed as outlined in Scheme 2 to provide xiv. Removal of the Z groups (benzyloxycarbonyl groups) and cleavage of the transport conjugate intermediate from the resin provides xv. Conversion of the primary amine functional groups to guanidino groups can be accomplished with guanyl pyrazole in the presence of sodium carbonate to provide xvi.

C. Glutaramide and Oxalamide Transport Reagents

Figure 13:
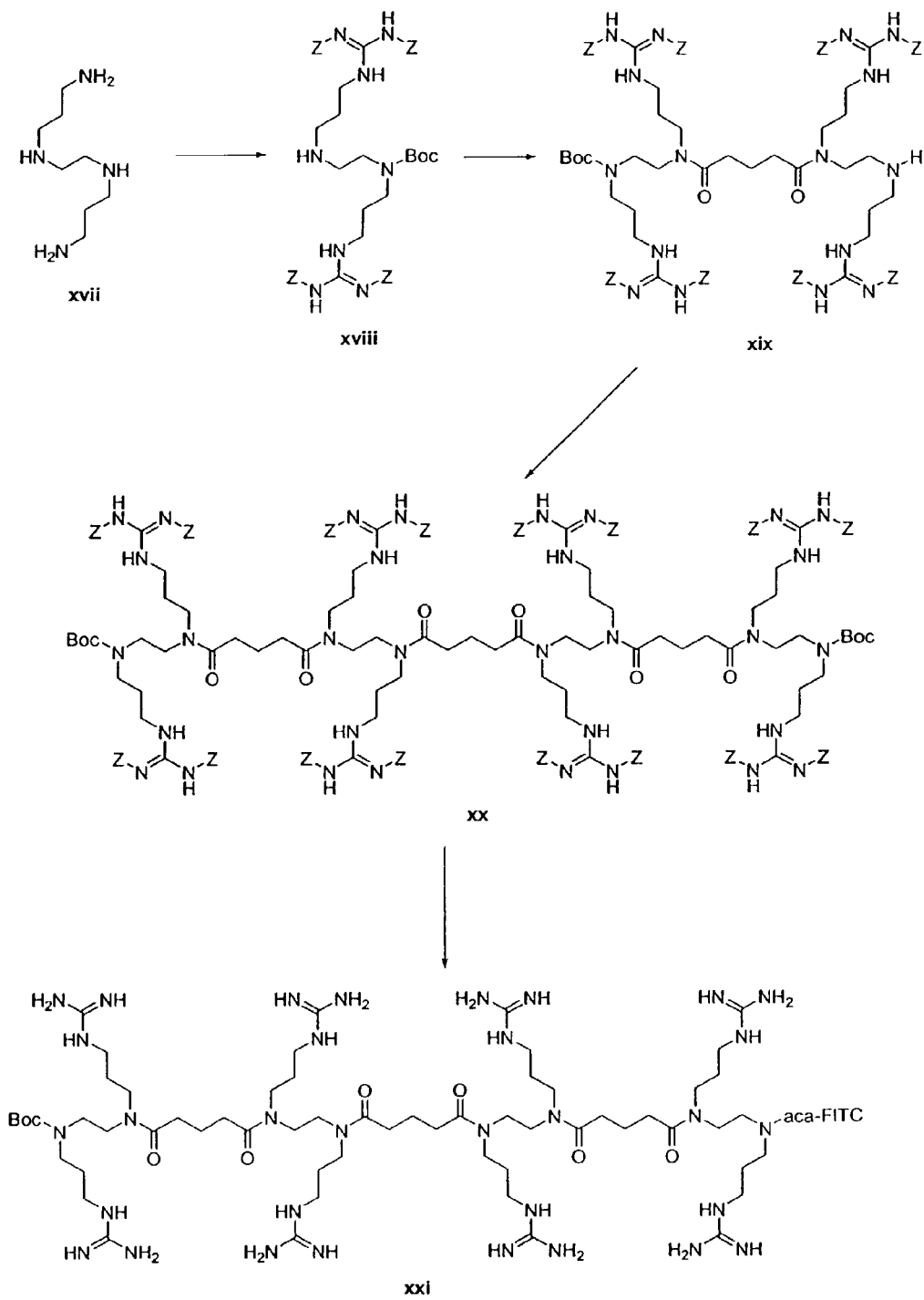
FIG. 13 provides Scheme 5 illustrating the preparation of transport reagents having a glutaramide backbone. Synthesis can be accomplished in solution with aminocaproic acid (aca) as a linking group to the biological agent (FITC).

In another group of embodiments, the transport reagent is a glutaramide derivative, the preparation of which is illustrated in Scheme 5 (see FIG. 13).

In Scheme 5, N,N'-bis(3-aminopropyl)ethylenediamine (xvii) is guanidinylated on the terminal primary amino groups, and mono-protected to provide xviii. A dimeric structure is then formed by combining two equivalents of xviii with a suitably activated glutaric acid, and mono-deprotected to form xix. Again, two equivalents of xix are combined with an activated glutaric acid reagent to form xx. Removal of one Boc protecting group and coupling to aca-FITC as described for transport reagents above, and further removal of the carbobenzyloxy protecting groups (Z), provides the compound xxi.

Figure 14:
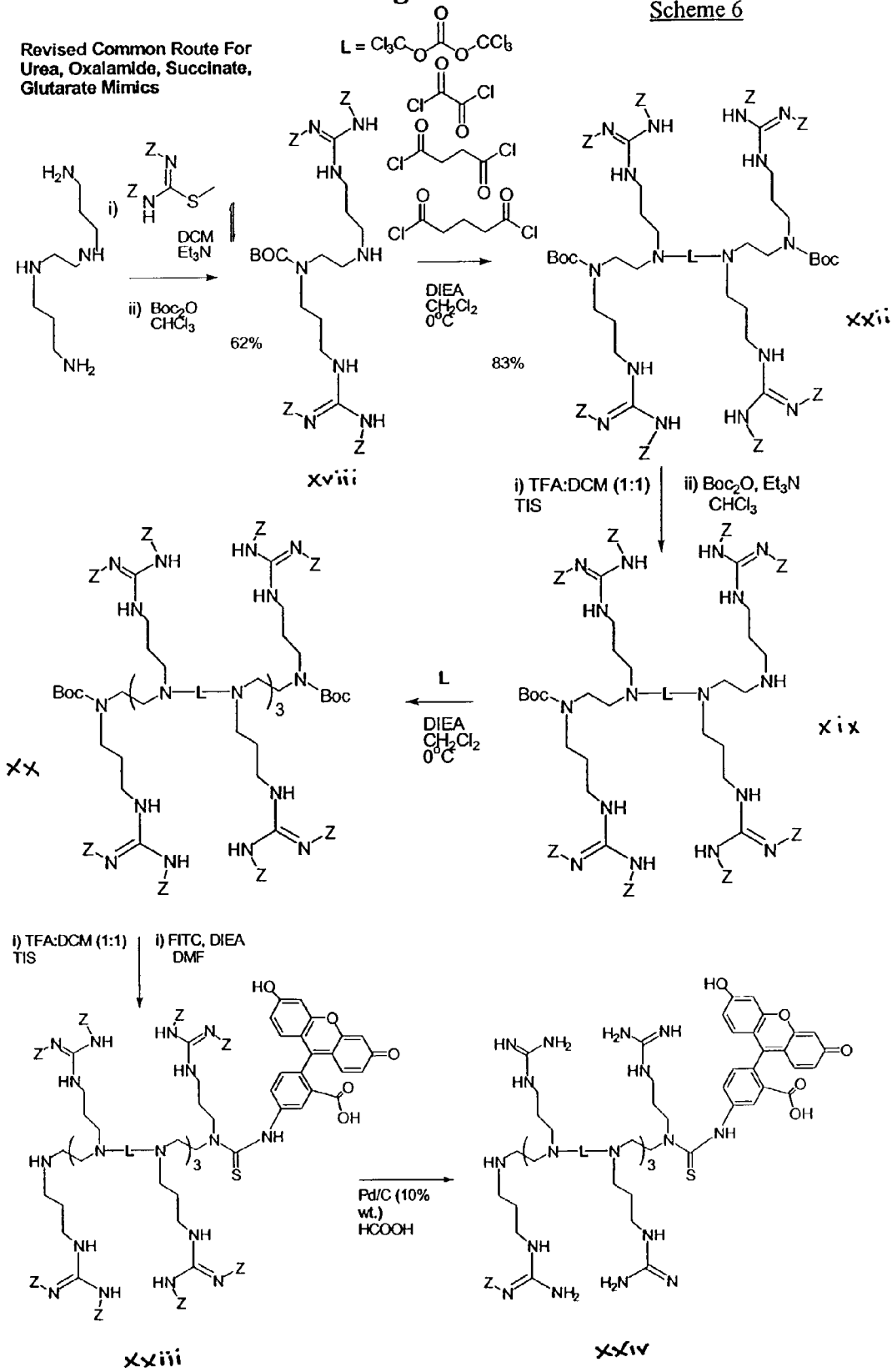
FIG. 14 provides Scheme 6 illustrating the preparation of transport reagents having backbones related to the glutaramide backbone illustrated in FIG. 13. These backbone derivatives are referred to as "urea," "oxalamide" and "succinamide". Synthesis can be accomplished in solution and is illustrated with attachment of FITC through a thiourea linkage.

Scheme 6 (see FIG. 14) illustrates the extention of the methodology above, to "oxalamide" transport reagents (L=—C(O)C(O)—), "urea" transport reagents (L=—C (O)—) and the like.

D. Polyamine Transport Reagents

Figure 15:
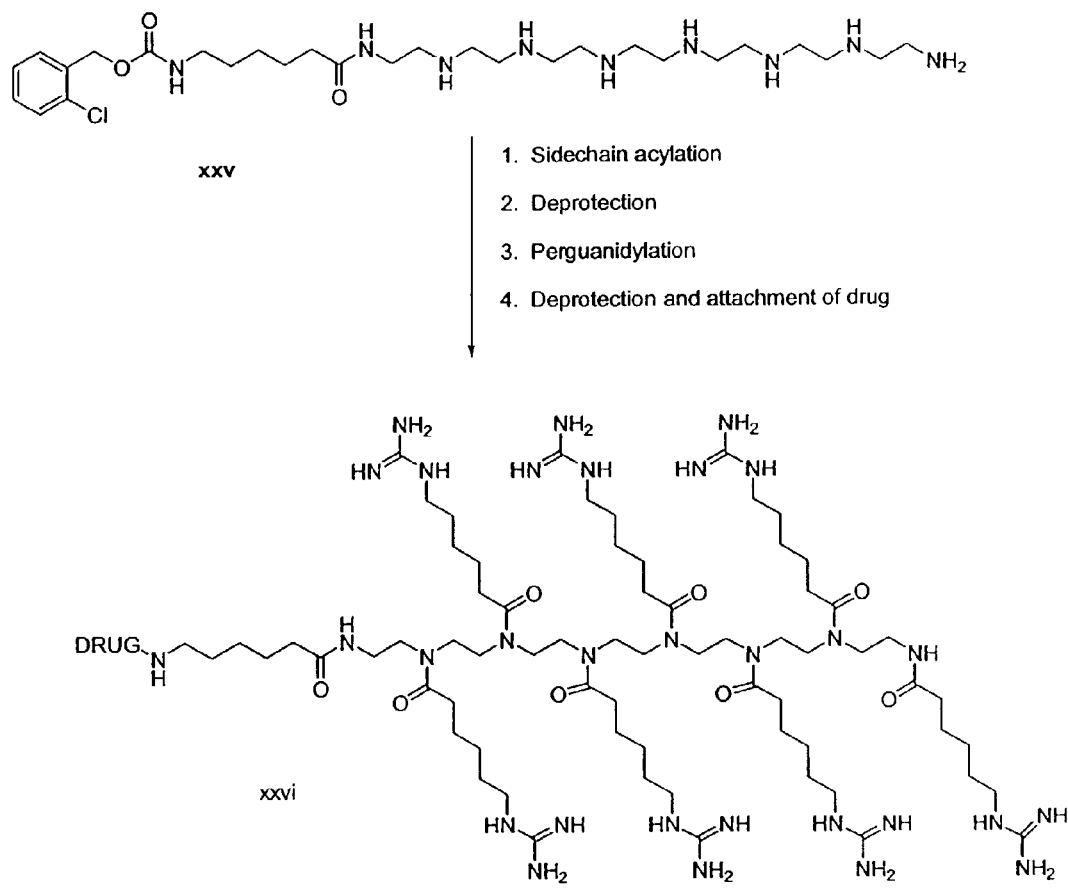
FIG. 15 provides Scheme 7 illustrating the preparation of transport reagents having a polyamine backbone. Synthesis can be accomplished in solution with aminocaproic acid as a linking group to the biological agent (drug).
Figure 16C:
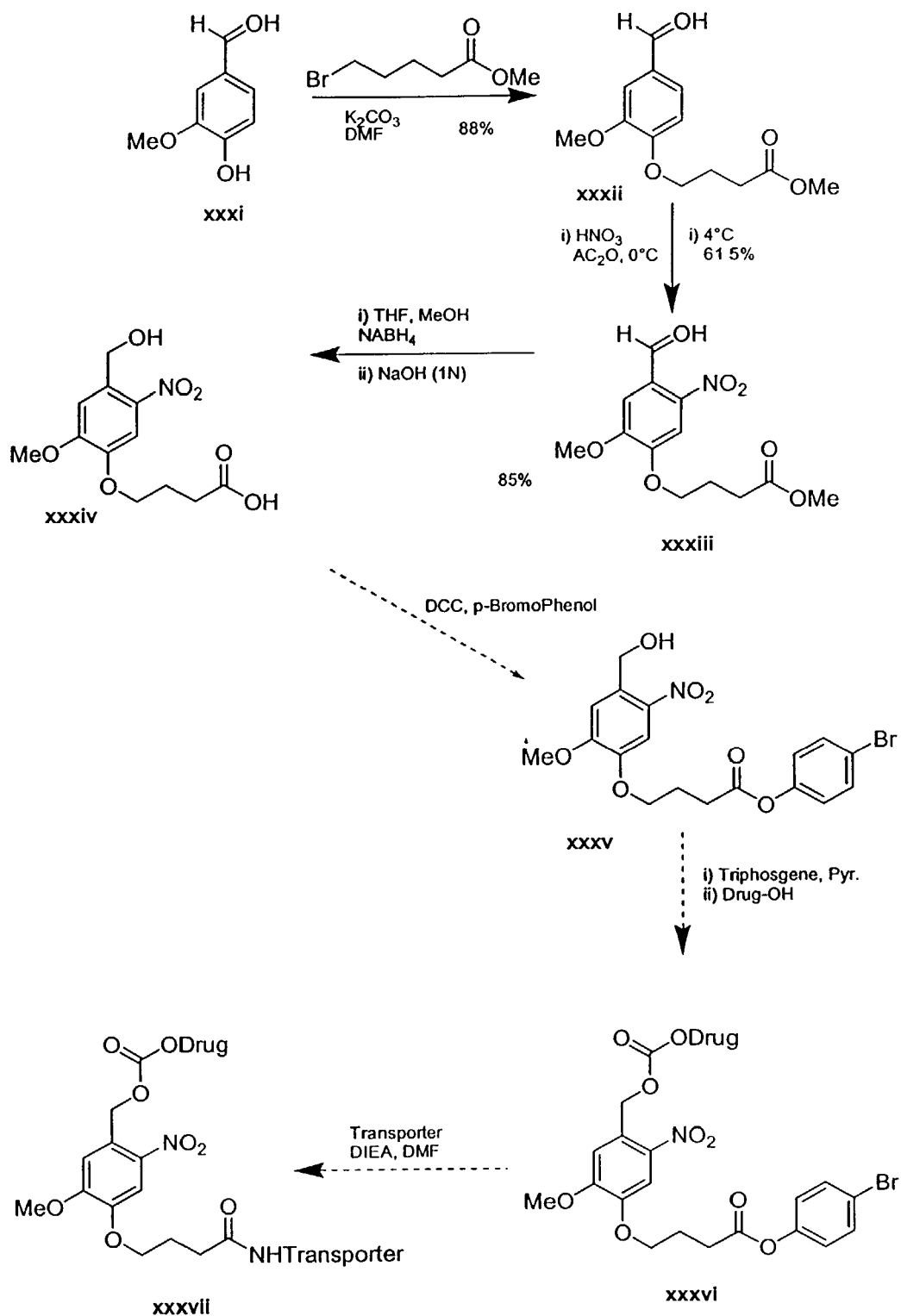
Figure 16D:
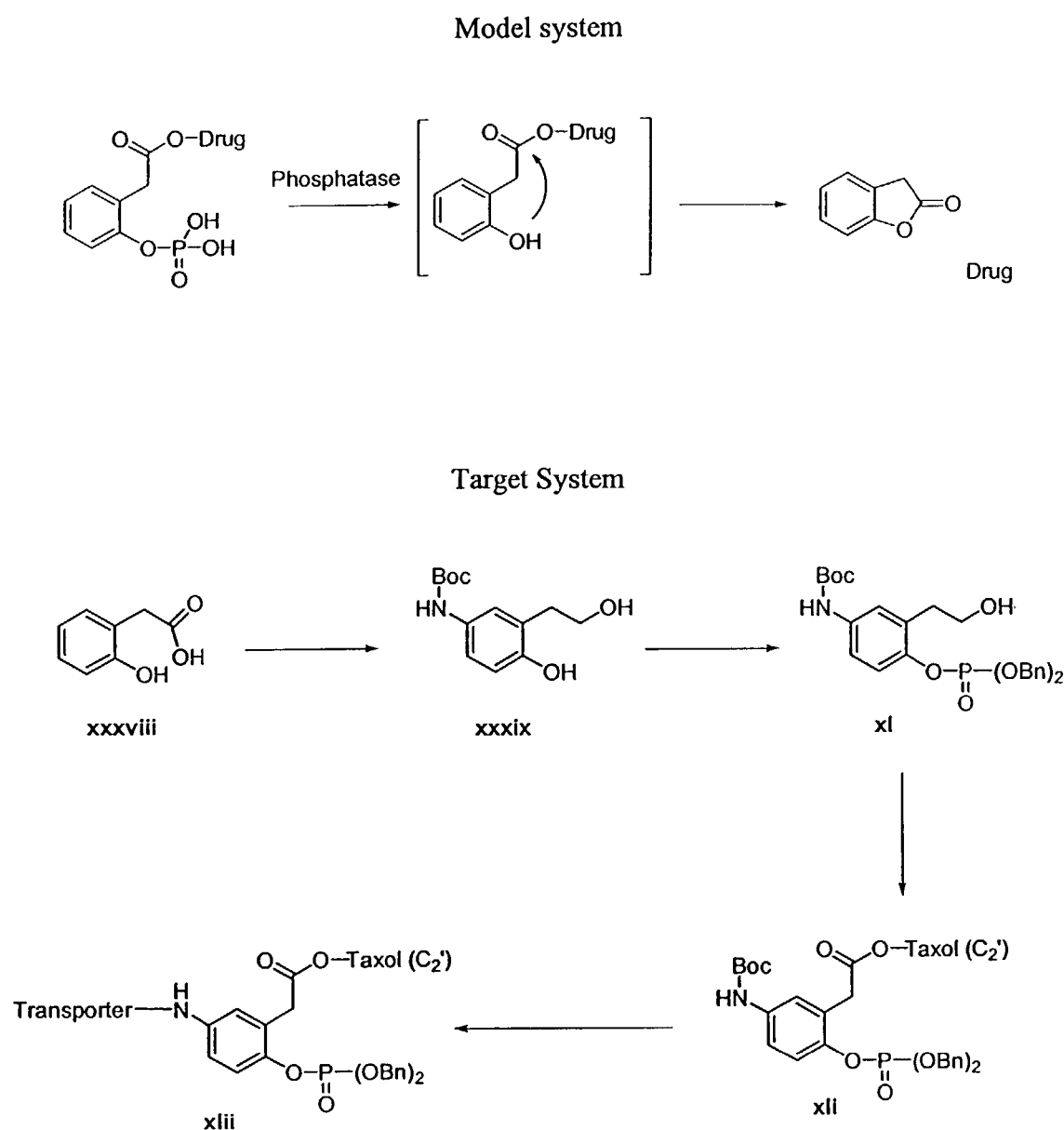

In yet another group of embodiments, the transport reagent is a polyamine transport reagent. In this group of embodiments, the backbone is either a polyamine or contains polyamine features (e.g., polyethyleneamine, polypropyleneamine and the like). Scheme 7 (see FIG. 15) illustrates one type of polyamine transport reagent.

In Scheme 7, a polyethyleneimine is mono-acylated with a protected form of ∊-aminocaproic acid to provide the starting material shown. The remaining amino groups can be peracylated with, for example, protected ∊-aminocaproic acid chloride to provide a suitable backbone with sidechain linking groups. Removal of the sidechain protection groups and perguanidylation provides a transport reagent having an attached protected linking group suitable for conjugation to a biologically active agent.

IV. Enhanced Transport of Biologically Active Agents Across Biological Membranes A. Measuring Transport Across Biological Membranes Model systems for assessing the ability of transport reagents of the invention to transport biologically active agents and other therapeutic substances across biological membranes include systems that measure the ability of the transport reagent to transport a covalently attached fluorescent molecule across the membrane. For example, fluorescein (≈376 MW) can serve as a model for transport of small organic molecules. For transport of macromolecules, a transport reagent can be fused to a large polypeptide such as ovalbumin (molecular weight 45 kDa). Detecting uptake of macromolecules may be facilitated by attaching a fluorescent tag. Cellular uptake can also be analyzed by confocal microscopy.

B. Enhanced Transport Across Biological Membranes

In experiments carried out in support of the present invention, transmembrane transport and concomitant cellular uptake was assessed by uptake of a transport reagent linked to fluorescein, according to known methods (see co-pending application Ser. No. 09/792,480 filed Feb. 23, 2001). Briefly, suspensions of cells were incubated with fluorescent conjugates suspended in buffer for varying times at 37° C., 23° C., or 3° C. After incubation, the reaction was stopped and the cells were collected by centrifugation and analyzed for fluorescence using fluorescence-activated cell sorting (FACS).

Under the conditions used, cellular uptake of the conjugates was not saturable. Consequently, $ED_{50}$ values could not be calculated for the transport reagents. Instead, data are presented as histograms to allow direct comparisons of cellular uptake at single conjugate concentrations.

Comparisons of carbamate transport reagents and oligoArg transport reagents indicate that the carbamate transport reagents are comparable to, or better than the peptide transport reagents having similar characteristics (e.g., overall length, number and type of guanidinium head groups, etc.).

The overall transport efficacy of a transport reagent appears to depend on a combination of (i) rate of transmembrane uptake (polymers with less than about 15 continuous guanidino containing groups are better) versus susceptibility to proteolytic inactivation (longer polymers are better). Accordingly, polymers containing 7 to 20 guanidinium residues, and preferably 7 to 15, are preferred.

According to a preferred embodiment of the invention, the transport reagent of the invention has an apparent affinity (Km) that is at least 10-fold greater, and preferably at least 100-fold greater, than the affinity measured for tat by the methods described herein when measured at room temperature (23° C.) or 37° C.

Without ascribing to any particular theory, the data suggest that the transport process is an energy-dependent process mediated by specific recognition of guanidinium or amidinium-containing polymers by a molecular transport reagent present in cellular plasma membranes.

Other experiments in support of the invention have shown that the conjugates of the invention are effective to transport biologically active agents across membranes of a variety of cell types, including human T cells (Jurkat), B cells (murine CH27), lymphoma T cells (murine EL-4), mastocytoma cells (murine P388), several murine T cell hybridomas, neuronal cells (PC-12), fibroblasts (murine RT), kidney cells (murine HELA), myeloblastoma (murine K562); and primary tissue cells, including all human blood cells (except red blood cells), such as T and B lymphocytes, macrophages, dendritic cells, and eosinophils, basophiles, mast cells, endothelial cells, cardiac tissue cells, liver cells, spleen cells, lymph node cells, and keratinocytes.

The conjugates are also effective to traverse both gram negative and gram positive bacterial cells. More generally, maximum uptake levels by the bacteria can be observed at 37° C. However, significant staining can be observed when incubation is performed either at room temperature or at 3° C. Confocal microscopy revealed that pretreatment of the bacteria with 0.5% sodium azide inhibited transport across the inner plasma membranes of both gram-positive and gram-negative bacteria, but not transport across the cell wall (gram-positive bacteria) into the periplasmic space.

Thus, the invention includes conjugates that contain antimicrobial agents, such as antibacterial and antifungal compounds, for use in preventing or inhibiting microbial proliferation or infection, and for disinfecting surfaces to improve medical safety. In addition, the invention can be used for transport into plant cells, particularly in green leafy plants.

Additional studies in support of the invention have shown that translocation across bacterial membranes is both energy- and temperature-dependent, consistent with observations noted earlier for other cell-types.

V. Screening Assay Methods and Libraries

In another embodiment, the invention can be used to screen one or more conjugates for a selected biological activity, wherein the conjugate(s) are formed from one or more candidate agents. Conjugate(s) are contacted with a cell that exhibits a detectable signal upon uptake of the conjugate into the cell, such that the magnitude of the signal is indicative of the efficacy of the conjugate with respect to the selected biological activity.

One advantage of this embodiment is that it is particularly useful for testing the activities of agents that by themselves are unable, or poorly able, to enter cells to manifest biological activity. Thus, the invention provides a particularly efficient way of identifying active agents that might not otherwise be accessible through large-scale screening programs, for lack of an effective and convenient way of transporting the agents into the cell or organelle.

Preferably, the one or more candidate agents are provided as a combinatorial library of conjugates which are prepared using any of a number of combinatorial synthetic methods known in the art. For example, Thompson and Ellman (1996) recognized at least five different general approaches for preparing combinatorial libraries on solid supports, namely (1) synthesis of discrete compounds, (2) split synthesis (split and pool), (3) soluble library deconvolution, (4) structural determination by analytical methods, and (5) encoding strategies in which the chemical compositions of active candidates are determined by unique labels, after testing positive for biological activity in the assay. Synthesis of libraries in solution includes at least (1) spatially separate syntheses and (2) synthesis of pools (Thompson, supra). Further description of combinatorial synthetic methods can be found in Lam et al. (1997), which particularly describes the one-bead-one-compound approach.

These approaches are readily adapted to prepare conjugates in accordance with the present invention, including suitable protection schemes as necessary. For example, for a library that is constructed on one or more solid supports, a transport peptide moiety can be attached to the support(s) first, followed by building or appending candidate agents combinatorially onto the polymers via suitable reactive functionalities. In an alternative example, a combinatorial library of agents is first formed on one or more solid supports, followed by appending a transport reagent to each immobilized candidate agent. Similar or different approaches can be used for solution phase syntheses. Libraries formed on a solid support are preferably severed from the support via a cleavable linking group by known methods (Thompson et al., and Lam et al., supra).

The one or more conjugate candidates can be tested with any of a number of cell-based assays that elicit detectable signals in proportion to the efficacy of the conjugate. Conveniently, the candidates are incubated with cells in multi-well plates, and the biological effects are measured via a signal (e.g., fluorescence, reflectance, absorpion, or chemiluminescence) that can be quantitated using a plate reader. Alternatively, the incubation mixtures can be removed from the wells for further processing and/or analysis. The structures of active and optionally inactive compounds, if not already known, are then determined, and this information can be used to identify lead compounds and to focus further synthesis and screening efforts.

For example, a γ-interferon secretion assay can be readily adapted to a multiwell format, such that active secretion inhibitors can be detected by europium-based fluorescence detection using a plate reader. Anticancer agents can be screened using established cancer cell lines (e.g., provided by the National Institutes of Health (NIH) and the National Cancer Institute (NCI). Cytotoxic effects of anticancer agents can be determined by trypan dye exclusion, for example.

Other examples include assays directed to inhibiting cell signaling, such as IL-4 receptor inhibition; assays for blocking cellular proliferation, and gene expression assays. In a typical gene expression assay, a gene of interest is placed under the control of a suitable promotor and is followed downstream by a gene for producing a reporter species such as β-galactosidase or firefly luciferase. An inhibitory effect can be detected based on a decrease in reporter signal.

The invention also includes a conjugate library which is useful for screening in the above method. The library includes a plurality of candidate agents for one or more selected biological activities, each of which is conjugated to at least one transport reagent in accordance with the invention. Preferably, the conjugate library is a combinatorial library. In another embodiment, the invention includes a regular array of distinct polymer-agent conjugates distributed in an indexed or indexable plurality of sample wells, for testing and identifying active agents of interest.

VI. Pharmaceutical Compositions

Compounds and methods of the present invention have particular utility in the area of human and veterinary therapeutics. Generally, administered dosages will be effective to deliver picomolar to micromolar concentrations of the therapeutic composition to the effector site. Appropriate dosages and concentrations will depend on factors such as the therapeutic composition or drug, the site of intended delivery, and the route of administration, all of which can be derived empirically according to methods well known in the art. Further guidance can be obtained from studies using experimental animal models for evaluating dosage, as are known in the art.

Administration of the compounds of the invention with a suitable pharmaceutical excipient as necessary can be carried out via any of the accepted modes of administration. Thus, administration can be, for example, intravenous, topical, subcutaneous, transcutaneous, intramuscular, oral, intrajoint, perenteral, peritoneal, intranasal, or by inhalation. The formulations may take the form of solid, semi-solid, lyophilized powder, or liquid dosage forms, such as, for example, tablets, pills, capsules, powders, solutions, suspensions, emulsions, suppositories, retention enemas, creams, ointments, lotions, aerosols or the like, preferably in unit dosage forms suitable for simple administration of precise dosages.

The compositions typically include a conventional pharmaceutical carrier or excipient and may additionally include other medicinal agents, carriers, adjuvants, and the like. Preferably, the composition will be about 5% to 75% by weight of a compound or compounds of the invention, with the remainder consisting of suitable pharmaceutical excipients. Appropriate excipients can be tailored to the particular composition and route of administration by methods well known in the art, e.g., (Gennaro, 1990).

For oral administration, such excipients include pharmaceutical grades of mannitol, lactose, starch, magnesium stearate, sodium saccharine, talcum, cellulose, glucose, gelatin, sucrose, magnesium carbonate, and the like. The composition may take the form of a solution, suspension, tablet, pill, capsule, powder, sustained-release formulation, and the like.

In some embodiments, the pharmaceutical compositions take the form of a pill, tablet or capsule, and thus, the composition can contain, along with the biologically active conjugate, any of the following: a diluent such as lactose, sucrose, dicalcium phosphate, and the like; a disintegrant such as starch or derivatives thereof; a lubricant such as magnesium stearate and the like; and a binder such a starch, gum acacia, polyvinylpyrrolidone, gelatin, cellulose and derivatives thereof.

The active compounds of the formulas may be formulated into a suppository comprising, for example, about 0.5% to about 50% of a compound of the invention, disposed in a polyethylene glycol (PEG) carrier (e.g., PEG 1000 [96%] and PEG 4000 [4%]).

Liquid compositions can be prepared by dissolving or dispersing compound (about 0.5% to about 20%), and optional pharmaceutical adjuvants in a carrier, such as, for example, aqueous saline (e.g., 0.9% w/v sodium chloride), aqueous dextrose, glycerol, ethanol and the like, to form a solution or suspension, e.g., for intravenous administration. The active compounds may also be formulated into a retention enema.

If desired, the composition to be administered may also contain minor amounts of non-toxic auxiliary substances such as wetting or emulsifying agents, pH buffering agents, such as, for example, sodium acetate, sorbitan monolaurate, or triethanolamine oleate.

For topical administration, the composition is administered in any suitable format, such as a lotion or a transdermal patch. For delivery by inhalation, the composition can be delivered as a dry powder (e.g., Inhale Therapeutics) or in liquid form via a nebulizer.

Methods for preparing such dosage forms are known or will be apparent to those skilled in the art; for example, see *Remington's Pharmaceutical Sciences* (1980). The composition to be administered will, in any event, contain a quantity of the pro-drug and/or active compound(s) in a pharmaceutically effective amount for relief of the condition being treated when administered in accordance with the teachings of this invention.

Generally, the compounds of the invention are administered in a therapeutically effective amount, i.e., a dosage sufficient to effect treatment, which will vary depending on the individual and condition being treated. Typically, a therapeutically effective daily dose is from 0.1 to 100 mg/kg of body weight per day of drug. Most conditions respond to administration of a total dosage of between about 1 and about 30 mg/kg of body weight per day, or between about 70 mg and 2100 mg per day for a 70 kg person.

Stability of the conjugate can be further controlled by the composition and stereochemistry of the backbone and sidechains of the polymer. For polypeptide polymers, D-isomers are generally resistant to endogenous proteases, and therefore have longer half-lives in serum and within cells. D-polypeptide polymers are therefore appropriate when longer duration of action is desired. L-polypeptide polymers have shorter half-lives due to their susceptibility to proteases, and are therefore chosen to impart shorter acting effects. This allows side-effects to be averted more readily by withdrawing therapy as soon as side-effects are observed. Polypeptides comprising mixtures of D and L-residues have intermediate stabilities. Homo-D-polymers are generally preferred.

The following examples are intended to illustrate but not limit the present invention.

EXAMPLES

In the examples below, uptake into cells and across tissues is demonstrated for conjugates wherein the biologically active agent is attached to oligomers of arginine (D- or L-arginine) as well as transport reagents having backbones such as the carbamates and γ-amino acids. The peptide transport reagents served as a suitable model for construction of the present conjugates and for evaluation of uptake and release of the biologically active agents.

Accordingly, efficacy of conjugates having peptide transport reagents is indicative of the efficacy for related non-peptide transport reagent conjugates.

Example 1

This example illustrates the preparation of several releaseable linkages based on an amino acid, that can be modified to attach (and release) a drug having suitable functional groups. Scheme 8 (FIGS. 16a, 16b, 16c and 16d) provides target systems and models for linkages including amide linkages (Scheme 8A), carbonate linkages (Scheme 8B), carbamate linkages (Scheme 8C), photolabile linkages (Scheme 8D), and phosphatase released linkages (Scheme 8E).

Preparation of Model Systems

Ac-Tyr(OAc)—OH (xxviii). To a vigorously stirred suspension of (−) tyrosine xxvii (700 mg, 3.87 mmol) in $H_2O$ (6 mL) at 0° C. was added NaOH (aq) (1.0 N, 3.87 mL, 3.87 mmol). Acetic anhydride (0.802 mL, 868 mg, 8.51 mmol) was added dropwise. During this addition, 1 N NaOH (aq) was added as to maintain the reaction pH between 6 and 8. After the addition was complete, the reaction was warmed to rt and stirred for 35 min. The colorless solution was then carefully acidified to pH 2 with 6 N HCl (aq). Upon standing at rt for 2 min, a white precipitate formed. This solid was filtered and washed with $H_2O$ (3×) to afford the desired product xxviii (581 mg, 2.19 mmol, 57%).

Ac-Tyr($O_2$COBn)—OH (xxix). To a solution of (−) tyrosine xxvii (2.50 g, 13.8 mmol) in NaOH (aq) (2 N, 7.59 mL, 15.2 mmol) was added $H_2O$ (6 mL). This vigorously stirred solution was cooled to 0° C., and acetic anhydride (3.25 mL, 3.52 g, 34.5 mmol) was added via syringe pump over 30 min. During this addition, excess NaOH (aq) (2 N, 34.5 mL, 69.0 mmol) was added in 10 portions. After the addition was complete, the reaction was warmed to room temperature and stirred for 45 min. The colorless solution was then carefully acidified to pH 2 with 6 N HCl (aq). After concentrating under reduced pressure, the resulting solid was extracted with 15% $H_2O$ in acetone (4×). The filtrate was concentrated under reduced pressure to afford a slightly yellow oil. The addition of $H_2O$ (1.5 mL) afforded N-acetyl tyrosine as a white precipitate (670 mg, 3.00 mmol, 22%) that was washed with $H_2O$ (3×). The washings were saved for later precipitations. To a solution of N-acetyl tyrosine (72 mg, 0.32 mmol) in 1:1 THF:$H_2O$ (1 mL) was added NaOH (aq) (1 N, 0.32 mL, 0.32 mmol). Benzyl chloroformate (49 μL, 58 mg, 0.34 mmol) was added followed by the dropwise addition of $K_2CO_3$ (aq) (2 N, 0.16 mL, 0.32 mmol). After stirring for 7 h at rt, the reaction was poured over $H_2O$ (10 mL) and carefully acidified to pH 2 with 6 N HCl (aq). The product was extracted from the water layer with EtOAc (3×), and the combined organic phase was separated, dried over $MgSO_4$, filtered and concentrated under reduced pressure to afford the desired product xxix as a white solid (81 mg, 0.24 mmol, 75%).

Ac-Tyr($O_2$CNHCy)—OH (xxx). To a solution of (−) tyrosine (2.50 g, 13.8 mmol) in NaOH (aq) (2 N, 7.59 mL, 15.2 mmol) was added $H_2O$ (6 mL). This vigorously stirred solution was cooled to 0° C., and acetic anhydride (3.25 mL, 3.52 g, 34.5 mmol) was added via syringe pump over 30 min. During this addition, excess NaOH (aq) (2 N, 34.5 mL, 69.0 mmol) was added in 10 portions. After the addition was complete, the reaction was warmed to room temperature and stirred for 45 min. The colorless solution was then carefully acidified to pH 2 with 6 N HCl (aq). After concentrating under reduced pressure, the resulting solid was extracted with 15% $H_2O$ in acetone (4×). The filtrate was concentrated under reduced pressure to afford a slightly yellow oil. The addition of $H_2O$ (1.5 mL) afforded N-acetyl tyrosine as a white precipitate (670 mg, 3.00 mmol, 22%) that was washed with $H_2O$ (3×). The washings were saved for later precipitations. To a solution of N-acetyl tyrosine (76 mg, 0.34 mmol) in NaOH (aq) (0.5 N, 0.61 mL, 0.31 mmol) was added $K_2HPO_4$ (aq) (1 M, 0.61 mL, 0.61 mmol). This vigorously stirred solution was cooled to 0° C., and cyclohexyl isocyanate (48 μL, 47 mg, 0.37 mmol) was added dropwise to the reaction. During the addition, 0.5 M NaOH (aq) (4 drops) was added to maintain the pH between pH 8 and 9. After the addition was complete, the reaction was warmed to rt and stirred for 3 h. A white precipitate had formed, and the resulting suspension was washed with Et$_2$O (2×). The aqueous layer was separated and carefully acidified to pH 2 with 6 N HCl (aq). The desired product xxx precipitated as a white solid (89 mg, 0.26 mmol, 76%) that was filtered and washed with H$_2$O (3×).

Example 2

Figure 17:
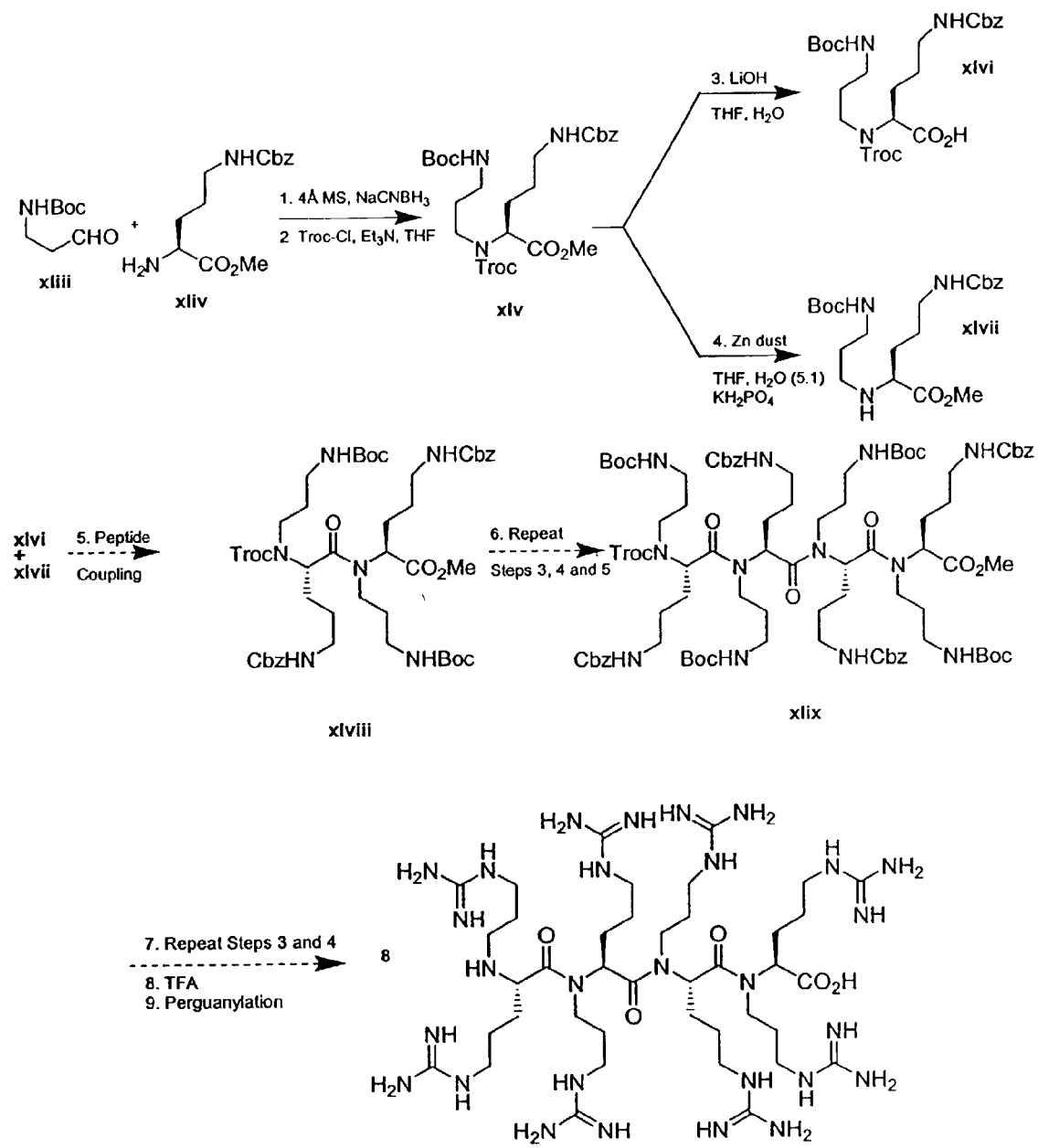
FIG. 17 provides Scheme 9 illustrating the preparation of transport reagents having a peptide/peptoid hybrid backbone. Coupling of a biological agent can be accomplished at either the N-terminus or the C-terminus.

This example illustrates the preparation of a peptide/peptoid hybrid transport reagent that can be attached to a therapeutic agent at either the amino- or carboxy terminus. Synthesis can be carried out as outlined in Scheme 9 (see FIG. 17).

Preparation of Monomeric Units

Aldehyde xliii. To a solution of 3-amino-1-propanol (0.750 mL, 737 mg, 9.82 mmol) in THF (7 mL) were sequentially added di-t-butyldicarbonate (2.35 g, 10.8 mmol) and a solution of sodium carbonate (2.08 g, 19.6 mmol) in H$_2$O (5 mL). After vigorously stirring for 2 h, the reaction mixture was poured over EtOAc. The residual solid was titurated with EtOAc, and the combined organic phase was washed with sat. NaHCO$_3$ (aq). The organic layer was separated, dried over MgSO$_4$, filtered and concentrated under reduced pressure to provide a crude pale yellow oil (1.66 g, 9.49 mmol, 97% crude) that was used without further purification. To a solution of this crude alcohol (1.05 g, 6.01 mmol) in CH$_2$Cl$_2$ (7 mL) was added a solution of KBr (722 mg, 6.07 mmol) in H$_2$O (3 mL). TEMPO (9 mg, 0.06 mmol) was added, and the biphasic mixture was cooled to 0° C. After stirring for 10 min, a solution of NaOCl (0.7 M, 9.44 mL, 6.61 mmol) and NaHCO$_3$ (1.84 g, 17.4 mmol) in H$_2$O (9 mL) was added dropwise as to maintain the internal temperature of the reaction below 10° C. After stirring for 1.5 h, additional NaOCl (0.7 M, 2.00 mL, 1.4 mmol) was added, and TLC analysis indicated that the starting material was consumed within 20 min. The reaction was then quenched with sat. Na$_2$S$_2$O$_3$ (aq), and the product was extracted with CH$_2$Cl$_2$ (2×). The combined organic phase was separated, dried over MgSO$_4$, filtered and concentrated under reduced pressure. The resulting crude product was purified via column chromatography to afford the desired aldehyde xliii (792 mg, 4.58 mmol, 76%).

H-Orn(Z)—OMe.HCl (xliv). To a solution of H-Orn(Z)—OH (1.00 µg, 3.76 mmol) in anhydrous MeOH (25 mL) at 0° C. was slowly added thionyl chloride (1.37 mL, 2.24 g, 18.8 mmol) as to maintain the internal reaction temperature below 10° C. After the addition was complete, the cold bath was removed, and stirring was continued for at rt 18 hours. The reaction was then concentrated under reduced pressure to afford a yellowish solid. Recrystallization with MeOH:EtOAc (1:6) afforded the desired product xliv as a white solid (600 mg, 0.190 mmol). The filtrate and EtOAc washings were cooled for 48 h at −20° C. to provide additional product xliv (177 mg, 0.56 1 mmol). The two batches (total: 777 mg, 2.46 mmol, 65%) were combined for further use.

Alkylated Troc-Orn(Z)—OMe (xlv). To a biphasic mixture of EtOAc (20 mL) and sat. NH$_4$OH (20 mL) was added solid H-Orn(Z)—OMe.HCl (184 mg, 0.582 mmol). The mixture was shaken in a separatory funnel until the solid dissolved. The organic layer was separated, dried over MgSO$_4$, filtered and concentrated under reduced pressure to afford the free amine of H-Orn(Z)—OMe. To a solution of this amine (142 mg, 0.507 mmol) in anhydrous CH$_2$Cl$_2$ (5 mL) were added 4 Å molecular sieves. To this suspension was added a solution of aldehyde xliii (84 mg, 0.49 mmol) in CH$_2$Cl$_2$ (2 mL). After stirring at it for 20 h, solid NaCNBH$_3$ (48 mg, 0.76 mmol) was added in two portions 45 min apart. The reaction was stirred for 18 h, and the mixture was then filtered. The filtrate was concentrated under reduced pressure, redissolved in EtOAc, poured over sat. Na$_2$CO$_3$ (aq), and washed with 5% citric acid (aq). The organic layer was then separated, dried over MgSO$_4$, filtered and concentrated under reduced pressure to afford a crude oil that was used without further purification. To a solution of the crude secondary amine in anhydrous THF (5 mL) were sequentially added triethylamine (0.149 mL, 108 mg, 1.07 mmol) and 2,2,2-trichloroethyl chloroformate (0.101 mL, 155 mg, 0.73 1 mmol). A white precipitate immediately formed, and after stirring for 15 min, the reaction was quenched with sat. NaHCO$_3$ (aq). The resulting mixture was poured over EtOAc, and the organic layer was washed with 5% citric acid (aq), sat. NaHCO$_3$ (aq) and brine. The organic phase was separated, dried over MgSO$_4$, filtered and concentrated under reduced pressure. Column chromatography afforded the desired product xlv (98 mg, 0.16 mmol, 32% two steps).

Carboxylic acid (xlvi). To a mixture of the methyl ester xlv (10 mg, 16 µmol) in 1:1 THF:H$_2$O (0.8 mL) was added LiOH (aq) (1.0 M, 19 µL, 19 µmol). After stirring for 5 h, the reaction was diluted with EtOAc and quenched with sat. NaHCO$_3$ (aq). The aqueous layer was extracted with EtOAc (3×), and the combined organic phase was separated, dried over MgSO$_4$, filtered and concentrated under reduced pressure. The resulting film (7.0 mg, 12 µmol, 75% crude) was used without further purification.

Secondary amine (xlvii). A mixture of Zn dust (230 mg) in 10% HCl (aq) (2.5 mL) was vigorously stirred for 2 min. After filtering, the activated Zn was sequentially washed with H$_2$O (3×) and acetone (3×) and dried under high vacuum. The activated Zn (196 mg, 3.00 mmol) was added to a solution of the Troc carbamate substrate xlv (37 mg, 60 µmol) in anhydrous THF (2.0 mL) under N$_2$. Phosphate buffer (pH 4.8, 0.4 mL) was added, and the mixture was vigorously stirred for 45 min. The precipitate was washed with THF (5×), and the combined washings were concentrated under reduced pressure. The resulting oil was dissolved in CHCl$_3$ and poured over sat. Na$_2$CO$_3$ (aq). The aqueous layer was extracted with CHCl$_3$ (3×), and the combined organic phase was separated, dried over MgSO$_4$, filtered and concentrated under reduced pressure. Column chromatography led to the isolation of the desired product xlvii (18 mg, 41 µmol, 68%).

Following the process outlined in Scheme 9, monomeric units xlvi and xlvii can be coupled using standard peptide coupling procedures to produce xlviii. Repeating steps 3, 4 and 5 using xlviii as the starting materials provides xlix. Conversion of xlix to the transport reagent 1, can be accomplished by subjecting xlix to saponification (e.g., with LiOH, THF and water), protecting group (Troc) removal, TFA-mediated removal of Cbz protecting groups, and perguanidinylation using methods known in the art.

Example 3

Figure 18:
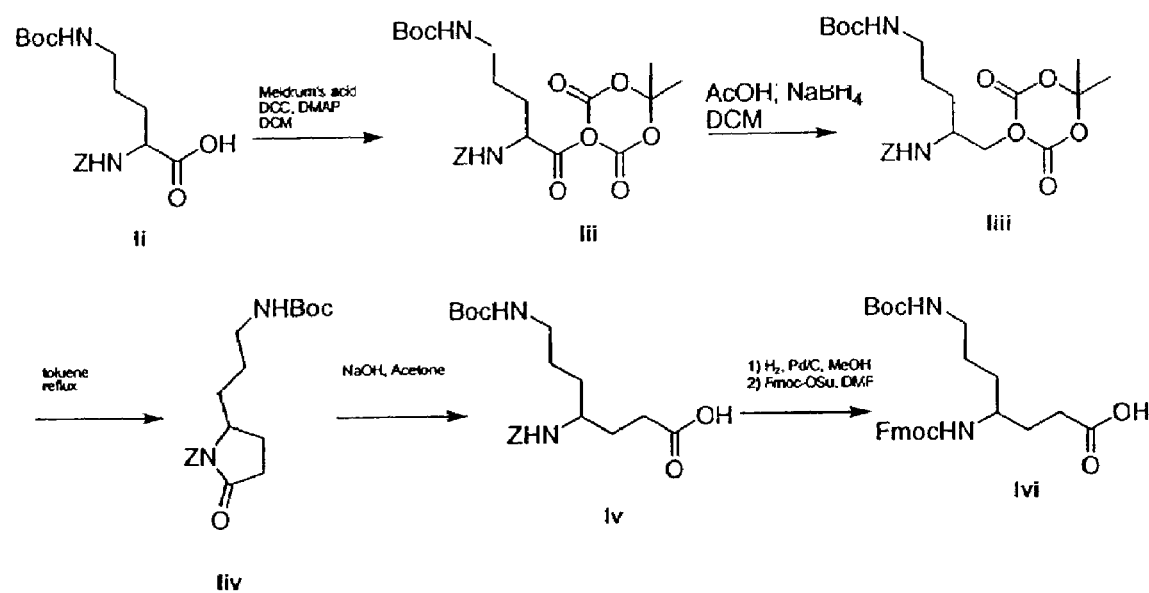
FIG. 18 provides Scheme 10 illustrating the preparation of a protected monomeric unit for the synthesis of transport reagents having a γ-peptide backbone.
Figure 19:
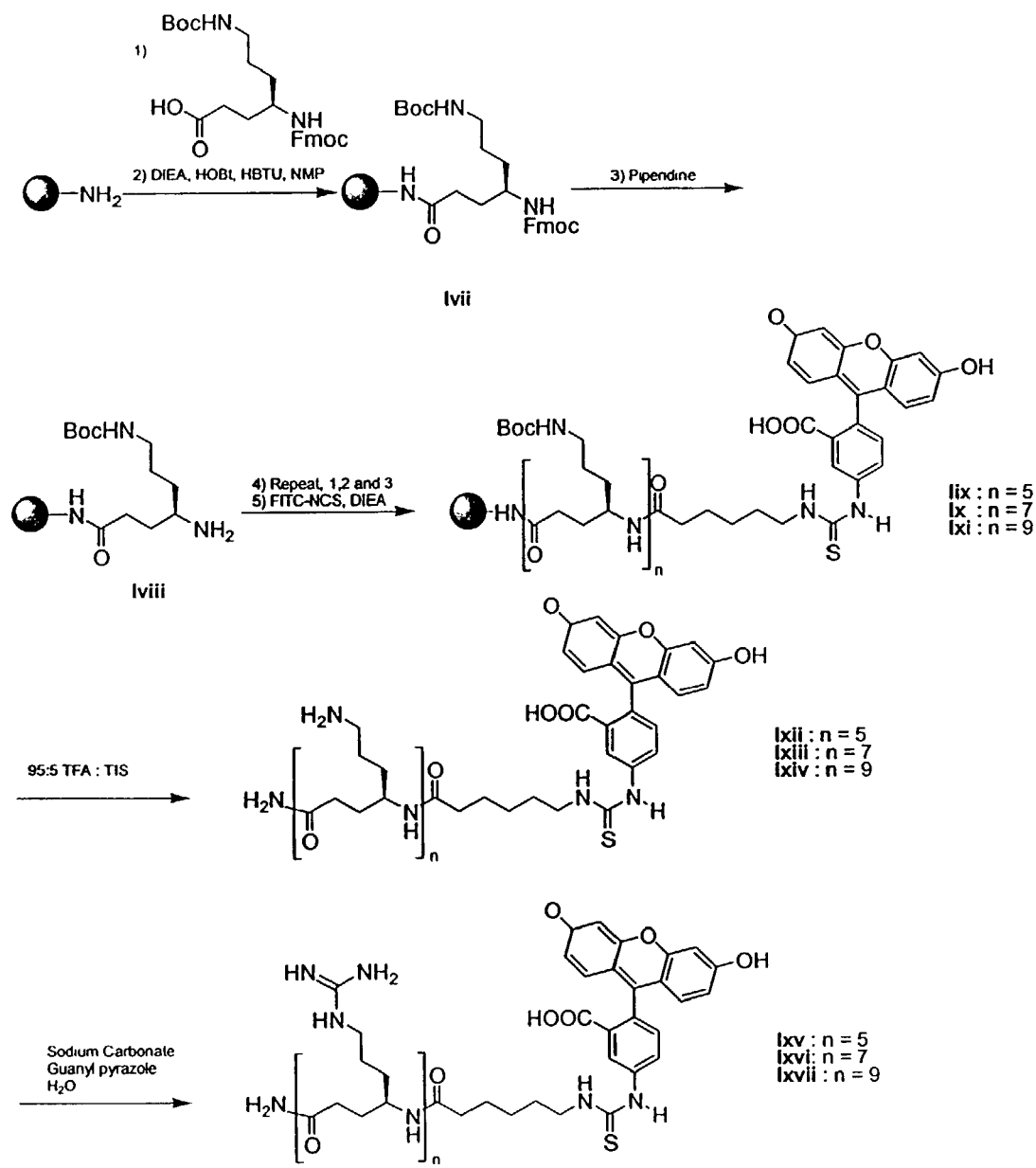
FIG. 19 provides Scheme 11 illustrating the solid-phase preparation of a transport reagent having a γ-peptide backbone beginning with the protected monomeric unit in Scheme 10.

This example illustrates the preparation of a series of γ-peptide transport reagents, as outlined in Schemes 10 and 11 (see FIGS. 18 and 19).

The γ-Ornithine monomer lvi was synthesized as shown in Scheme 10 [Smreina et al., *Tetrahedron*, 53,12867–12874 (1997)]. Treatment of the γ-Ornithine derivative li with Meldrum's acid and DCC gave lii which upon reduction with sodium acetoxy-borohydride gave liii. Compound liii underwent decarboxylative ring closure to yield lactam liv which upon basic hydrolysis gave lv. Z-deprotection and Fmoc-protection of the alpha nitrogen of lv gave the required monomer lvi.

Compound lvi was then coupled on the solid phase using standard peptide coupling conditions on a peptide synthesizer as shown in Scheme 11 to yield resin-bound oligomers lix–lxi. Deprotection of these from the resin using TFA also achieved the deprotection of the Boc groups to yield y ornithine oligomers lxii–lxiv which were perguanidinylated to yield the final γ arginine oligomers lxv–lxvii.

Experimental Section (R)-5-[(2-benzyloxycarbonylamino-3-(Boc) aminopropyl)-propyl]-2,2-dimethyl-1,3-dioxane-4,6-dione (liii). 20 mmol of Z-(Boc) Orn-OH was dissolved with 22 mmol of Meldrum's acid and 31 mmol of DMAP in methylene chloride (100 ml). The reaction mixture was cooled to −5° C. and a solution of 22 mmol of DCC in 50 ml of methylene chloride was added over an hour. The mixture was left to warm up to room temperature overnight. The precipitated DCU was then filtered and the remaining solution was washed 4× with 5% $KHSO_4$, 1× with brine and dried over $MgSO_4$ in the refrigerator for 5 hrs. This solution was then filtered and cooled to −5° C. and 13.3 ml of 98% acetic acid was added followed by portionwise addition of 1.85 g of sodium borohydride. The reaction mixture was stirred at <0° for 10 hrs and then washed 3× with brine. The organic phase was dried over $MgSO_4$, filtered and evaporated in vacuo to yield a crude product which was purified by column chromatography over silica gel using 1:1 hexane:ethyl acetate. $^1H$ NMR ($CDCl_3$) δ 7.3–7.4 (s, 3.8H), 5.1 (s, 1.93H), 4.8–4.9 (br s, 0.75H), 4.4–4.5 (br d, 0.9H), 3.8–4 (br d, 1.75H), 3.1–3.3 (d, 1.97H), 2–2.3 (m, 3.85H), 1.7–1.8 (2 s, 7.14 H), 1.5–1.7 (m, 4.95H), 1.4 (s, 9.59H)

(R)-N-benzyloxycarbonyl-5-t-butoxycarbonylamino propyl-2-pyrrolidinone (liv). 31 mmol of liii was refluxed in 100 ml of toluene for 3 hrs. The solvent was evaporated in vacuo to yield liv. $R_f$=0.54 (66% EtOAc in pentane; Molybdate); $^1H$ NMR ($CDCl_3$) δ 7.3–7.4 (br s, 4.05H), 5.1q, (1.99H), 4.6b (r s, 0.88H), 4–4.2 (br s, 1.26H), 3.2 (m, 2.28H), 2.4–2.6 (m, 2.54H), 2–2.2 (m, 1.24H), 1.7–1.9 (m, 1.9H), 1.4–1.6 (s, 12.26H); $^{13}CNMR$ ($CDCl_3$) δ 225.153, 173.848, 155.873, 151.44, 135.24, 134.42, 128.62, 128.43, 128.23, 105.47, 77.42, 77.21, 77.00, 76.57, 68.05, 61.54, 57.65, 40.12, 31.24, 30.77, 28.39, 26.14, 22.68, 17.

Gamma-Z-(Boc)Orn-OH (lv). 34 mmol of liv was dissolved in acetone (60 ml) and 1M aq. NaOH (90 ml). The reaction mixture was stirred at room temperature for 30 mts. The acetone was removed in vacuo and the aq. soln acidified with 6M HCl to pH 2. The product crashed out as a white solid which was collected by filtration. $^1H$ NMR ($CDCl_3$) δ 7.2–7.4 (s, 4.42H), 5.05 (s, 1.98H), 4.8–5 (br s, 1.2H), 3.4–3.6 (br s, 1.01H), 3–3.2 (d, 1.97H), 2.3 (m, 1.96H), 1.5 (m, 1.89H), 1.3 (s, 12.5H); $^{13}C$ NMR ($CDCl_3$) δ 177.66, 156.44, 156.10, 136.44, 128.51, 128.11, 128.03, 79.31, 77.43, 77.21, 77.00, 76.57, 67.26, 66.74, 51.64, 50.79, 40.22, 32.63, 30.67, 30.40, 28.38, 26.6.

Gamma-Fmoc-(Boc)Orn-OH (lvi). 11 mmol of lv was treated with 10% Pd/C (0.4 mol %) in 300 ml of MeOH for 4 hrs till TLC indicated complete consumption of starting material and then the solvent was evaporated in vacuo. The remaining yellow oil was then dissolved in 9% Sodium carbonate till the solution was basic and then Fmoc-OSu (11 mmol) was added as a solution in DMF (25 ml). The reaction was stirred at room temperature for 2 hrs. The reaction mixture was then acidified with 12M Hcl until acidic and extracted with EtOAc (3×, 100 ml each). The combined organics were then washed with brine and dried over Sodium sulfate. The solvent was evaporated in vacuo to yield a yellow solid which was purified by column chromatography over silica. $^1H$ NMR ($CDCl_3$) δ 7.6–7.8 (m, 2.07H), 7.4–7.6 (m, 2.2H), 7.2–7.4 (m, 9.61H), 5.1 (s, 2H), 4.9 (br t, 0.73H), 4.7 (d, 0.52H), 4.5 (s, 0.52H), 4.4 (d, 1.63H), 4.1 (t, 1.13H), 3.6 (br s, 0.87H), 3.15 (s, 1.8H), 2.3 (d, 1.56H), 2.05 (br m, 0.57H), 1.8 (br m, 0.7H), 1.1–1.5 (br m, 5.95H); $^{13}C$ NMR ($CDCl_3$) δ 177.5, 156.5, 143.7, 141.3, 136.5, 128.5, 127.6, 125.0, 119.9, 94.0, 77.4, 77.1, 76.5, 66.7, 66.2, 51.6, 50.6, 47.3, 47.1, 40.5, 32.5, 30.5, 26.3, 26.1, 25.7.

| Compound | ES-MS calcd | found |
|---|---|---|
| g-Orn5 (lix) | 1230.6 (z1) | 1230.6 (z1) |
| g-Orn7 (lx) | 1515.0 (z1), | 1514.5 (z1) |
|  | 758.5 (z2) | 1757.9 (z2) |
| g-Orn9 (lxi) | 600.7 (z3) | 600.7 (z3) |
| g-R5 (lxii) | 1440.8 (z1) | 1452.7 (z1 + Na) |
| g-R7 (lxiii) | 905.6 (z2) | 905.4 (z2) |
| gR9 (lxiv) | 1089.86 (z2) | 1089.7 (z2) |

Example 4

This example illustrates the preparation of a glutaramide transport reagent, as well as the related urea (L=C(O)); oxalamide (L=C(O)C(O)); and succinamide (L=C(O)$CH_2CH_2C(O)$) derivatives. Synthetic routes are provided in Scheme 6 (see FIG. 14).

Example 5

Figure 20:
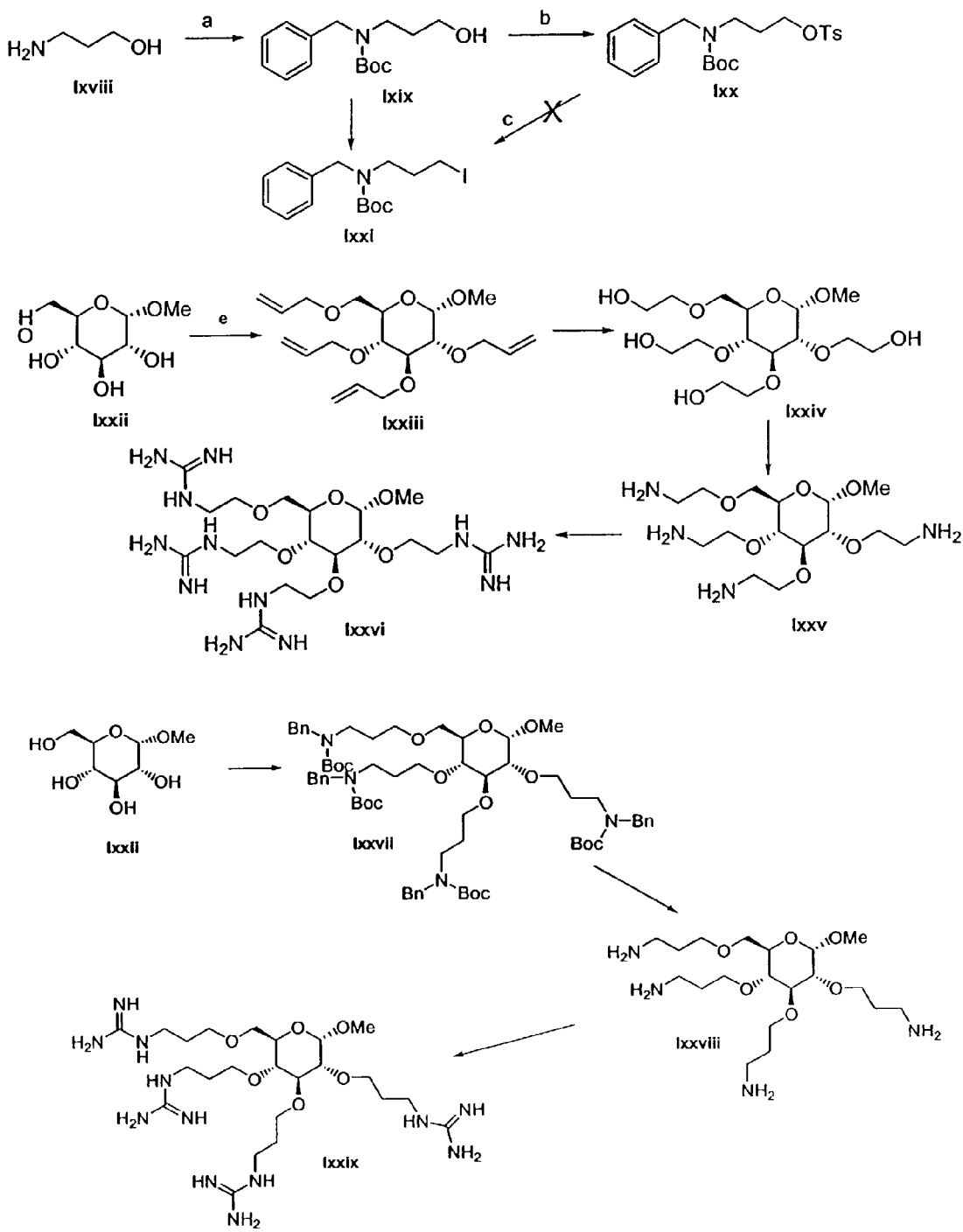
FIG. 20 provides Scheme 12 illustrating the preparation of transport reagents having a monosaccharide backbone.

This example illustrates the preparation of a transport reagent on a monosaccharide backbone (see Scheme 12, FIG. 20).

As shown in Scheme 12, 3-aminopropanol can be protected with both a benzyl group and a Boc group according to established methods to provide lxix. Displacement of the hydroxy group with iodine to provide lxxi can be accomplished with $I_2$ and $PPh_3$. Treatment of monosaccharide lxxii with lxxi in the presence of an acid scavenger can produce lxxvii, which, after deprotection and guanidinylation according to methods described herein, provides the target transport reagent lxxix.

Preparation of a related transport reagent (lxxvi) is also illustrated in Scheme 12 and uses chemistry similar to that provided for the homologous compound lxxix.

Example 6

This example illustrates the preparation and evaluation of a series of carbamate transport reagents using fluorescein or biotin as a surrogate therapeutic agent. In each case, the synthesis begins with preparation of a monomer lxxxii, illustrated in Scheme 13 (see FIG. 21).

(1S)-(4-tert-Butoxycarbonylamino-1-hydroxymethyl-butyl)-carbamic acid 9H-fluoren-9-ylmethyl ester (lxxxi)

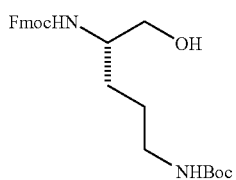

20 mL of dimethoxyethane was added to a dry 100 mL round bottom under $N_2$. 4.54 g (10.0 mmol) of Fmoc-Orn (Boc)—OH, lxxx, was added with stirring. The suspension was cooled in an ice/water/salt bath at −15° C. To the well suspended solid was added 1.11 mL (10 mmol) of N-methylmorpholine followed by 1.36 mL (10 mmol) of isobutyl chloroformate. The reaction was stirred vigorously for 1 min then vacuum filtered. The filtrate was stirred, and a solution of 570 mg (15 mmol) of sodium borohydride in 20 mL of water was immediately added. After 20 min, 150 mL of water was added, and after an additional hour, the resulting white precipitate was filtered, washed with water and hexane, then dried in a vacuum oven at 40° C. for 36 hours to give 3.75 g (8.52 mmol, 85%); white solid; TLC Rf (60% ethyl acetate/hexane): 0.45; mp: 107–109° C.; HRMS calcd (M+ less $C_4H_9O$, $C_{21}H_{23}N_2O_4$) 367.1658, found 367.1664. $^1$H NMR (300 MHz, $D_2O$) δ 7.74 (d, 2H, J=7.5), 7.58 (d, 2H, J=7.2), 7.38 (t, 2, J=7.3), 7.29 (t, 2H, J=7.2), 5.05 (m, 1H), 4.57 (m, 1H), 4.42 (d, 2H, J=6.6), 4.19 (t, 1H, J=6.5), 3.72–3.50 (m, 3H), 3.11 (m, 2H), 2.14 (m, 1H), 1.62–1.41 (m, 4H), 1.43 (s, 9H). $^{13}$C NMR (125 MHz, $CDCl_3$) δ 156.7, 156.2, 143.8, 141.2, 127.6, 127.0, 125.0, 119.9, 79.2, 66.4, 64.8, 52.8, 47.2, 40.2, 28.4, 28.2, 26.7.

Carbonic acid 5-tert-butoxycarbonylamino-2-(9H-fluoren-9-ylmethoxycarbonyl amino)-pentyl ester 4-nitro-phenyl ester (lxxxii)

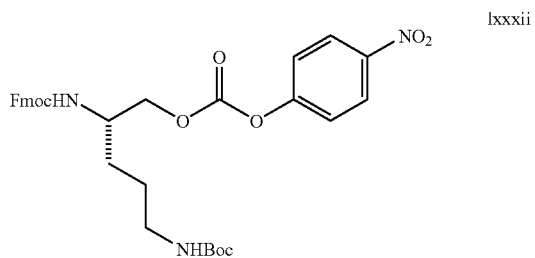

Compound lxxxi (5.705 g, 13.0 mmol) was dissolved in 65 mL of THF in a dry 250 mL round bottom flask under $N_2$. Pyridine (3.1 mL, 39 mmol) was added followed by a solution of 5.23 g (26 mmol) of 4-nitrophenyl chloroformate in 25 mL of THF. A white precipitate was immediately observed. After stirring for 2 hours at ambient temperature, starting material had been consumed (TLC). The solvent was concentrated in vacuo to approximately 5 mL. The residue was taken up in 100 mL of $CH_2Cl_2$ and washed with 1 M $NaHSO_4$ (5×30 mL) followed by 1M $Na_2CO_3$ (3×40 mL) and 25 mL of brine. The organic layer was dried over $MgSO_4$ and removed in vacuo to give 7.211 g (11.9 mmol, 92%) of lxxxii as a white solid; TLC Rf (50% ethyl acetate/hexane): 0.60; mp: 140–142° C.; HRMS (resubmitted). $^1$H NMR (300 MHz, $CDCl_3$) δ 8.25 (d, 2H, J=9.0), 7.77 (d, 2H, J=7.3), 7.60 (d, 2H, J=7.3), 7.27 (m, 6), 5.04 (m, 1H), 4.55 (m, 1H), 4.44 (t, 2H, J=6.3), 4.35–4.17 (m, 3H, J=6.5), 3.99 (m, 1H), 3.15 (m, 2H), 1.68–1.47 (m, 4H), 1.44 (s, 9H). $^{13}$C NMR (75 MHz, $CDCl_3$) δ 156.0, 155.3, 152.4, 145.4, 143.8, 143.7 141.3, 127.7, 127.0, 125.3, 124.9, 121.7, 120.0, 79.4, 70.7, 66.6, 50.0, 47.2, 40.0, 28.4, 28.2, 26.8.

Figure 22:
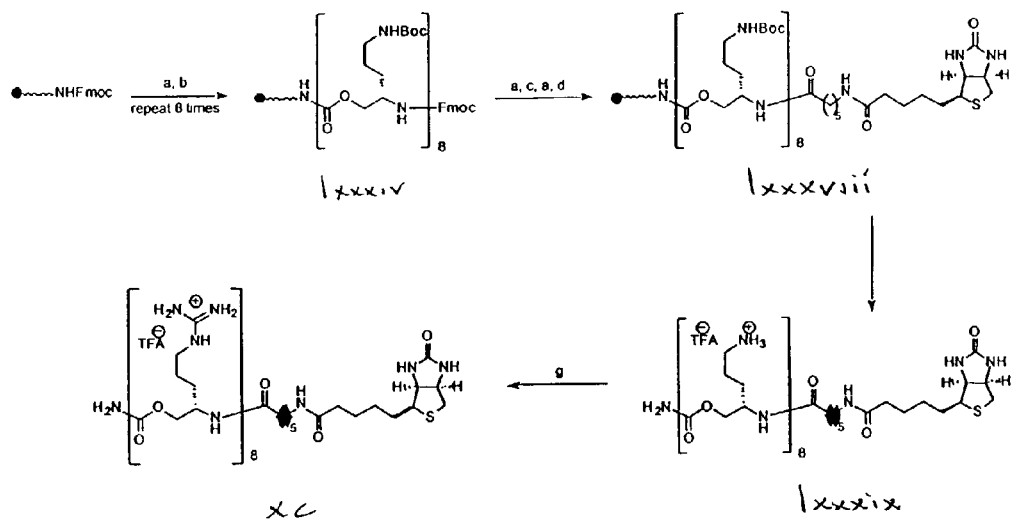
FIG. 22 provides Scheme 15 illustrating the solid and solution phase synthesis of a biotin-transporter conjugate wherein the transporter has a carbamate backbone.

Preparation of either the fluorescein or biotin conjugates proceeds as outlined in Schemes 14 and 15 (see FIGS. 21 and 22).

General Procedure for Synthesis of FITC-aca-$Orn^c_n$-$CONH_2$

Fmoc-amide resin (159 mg, 0.1 mmol, 0.63 mmol/g) was treated with 20% piperdine/DMF (10 mL) for 30 min (3×) to give the free resin-bound amine which was washed with DMF (3×10 mL). The resin was treated with a solution of lxxxii (1.0 mmol), DIEA (0.5 mmol), HOBT (2.0 mmol) in DMF (10 mL) for 4 hours then washed with DMF (3×10 mL). These four steps (deprotect, wash, couple, wash) were repeated to give oligomers of the desired length.

An aminocaproic acid spacer was appended by deprotection with 20% piperdine/DMF (10 mL) for 30 min. (3×) followed by treatment with Fmoc-aminocaproic acid (1.0 mmol), DIEA (0.5 mmol), HOBT (2.0 mmol), DIC (1.0 mmol), DMF (10 mL) for 1 h (2×). Fluoresceination was then accomplished by deprotection with 20% piperdine/DMF (10 mL) for 30 min (3×) and treatment with fluorescein isothiocyanate (0.5 mmol), DIEA (0.5 mmol), DMF (7 mL) for 18 hours.

The resin was washed with DMF (3×10 mL) then dichloromethane (5×10 mL). Cleavage of the oligomer from the resin was accomplished in a 15 mL plastic tube by treatment with 10 mL of 95:5 TFA/triisopropyl silane. After 12 hours, the reaction mixture was filtered, and the resin was washed with 10 mL of TFA. Concentration of the filtrate in vacuo to approximately 1.5 mL solvent followed by dropwise addition into cold ether afforded a yellow precipitate. The solid was pelleted by centrifugation and the liquid decanted. Reverse phase HPLC and lyophilization afforded the desired oligomer.

FITC-aca-Orn$^c_5$-CONH$_2$ (lxxxvi-a)

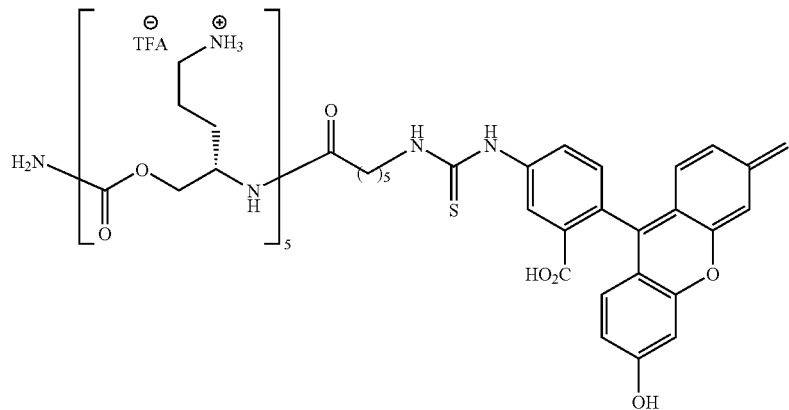

66 mg (0.036 mmol, 49%), yellow solid; RP-HPLC retention time=7.87 min; ES-MS (+ ionization) calcd (M+H, C$_{57}$H$_{86}$N$_{13}$O$_{16}$S) 1240.6, found 1240.5. $^1$H NMR (300 MHz, D$_2$O) δ 7.88 (s, 1H), 7.49 (d, 1H, J=7.5), 7.08 (d, 1H, J=8.1), 6.98 (d, 2H, J=8.7), 6.79 (s, 2H), 6.66 (dd, 2H, J=9.2, 2.0), 3.95–3.60 (m, 10H), 3.61–3.49 (m, 5H), 3.47–3.38 (m, 2H), 2.84–2.73 (m, 10H), 2.13–2.07 (m, 2H), 1.60–1.14 (m, 26H).

FITC-aca-Orn$^c_7$-CONH$_2$ (lxxxvi-b)

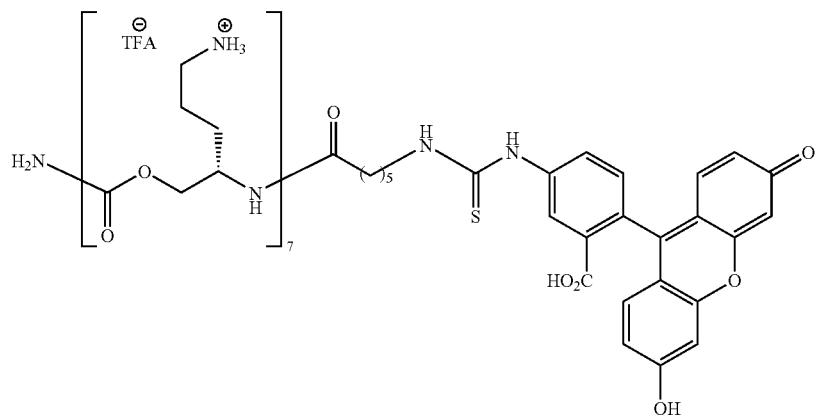

93 mg (0.061 mmol, 53%), yellow solid, RP-HPLC retention time=7.50 min; ES-MS (+ ionization) calcd (M+C$_{69}$H$_{110}$N$_{17}$O$_{20}$S) 1528.8, found 1528.6. $^1$H NMR (300 MHz, D$_2$O) δ 7.84 (s, 1H), 7.56–7.48 (m, 1H), 7.14 (d, 1H, J=7.8), 6.93 (d, 2H, J=8.4), 6.81 (s, 2H), 6.64 (d, 2H, J=8.7), 3.97–3.39 (m, 23H), 2.84–2.70 (m, 14H), 2.15–2.06 (m, 2H), 1.60–1.17 (m, 34H).

FITC-aca-Orn$^c{}_9$-CONH$_2$ (lxxxvi-c)

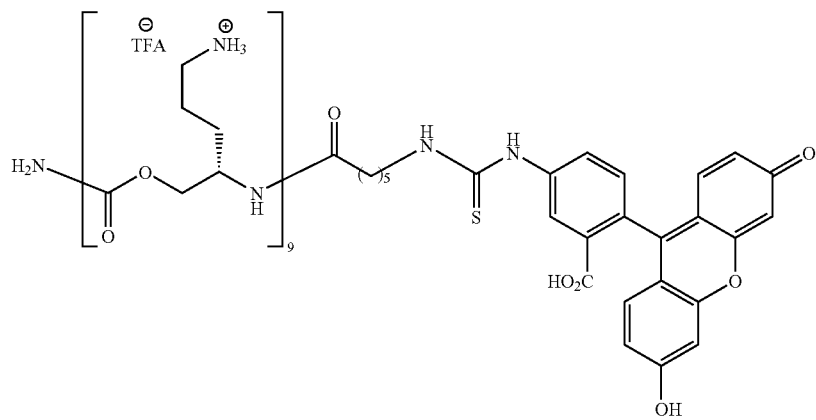

81 mg (0.028 mol, 28%), yellow solid, RP-HPLC retention time=7.23 min; ES-MS (+ ionization) calcd (M+C$_{81}$H$_{134}$N$_{21}$O$_{24}$S) 1817.0, fournd 1816.4. $^1$H NMR δ 7.89 (s, 1H), 7.51 (d, 1H, J=6.6), 7.03 (d, 1H, J=8.1), 6.87 (d, 2H, J=8.7), 6.71 (s, 2H), 6.60 (d, 2H, J=9.0), 3.97–3.62 (m, 18H), 3.62–3.45 (m, 9H), 3.45–3.35 (m, 2H), 2.88–2.68 (m, 18H), 2.14–2.04 (m, 2H), 1.63–1.14 (m, 42H).

Biotin-aca-Orn$^c{}_8$-CONH$_2$ (lxxxix)

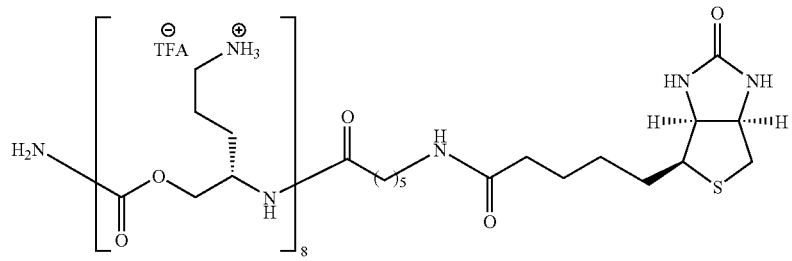

Fmoc-amide resin (159 mg, 0.1 mmol, 0.63 mmol/g) was treated with 20% piperdine/DMF (10 mL) for 30 min (3×) to give the free resin-bound amine which was washed with DMF (3×10 mL). The resin was treated with a solution of lxxxii (1.0 mmol), DIEA (0.5 mmol), HOBT (2.0 mmol) in DMF (10 mL) for 4 hours then washed with DMF (3×10 mL). These four steps (deprotect, wash, couple, wash) were 7 more time to give the resin-bound octamer.

An aminocaproic acid spacer was appended by deprotection with 20% piperdine/DMF (10 mL) for 30 min. (3×) followed by treatment with Fmoc-aminocaproic acid (1.0 mmol), DIEA (0.5 mmol), HOBT (2.0 mmol), DIC (1.0 mmol), DMF (10 mL) for 1 h (2×). Biotinylation was accomplished by deprotection with 20% piperdine/DMF (10 mL) for 30 min (3×) and treatment with biotin p-nitrophenylester (0.25 mmol), DIEA (0.5 mmol), DMF (7 mL) for 4 hours (2×).

The resin was washed with DMF (3×10 mL) then dichloromethane (5×10 mL). Cleavage of the oligomer from the resin was accomplished in a 15 mL plastic tube by treatment with 10 mL of 95:5 TFA/triisopropyl silane. After 12 hours, the reaction mixture was filtered, and the resin was washed with 10 mL TFA. Concentration of the filtrate in vacuo to approximately 1.5 mL solvent followed by dropwise addition into cold ether afforded a white precipitate. The solid was pelleted by centrifugation and the liquid decanted. Reverse phase HPLC and lyophilization afforded the desired oligomer, 84 mg (0.035 mmol, 35%) as a white solid; RP-HPLC retention time=4.82 min; ES-MS (+ ionization) calcd (M+H, C$_{64}$H$_{125}$N$_{20}$O$_{19}$S) 1509.9, found 1509.7. $^1$H NMR (300 MHz, D$_2$O) δ 4.42 (dd, 1H, J=4.7, 8.0), 4.23 (dd, 1H, J=4.4, 8.0), 4.02–3.70 (m, 16H), 3.65–3.53 (m, 8H), 3.17–3.11 (m, 1H), 2.98 (t, 2H, J=6.7), 2.86–2.75 (m, 17H), 2.59 (d, 1H, J=12.9), 2.11-2.02 (m, 4H), 1.64–1.08 (m, 44H).

Perguanindinylation:

A solution of carbamate amine (0.03 mmol) dissolved in deionized water (3 mL) was treated with potassium carbonate (5 equiv per amine residue) and pyrazole-1-Carboxamidine (5 equiv per amine residue) and heated at 40° C. for 36 h. The crude mixture was then acidified with TFA (0.3 mL), purified by RP-HPLC and lyophilized to afford the guanidinylated oligomer.

FITC-aca-Arg$^c_5$ (lxxxvii-a)
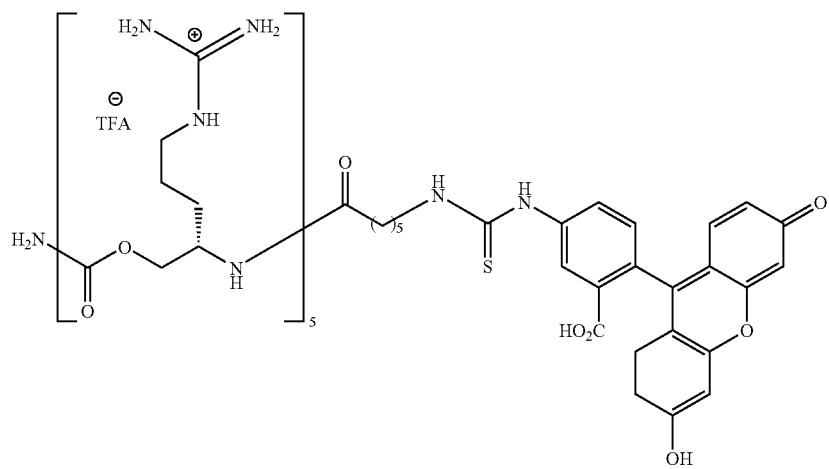
10 mg (0.0049 mmol, 26%), yellow solid; RP-HPLC retention time=8.35 min; ES-MS (+ ionization) calcd (M+H, $C_{62}H_{96}N_{23}O_{16}S$) 1450.1, found 1451.0. $^1$H NMR (300 MHz, $D_2O$) δ 7.93 (s, 1H), 7.61–7.49 (m, 1H), 7.18 (d, 1H, J=8.1), 7.00 (d, 2H, J=8.7), 6.88 (s, 2H), 6.71 (d, 2H, J=9.0), 3.95–3.41 (m, 17H), 3.03–2.86 (m, 10H), 2.16–2.07 (m, 2H), 1.57–1.13 (m, 26H).
FITC-aca-Arg$^c_7$ (lxxxvii-b)
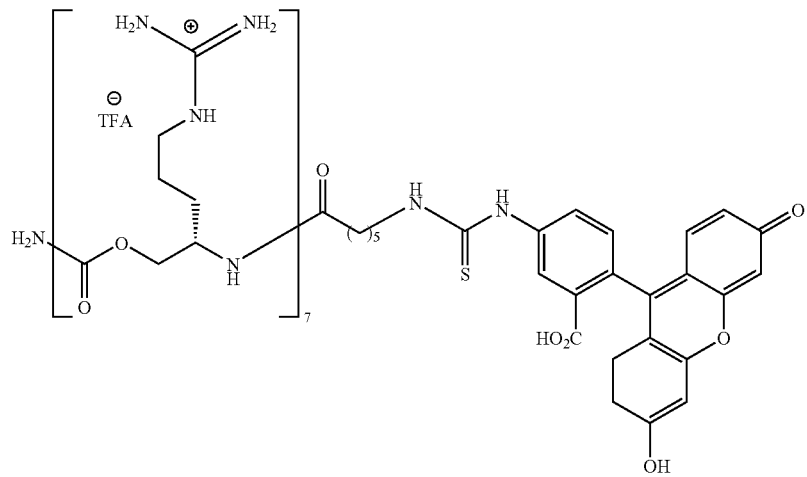
21 mg (0.0080 mmol, 27%), yellow solid; RP-HPLC retention time=8.38 min; ES-MS (+ ionization) calcd (M+H, $C_{76}H_{124}N_{31}O_{20}S$) 1822.9, found 1823.5. $^1$H NMR (300 MHz, $D_2O$) δ 7.92 (s, 1H), 7.62–7.55 (m, 1H), 7.17 (d, 1H, J=8.4), 6.92 (d, 2H, J=9.0), 6.83 (s, 2H), 6.65 (d, 2H, J=9.0), 3.96–3.40 (m, 23H), 3.04–2.88 (m, 14H), 2.18–2.10 (m, 2H), 1.58–1.14 (m, 34H).

FITC-aca-Arg$^c_9$ (lxxxvii-c)

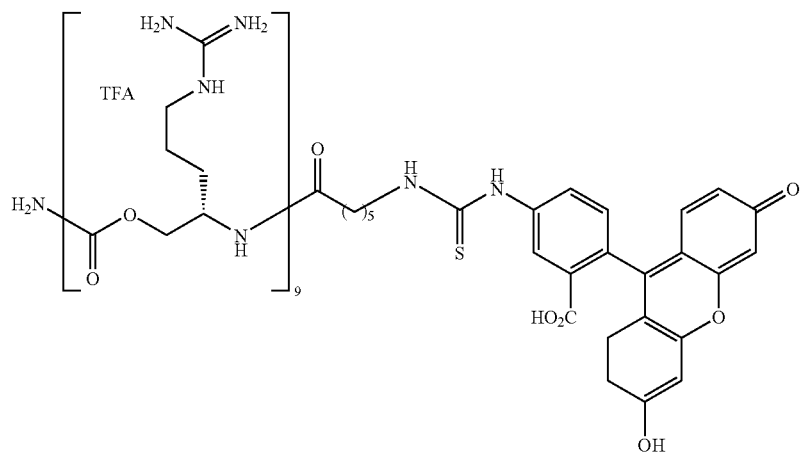

22 mg (0.0068 mmol, 40%), yellow solid; RP-HPLC retention time=8.29 min; ES-MS (+ ionization) calcd (M+2H, $C_{90}H_{151}N_{39}O_{24}S$; z=2) 1098.0, found 1098.5 $^1$H NMR (300 MHz, $D_2O$) δ 7.89 (s, 1H), 7.59–7.49 (m, 1H), 7.12 (d, 1H, J=8.1), 6.85 (d, 2H, J=9.0), 6.75 (s, 2H), 6.59 (d, 2H, J=9.0), 3.95–3.34 (m, 29H), 3.02–2.85 (m, 18H), 2.15–2.04 (m, 2H), 1.54–1.11 (m, 42H).

Biotin-aca-Arg$^c_8$ (xc)

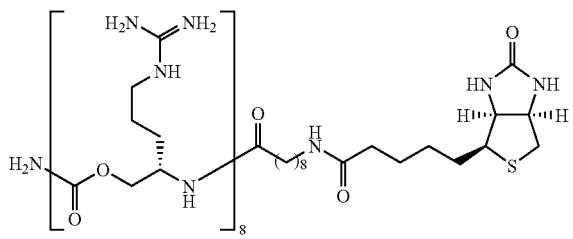

68 mg (0.028 mmol, 70%), white solid; RP-HPLC retention time=6.33 min; ES-MS (+ ionization) calcd (M+2H, $C_{72}H_{142}N_{36}O_{19}S$; z=2) 923.5, found 924.1 (z=2). $^1$H NMR (300 MHz, $D_2O$) δ 4.42 (dd, 1H, J=4.6, 8.0), 4.22 (dd, 1H, J=4.5, 7.8), 4.02–3.68 (m, 16H), 3.68–3.51 (m, 8H), 3.16–3.08 (m, 1H), 3.05–2.91 (m, 18H), 2.79 (dd, 1H, J=5.1, 12.9), 2.58 (d, 1H, J=12.9), 2.11–2.00 (m, 4H), 1.59–1.06 (m, 44H).

Figure 10C:
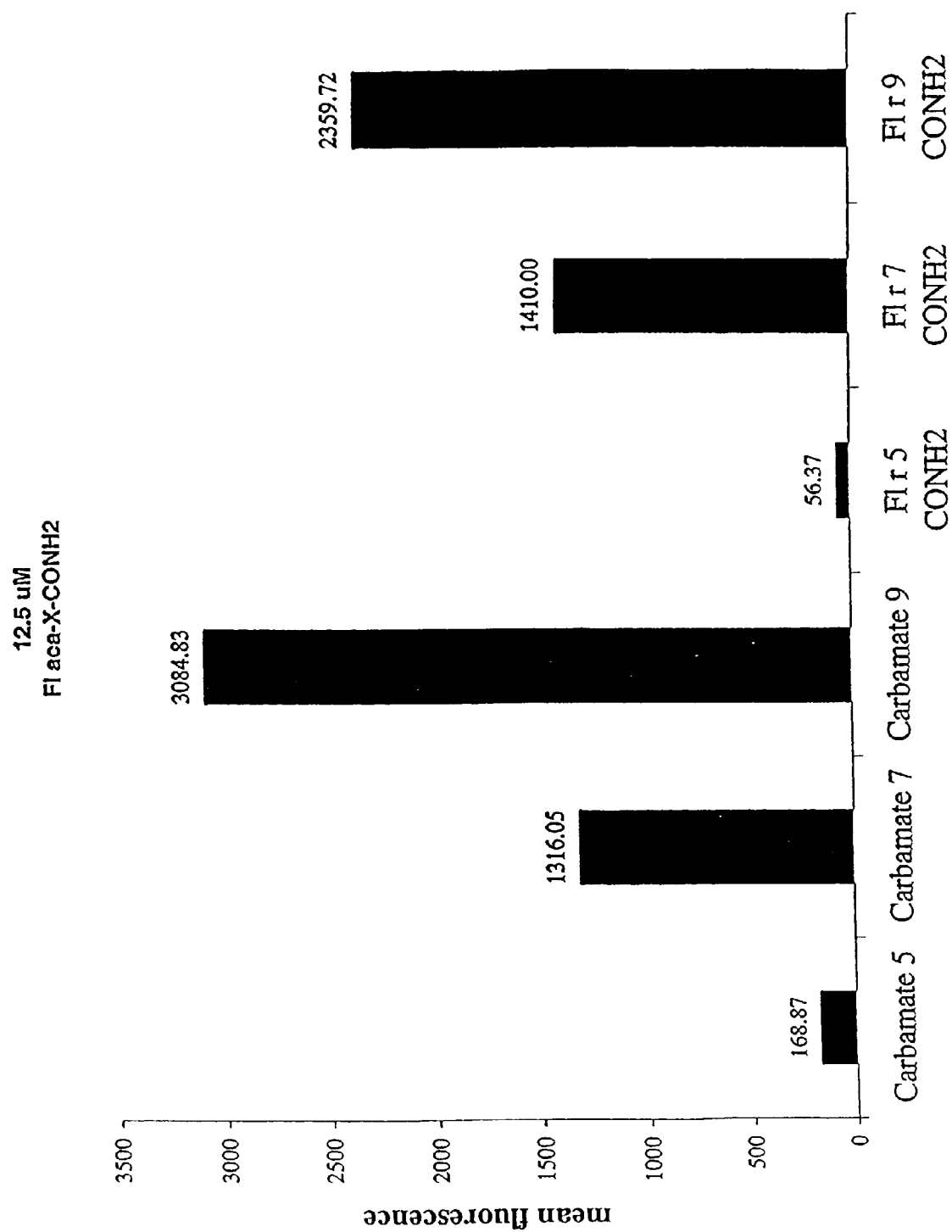

Results:

FIGS. 10a–c provide a series of three histograms showing the uptake observed at concentrations from about 12.5 μM to about 50 μM for pentamers, heptamers and nonamers of carbamate transporters, compared with the corresponding pentamers, heptamers and nonamers of D-arginine peptide amides. Each transporter was covalently attached to a fluorescein moiety to provide a suitable label and to illustrate the ability of the transport moiety to carry a small molecule into the cell.

Example 7

Figure 23:
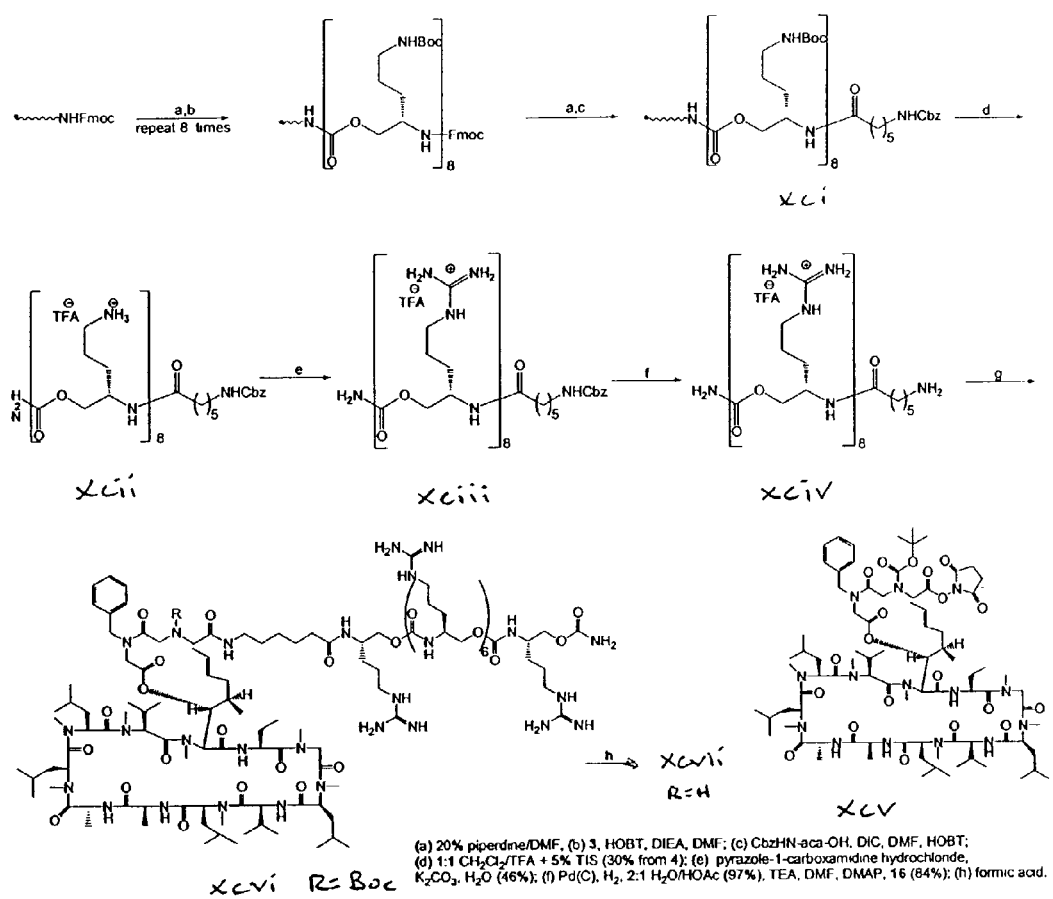
FIG. 23 provides Scheme 16 illustrating the solid and solution phase synthesis of a cyclosporin-transporter conjugate wherein the transporter has a carbamate backbone.

This example illustrates the preparation of a cyclosporin carbamate transport reagent conjugate (see Scheme 16, FIG. 23).

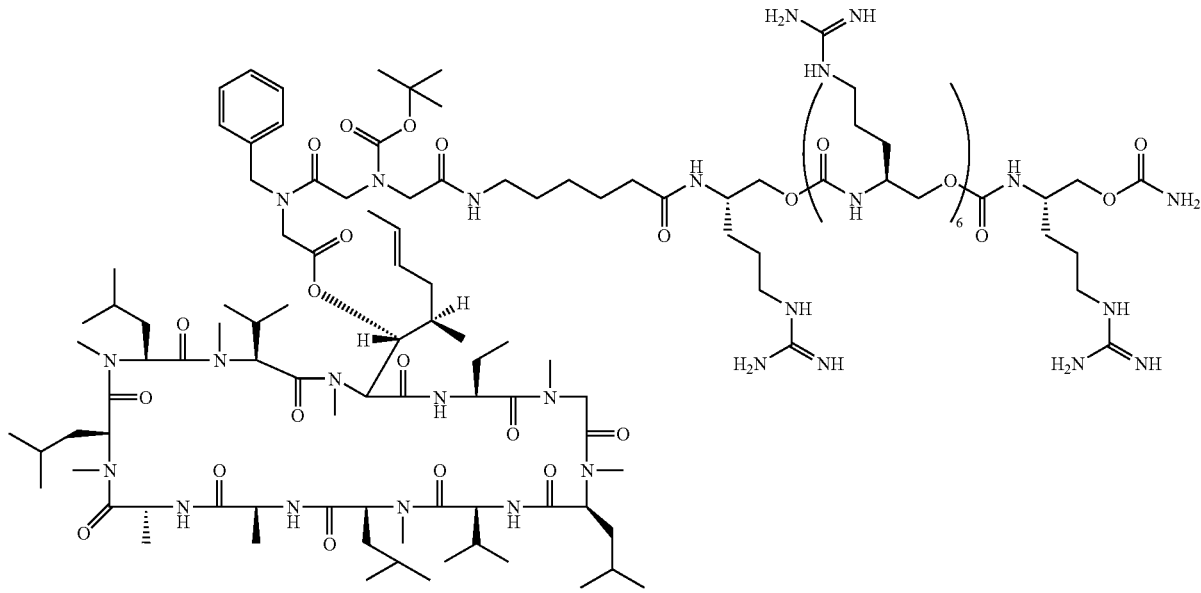

Non-releasable Cyclosporin—Rc8 Conjugate (xcvi)

issolved 18.6 mg of cyclosporin derivative xcv in 280 uL of DMF. Triethylamine (20 uL) and DMAP (1 mg) was added and the resulting solution was added to 37 mg of xciv. The solution was stirred for 16 hours, diluted with water, filtered through a plug of celite and purified by RP-HPLC to give 48 mg of a white solid (0.012 mmol, 84%).

Releasable Cyclosporin—Rc8 Conjugate (xcvii)

To solid xcvi (6 mg, 0.0019 mmol) was added 1 mL 96% formic acid. The solution was stirred for 24 hours, diluted with 10 mL water and lyophilized to give 7 mg of crude product.

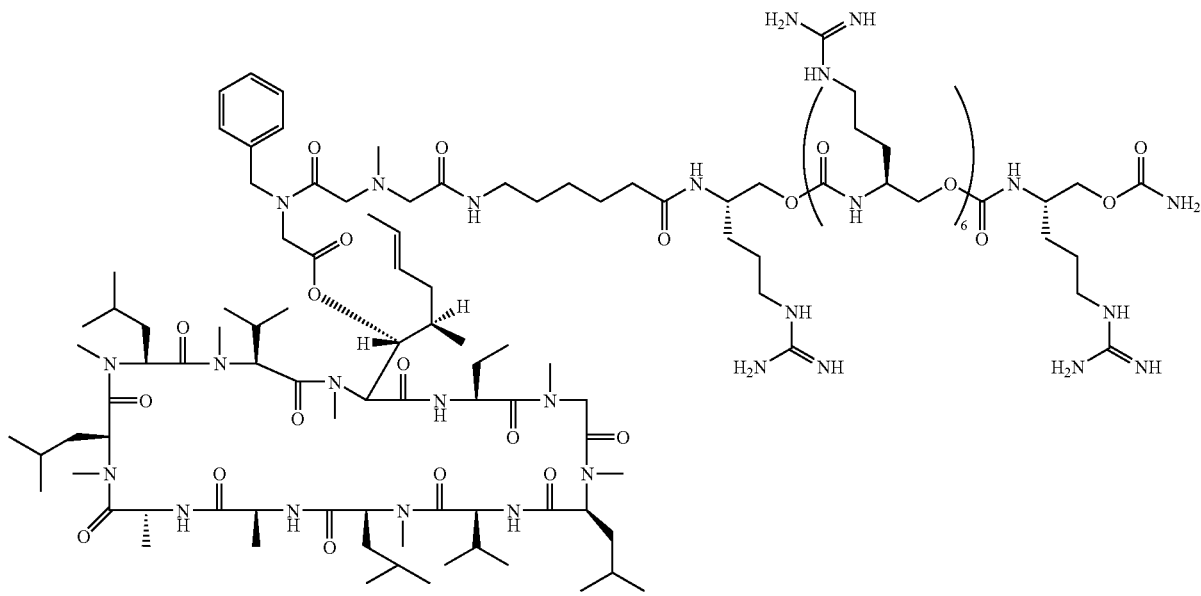

Example 8

Conjugate of Taxol and a Transport Reagent with pH-Releasable Linker

This example demonstrates the use of a general strategy for synthesizing prodrugs that have a transporter linked to a drug by a linker that releases the drug from the transporter upon exposure to physiological pH. In general, a suitable site on the drug is derivatized to carry an α-chloroacetyl residue. Next, the chlorine is displaced with the thiol of a cysteine residue that carries an unprotected amine.

Methods:

Synthesis of Taxol-2'-chloroacetyl

Taxol (89.5 mg, 104.9 μmol) was dissolved in $CH_2Cl_2$ (3.5 mL). The solution was cooled to 0° C. under an $N_2$-atmosphere. α-Chloroacetic anhydride (19.7 mg, 115.4 μmol) was added, followed by DIEA (14.8 mg, 115.4 μmol). The solution was allowed to warm to room temperature. After thin layer chromatography (tlc) analysis indicated complete consumption of starting material, the solvent was removed in vacuo and the crude material was purified by flash chromatography on silica gel (eluent: EtOAC/Hex 20%–50%) yielding the desired material (99.8 mg, quantitative).

$^1$H-NMR ($CDCl_3$): δ=8.13 (d, J=7.57 Hz, 2H), 7.72 (d, J=7.57 Hz, 2H), 7.62–7.40 (m, 1H), 6.93 (d, J=9.14 Hz, 1H), 6.29–6.23 (m, 2H), 6.01 (d, J=7.14 Hz, 1H), 5.66 (d, J=6.80 Hz, 1H), 5.55 (d, J=2.24 Hz, 1H), 4.96 (d, J=8.79 Hz, 1H), 4.43 (m, 1H), 4.30 (d, J=8.29 Hz, 1H), 4.20–4.15 (m, 2H), 3.81 (d, J=6.71 Hz, 1H), 2.56–2.34 (m, 3H), 2.45 (s, 3H), 2.21 (s, 3H), 2.19 (m, 1H), 1.95–1.82 (m, 3H), 1.92 s, (3H), 1.67 (s, 3H), 1.22 (s, 3H), 1.13 (s, 3H) ppm.

$^{13}$C-NMR ($CDCl_3$): δ=203.6, 171.1, 169.7, 167.3, 167.0, 166.9, 166.3, 142.3, 136.4, 133.6, 133.5, 132.9, 132.0, 130.1, 129.2, 121.1, 128.7, 128.6, 127.0, 126.5, 84.3, 81.0, 79.0, 76.3, 75.4, 75.2, 75.0, 72.2, 72.0, 58.4, 52.7, 45.5, 43.1, 40.1, 35.5, 26.7, 22.6, 22.0, 20.7, 14.7, 9.5 ppm.

Linkage of Taxol to Transporter

To the transporter having an attached cysteine residue, dissolved in DMF (1.0 mL) under an $N_2$-atmosphere is added DIEA (2.8 mg, 22.4 pmol). A solution of taxol-2'-chloroacetate (20.8 mg, 22.4 μmol) in DMF (1.0 mL) is added. Stirring at room temperature is continued for 6 hours. Water containing 0.1% TFA (1.0 mL) is added, and the sample is frozen and the solvents lyophilized. The crude material is purified by RP-HPLC (eluent: water/MeCN*0.1% TFA: 85%–15%).

Cytotoxicity Assay

The taxol conjugates can be tested for cytotoxicity in a 3-(4,5-dimethylthiazol-2-yl)-2,5-diphenyl-tetrazolium-bromide (MTT) dye reduction.

Example 9

Synthesis of Itraconazole-Transporter Conjugate

Figure 8:
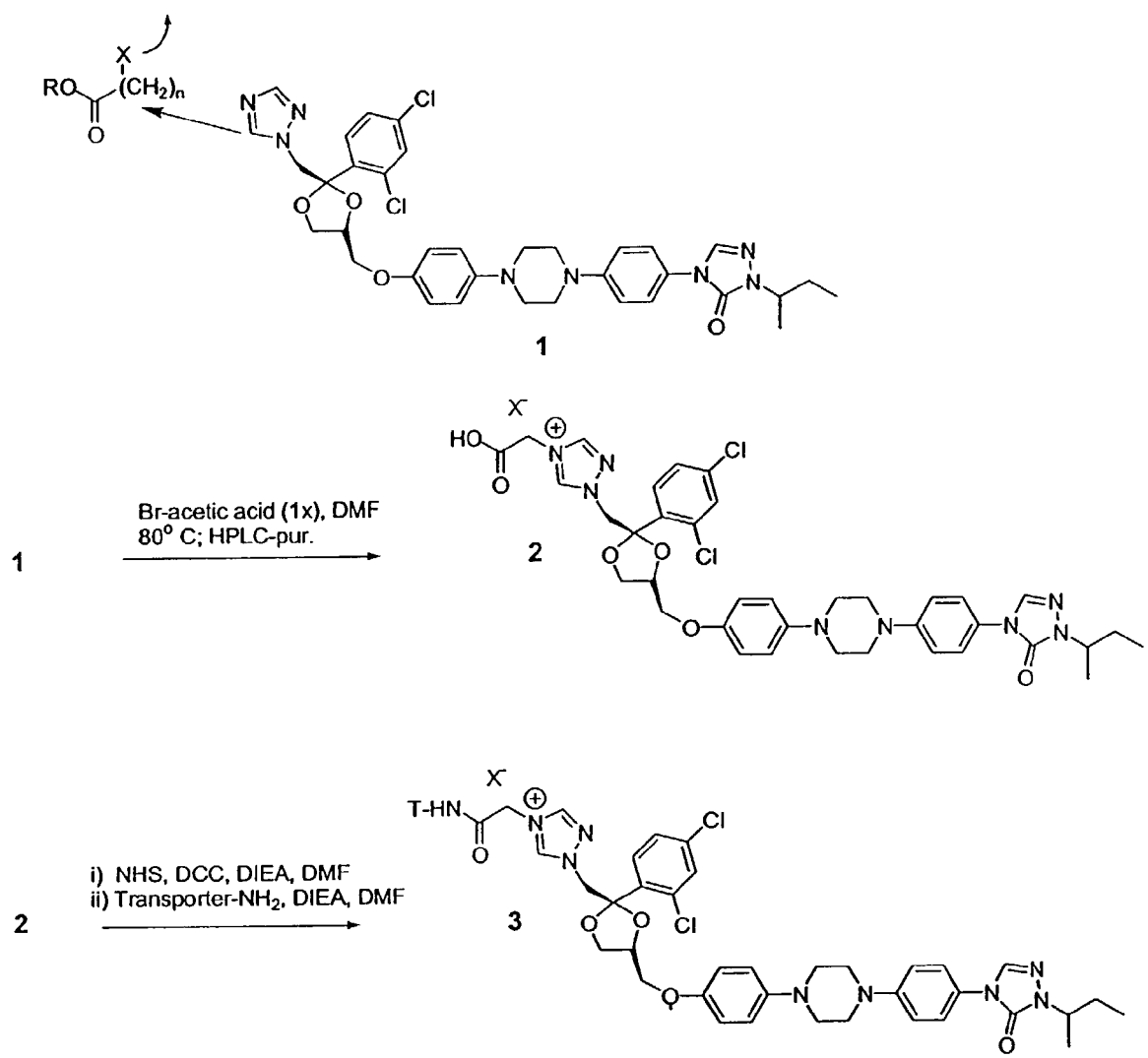
FIG. 8 shows a general strategy for attaching a transporter to a drug that includes a triazole ring structure.

This example provides one application of a general strategy for attaching a transporter to a compound that includes a triazole structure. The scheme, using attachment of itraconazole to a transporter is shown in FIG. 8. In the scheme, R is H or alkyl, n is 1 or 2, and X is a halogen.

The reaction involves making use of quaternization of a nitrogen in the triazole ring to attach an acyl group that has a halogen (e.g., Br, Fl, I) or a methyl ester. Compound 3 was isolated by HPLC. Proton NMR in $D_2O$ revealed itraconazole and transporter peaks.

The methyl ester provided yields of 70% and greater, while yields obtained using the Br-propionic acid/ester pair were 40–50%. The acyl derivative is then reacted with the amine of the transporter to form the conjugate. Alternatively, the halogenated acyl group can first be attached to the transporter molecule through an amide linkage, after which the reaction with the drug compound is conducted.

Example 10

Preparation of FK506 Conjugates

This Example describes the preparation of conjugates in which FK506 is attached to a transporter. Two different linkers were used, each of which can release FK506 at physiological pH (pH 5.5 to 7.5), but have longer half-lives at more acidic pH. These schemes are diagrammed in FIGS. 9A and 9B.

Linker 1: 6-maleimidocaproic hydrazide trifluroacetate

A solution of FK506 (1) (0.1 g, 124.4 μmol), 6-maleimidocaproic hydrazide trifluoroacetate (2) (0.126 g, 373.2 μmol) and trifluoroacetic acid (catalytic, 1 μL) in anhydrous methanol (5 mL) was stirred at room temperature for 36 h. The reaction was monitored by thin layer chromatography that showed almost complete disappearance of the starting material. [TLC solvent system—dichloromethane (95): methanol (5), $R_f$=0.3]. The reaction mixture was concentrated to dryness and dissolved in ethyl acetate (20 mL). The organic layer was washed with water and 10% sodium bicarbonate solution and then dried over sodium sulfate, filtered and concentrated. The residue was purified by column chromatography using dichloromethane (96): methanol (4) as eluent to give the hydrazone 3 (0.116 g, 92%).

A solution of the above hydrazone (3), transporter and diisopropylethylamine (1x) in anhydrous dimethylformamide (1 mL) is stirred under nitrogen at room temperature for 36 h when TLC indicates the complete disappearance of the starting hydrazone. Solvent is evaporated from the reaction mixture and the residue is purified by reverse phase HPLC using trifluoroacetic acid buffered water and acetonitrile.

Linker 2: 2-(2-pyridinyldithio) ethyl hydrazine Carboxylate

Figure 9B:
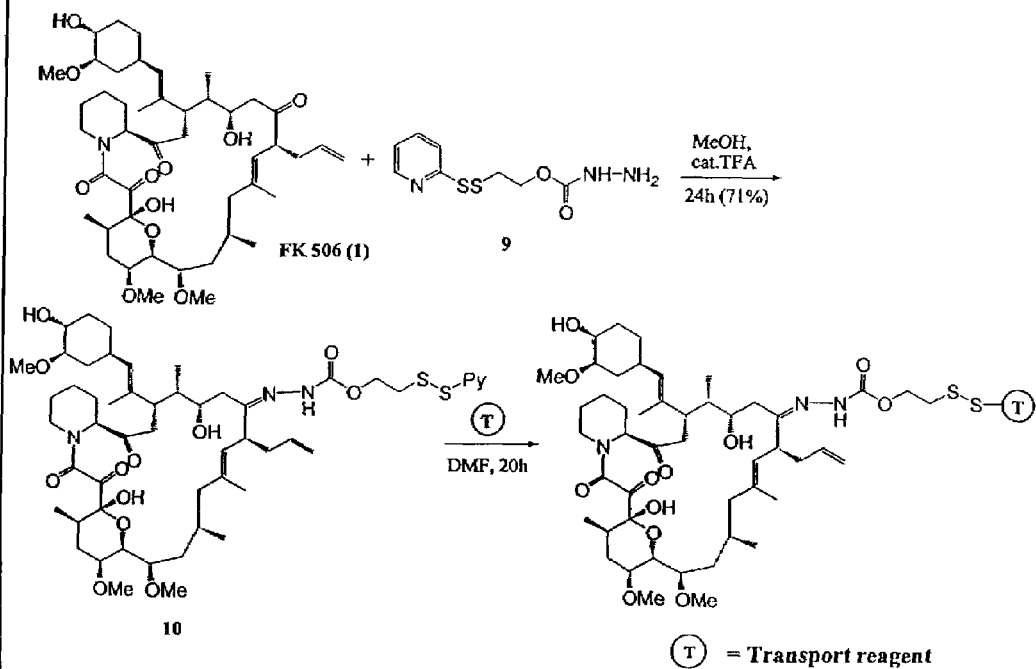

A solution of FK506 (1) (0.1 g, 124.4 μmol), 2-(2-pyridinyldithio) ethyl hydrazine carboxylate (9) (0.091 g, 373.2 mmol) and trifluoroacetic acid (catalytic, 1 μL) in anhydrous methanol (5 mL) was stirred at room temperature for 16 h. The reaction was monitored by thin layer chromatography that showed almost complete disappearance of the starting material. [TLC solvent system—ethyl acetate $R_f$=0.5]. The reaction mixture was concentrated to dryness and dissolved in ethyl acetate (20 mL). The organic layer was washed with water and 10% sodium bicarbonate solution and then dried over sodium sulfate, filtered and concentrated. The residue was purified by column chromatography using dichloromethane (97): methanol (3) as eluent to give the hydrazone conjugate 10 (0.091 g, 71%). Coupling of 10 to a transporter having a terminal cysteine residue can be accomplished via displacement of pyridinethiol as shown in FIG. 9B.

Example 11

This example illustrates the conjugation of cyclosporin to a transport moiety using a pH sensitive linking group (see FIG. 7).

In this example, cyclosporin is converted to its α-chloroacetate ester using chloroacetic anhydride. The ester is then treated with a transport reagent having an attached cysteine group to provide the cyclosporin conjugate.

Example 12

This example illustrates two methods of linking active agents to transport moieties. Illustration is provided for retinoic acid derivatives linked to poly-D-Arg derivatives but can be applied to linkages between other biological agents and the transport moieties of the present invention.

a. Linkage Between a Biological Agent Having an Aldehyde Functional Group

This example illustrates the preparation of a conjugate between a nonamer of D-arginine ($H_2N$-$r_9$-$CO_2H$·10TFA) and either all trans-retinal or 13-cis-retinal. Thus, condensation of either retinal with $H_2N$-$r_9$-$CO_2H$·10TFA in MeOH in the presence of 4 Å molecular seives at room temperature for four hours results in the formation of a Schiff base-type linkage between the retinal aldehyde and the amino terminal group. Purification of the conjugate can be accomplished by filtering the molecular sieves and removing methanol under reduced pressure.

b. Conjugation of Retinoic Acid to $r_7$-$CONH_2$

This example illustrates the preparation of a conjugate between retinoic acid and $r_7$-$CONH_2$ using the linking group

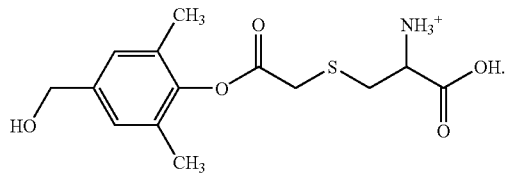

Here, retinoic acid is first combined with the chloroacetate ester of 4-hydroxymethyl-2,6-dimethylphenol to provide a suitable linking group conjugate. Combination of the linking group conjugate with retinoic acid in methylene chloride in the presence of dicyclohexylcarbodiimide and a catalytic amount of 4-dimethylaminopyridine provides a retinoid derivative which can then be condensed with $H_2NCys$-$r_7CONH_2$·8TFA in the presence of diisopropylethylamine (DMF, room temperature, 2 h) to provide the desired conjugated product.

Example 13

This example illustrates the use of spacer amino acids to provide a facial orientation of the guandinium head groups to one side of the transport reagent.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A compound having the formula:

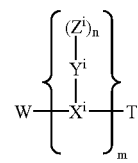

wherein the subscript m is an integer of from 6 to 25;

T is a member selected from the group consisting of a protected or unprotected first terminal functional group, a protected or unprotected linking group, and a linking group having an attached therapeutic agent;

W is a member selected from the group consisting of a protected or unprotected second terminal functional group, a protected or unprotected linking group, and a linking group having an attached therapeutic agent, with the proviso that T and W do not simultaneously contain an attached therapeutic agent;

each $X^i$ is a backbone subunit independently selected from:

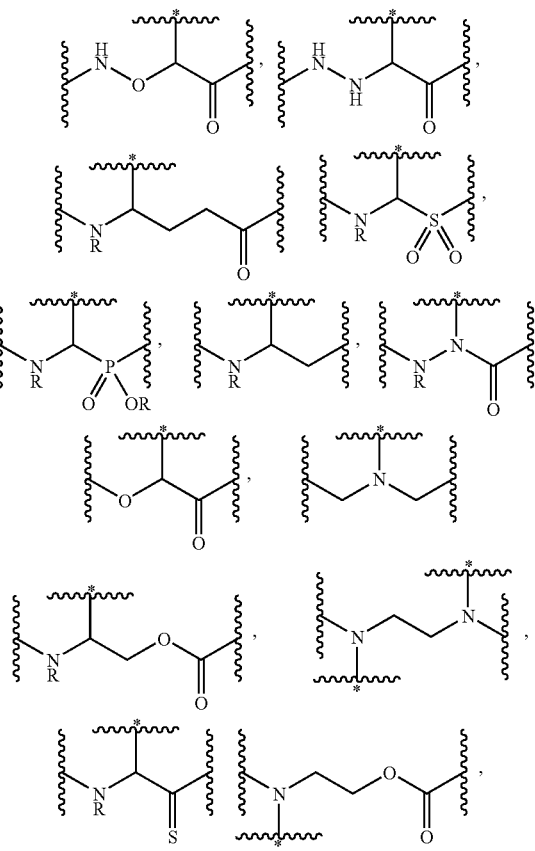

-continued

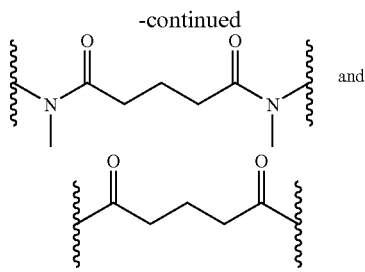

wherein
each R is a member selected from the group consisting of H and an amino acid sidechain; and
the starred wavy line indicates the point of attachment to $Y^i$ and the remaining wavy lines indicate the point of attachment along the backbone;
the superscript i is an integer of from 1 to m and denotes the position downstream of W;
each $Y^i$ is selected from the group consisting of H, an amino acid sidechain, aryl, and heteroaryl, when the subscript n is 0; or is selected from the group consisting of $(C_1-C_8)$alkylene, $(C_2-C_8)$alkenylene, $(C_2-C_8)$alkynylene, $(C_2-C_8)$heteroalkylene, $(C_3-C_8)$cycloalkylalkylene, $(C_2-C_8)$spirocycloalkylene, arylene, heteroarylene, and combinations thereof, when the subscript n is 1;
each $Z^i$ is a guanidinium moiety selected from the group consisting of:

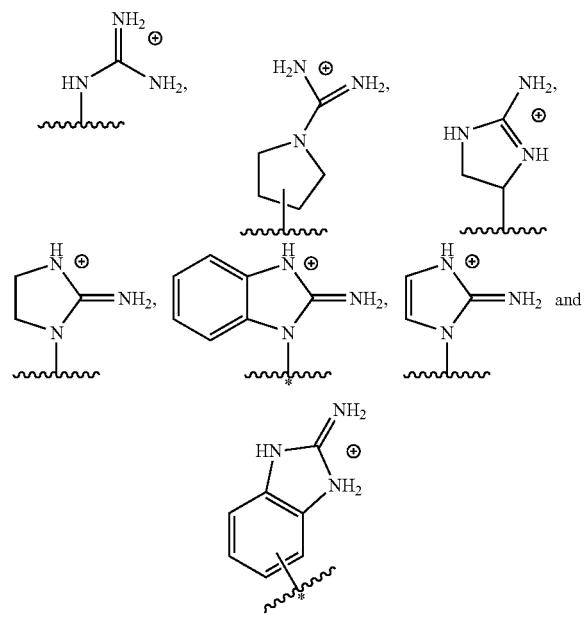

wherein the wavy line denotes the point of attachment to $Y^i$;
the attached therapeutic agent is different from each $Z^i$; and the subscript n is 0, 1 or 2, indicating the absence or presence of one or two Z guanidinium moieties at each i position;
with the proviso that the compound has at least 4 guanidinium moieties that can be the same or different and the portion of the compound joining W and T is not a polypeptide.

2. A compound of claim 1, wherein each $X^i$ is independently selected from the group consisting of:

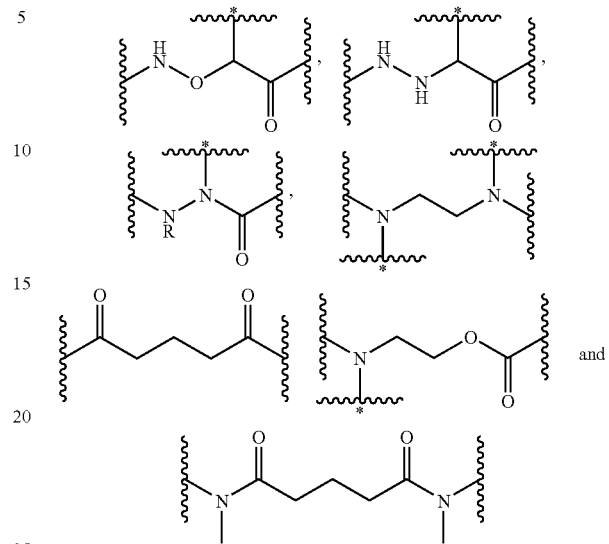

wherein
each R is a member selected from the group consisting of H and an amino acid sidechain; and
the starred wavy line indicates the point of attachment to $Y^i$ and the remaining wavy lines indicate the point of attachment along the backbone.

3. A compound of claim 2, wherein each $Z^i$ is selected from the group consisting of:

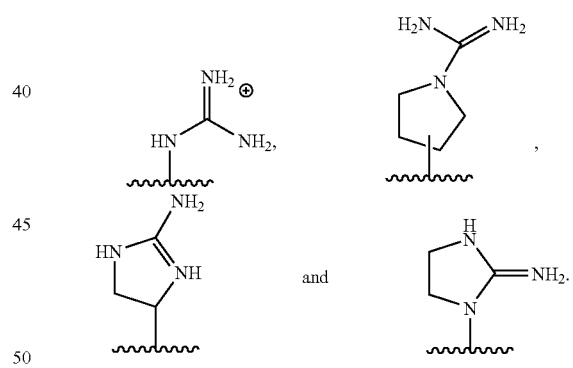

4. A compound of claim 3, wherein each $Y^i$ that is attached to a $Z^i$ is selected from the group consisting of $(C_1-C_8)$ alkylene, $(C_2-C_8)$alkenylene, $(C_2-C_8)$heteroalkylene, $(C_3-C_8)$cycloalkylalkylene, arylene and combinations thereof.

5. A compound of claim 4, wherein each $Y^i$ that is attached to a $Z^i$ is an unbranched $(C_3-C_7)$alkylene.

6. A compound of claim 5, wherein each $Y^i$ that is attached to a $Z^i$ is a $(C_4-C_6)$alkylene and each $Z^i$ is —NH—C(=NH_2)—NH_2.

7. A compound of claim 6, wherein for each odd integer i, n is 0 and for each even integer i, n is 1.

8. A compound of claim 6, wherein m is an integer of from 12 to 25, and with the proviso that the compound has from 6 to 8 guanidinium moieties that can be the same or different.

9. A compound in accordance with claim 1, having a carbamate backbone.

10. A compound in accordance with claim 9, having from 5 to 15 guanidinium head groups.

11. A compound in accordance with claim 9, having from 5 to 9 guanidinium head groups.

12. A compound in accordance with claim 1, having a glutaramide backbone.

13. A compound in accordance with claim 12, having from 5 to 15 guanidinium head groups.

14. A compound in accordance with claim 1, having a polyamine backbone.

15. A compound in accordance with claim 14, having from 5 to 15 guanidinium head groups.

16. A compound in accordance with claim 1, having a γ-peptide backbone.

17. A compound in accordance with claim 16, having from 5 to 15 guanidinium head groups.

18. A compound of claim 1, wherein W is a linking group having an attached biologically active agent and has the formula:

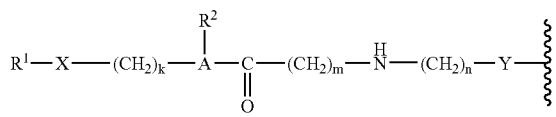

wherein:
R¹ the biologically active agent;
X is a linkage between a functional group on the biologically active agent R¹ and the remainder of W;
Y is a functional group attaching W to the remainder of the compound;
A is N or CH;
R² is hydrogen, alkyl, aryl, arylaikyl, acyl or allyl;
k and m are independently either 1 or 2; and
n is an integer of from 1 to 10.

19. A compound of claim 18, wherein Y is selected from the group consisting of O, NH, C(O)O, NHC(O) and C(O)NH.

20. A compound of claim 1, wherein W is a linking group having an attached biologically active agent and has the formula:

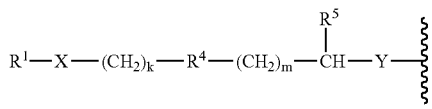

wherein:
R¹ the biologically active agent;
X is a linkage between a functional group on the biologically active agent R¹ and the remainder of W;
Y is a functional group attaching W to the remainder of the compound;
R⁴ is S, O, NR⁶ or CR⁷R⁸;
R⁵ OH, SH or NHR⁶;
R⁶ is hydrogen, alkyl, aryl, arylalkyl, acyl or allyl;
R⁷ and R⁸ are independently hydrogen, alkyl or arylalkyl; and
k and m are independently either 1 or 2.

21. A compound of claim 20, wherein Y is selected from the group consisting of O, NH, C(O)O, NHC(O) and C(O)NH.

22. A compound of claim 1, wherein W is a linking group having an attached biologically active agent and has the formula:

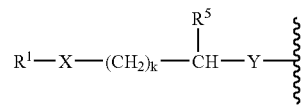

wherein:
R¹ is the biologically active agent;
X is a linkage between a functional group on the biologically active agent R¹ and the remainder of W;
Y is a functional group attaching W to the remainder of the compound;
R⁵ is H, OH, SH or NHR⁶;
R⁶ is hydrogen, alkyl, aryl, arylalkyl, acyl or allyl; and
k is 1 or 2.

23. A compound of claim 22, wherein Y is selected from the group consisting of O, NH, C(O)O, NHC(O) and C(O)NH.

24. A compound of claim 1, wherein W is a linking group having an attached biologically active agent and has the formula:

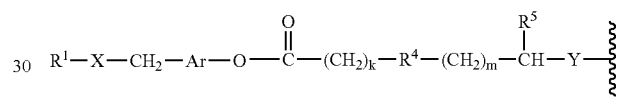

wherein:
R¹ the biologically active agent;
X is a linkage between a functional group on the biologically active agent R¹ and the remainder of W;
Y is a functional group attaching W to the remainder of the compound;
Ar is a substituted or unsubstituted aryl group, wherein the methylene and oxygen substituents are either ortho or para to one another;
R⁴ is S, O, NR⁶ or CR⁷R⁸;
R⁵ is H, OH, SH, CONHR⁶ or NHR⁶;
R⁶ is hydrogen, alkyl, aryl, arylalkyl, acyl or allyl;
R⁷ and R⁸ are independently hydrogen or alkyl; and,
k and m are independently either 1 or 2.

25. A compound of claim 24, wherein Y is selected from the group consisting of O, NH, C(O)O, NHC(O) and C(O)NH.

26. A method for enhancing transport of a selected therapeutic agent across a biological membrane, comprising
contacting said biological membrane with a compound of claim 1 wherein one of W or T comprises said therapeutic agent, and said one of W or T is covalently attached to the remainder of said compound of claim 1, thereby forming a conjugate,
whereby said contacting is effective to promote transport of said conjugate across said biological membrane at a rate that is greater than the trans-membrane transport rate of the therapeutic agent in non-conjugated form.

27. The method of claim 26, wherein said compound comprises a polymer consisting of from 7 to 25 subunits, at least 4 of which contain a guanidino sidechain moiety.

28. The method of claim 27, wherein each guanidino sidechain moiety is separated from another such moiety by from one to three non-guanidino or non-amidino subunit.

29. A method of claim 26, wherein said therapeutic agent is selected from the group consisting of anticancer agents, antibacterial agents, antiinflammation agents and antifungal agents.

30. A method of claim 29, wherein said agent is an anticancer agent.

31. A method of claim 29, wherein said agent is an antibacterial agent.

32. A method of claim 29, wherein said agent is an antiinflammation agent.

* * * * *

UNITED STATES PATENT AND TRADEMARK OFFICE
CERTIFICATE OF CORRECTION

| | | |
|---|---|---|
| PATENT NO. | : 7,169,814 B2 | Page 1 of 1 |
| APPLICATION NO. | : 10/318278 | |
| DATED | : January 30, 2007 | |
| INVENTOR(S) | : Rothbard et al. | |

It is certified that error appears in the above-identified patent and that said Letters Patent is hereby corrected as shown below:

Column 1:

• Please replace lines 12-18 with:

--FEDERALLY SPONSORED RESEARCH OR DEVELOPMENT
This invention was made with Government support under contracts CA065237, CA031841, and CA031845 awarded by the National Institutes of Health. The Government has certain rights in this invention.--

Signed and Sealed this
Nineteenth Day of April, 2011

David J. Kappos
*Director of the United States Patent and Trademark Office*